United States Patent [19]
Bjørn et al.

[11] Patent Number: 5,591,603
[45] Date of Patent: Jan. 7, 1997

[54] PROCESS FOR PREPARING APROTININ AND APROTININ ANALOGS IN YEAST CELLS

[75] Inventors: Soren E. Bjørn, Lyngby; Kjeld Norris, Hellerup; Viggo Diness, Charlottenlund; Leif Nørskov-Lauritsen, Køge; Niels D. Christensen, Kövenhavn; Claus Bregengaard; Fanny Norris, both of Hellerup; Lars C. Petersen, Hørsholm, all of Denmark

[73] Assignee: Novo Nordisk A/S, Bagsvaerd, Denmark

[21] Appl. No.: 84,718

[22] Filed: Jun. 23, 1993

Related U.S. Application Data

[63] Continuation-in-part of Ser. No. 24,925, Feb. 26, 1993, abandoned, which is a continuation of Ser. No. 466,408, Jun. 21, 1990, abandoned, and a continuation-in-part of Ser. No. 598,737, Nov. 19, 1990, Pat. No. 5,373,090, and a continuation-in-part of Ser. No. 827,687, Jan. 29, 1992, abandoned.

[30] Foreign Application Priority Data

| Aug. 28, 1987 | [DK] | Denmark | 4501/87 |
| Apr. 26, 1988 | [DK] | Denmark | 2254/88 |
| Oct. 1, 1990 | [DK] | Denmark | 2361/90 |
| Jun. 12, 1991 | [DK] | Denmark | 1118/91 |

[51] Int. Cl.$^6$ .............. C12N 15/81; C12N 15/15; C07K 14/81; C12P 21/02
[52] U.S. Cl. ............. 435/69.2; 435/255.2; 435/320.1; 536/23.5; 536/23.1; 530/300
[58] Field of Search .................. 435/69.2, 255.1, 435/255.2, 320.1; 536/23.1, 23.5; 530/300

[56] References Cited

U.S. PATENT DOCUMENTS

| 4,595,674 | 6/1986 | Tschesche et al. | 514/9 |
| 4,615,974 | 10/1986 | Kingsman et al. | 435/68 |
| 5,118,668 | 6/1992 | Auerswald et al. | 514/12 |
| 5,122,594 | 6/1992 | Yoshida et al. | 435/69.2 |
| 5,126,322 | 6/1992 | Colins et al. | 514/12 |

FOREIGN PATENT DOCUMENTS

| 2025070 | 4/1991 | Canada. |
| 0163539 | 12/1985 | European Pat. Off.. |
| 0200451 | 11/1986 | European Pat. Off.. |
| 0297362 | 1/1989 | European Pat. Off.. |
| 2188322 | 9/1987 | United Kingdom. |
| 2188933 | 10/1987 | United Kingdom. |

OTHER PUBLICATIONS

Cara Berman et al., J. Biol. Chem., vol. 261, No. 16, pp. 7115–7118 (Jun. 5, 1986).
Wilcken–Bergmann et al., EMBO Journal, vol. 5, No. 12, pp. 3219–3225 (1986).
Julius et al., Cell, vol. 32, 839–52 (Mar. 1983).
Fuller et al., Microbiology, pp. 273–278 (1986).
Marks et al., J. Biol. Chem., vol. 261, No. 16, pp. 7115–7118, 1986.
Schnabel et al., Biol. Chem. Hoppe–Seyler, vol. 367, pp. 1167–1176 (1986).
Fioretti et al., Biol. Chem., vol. 260, No. 21, pp. 11951–11955 (1985).
Coplen et al., Proteins, vol. 7, pp. 16–31 (1990).
Goldenberg et al., Nature, vol. 338, pp. 127–132 (Mar. 9, 1989).
Siekmann et al., Biol. Chem. Hoppe–Seyler, vol. 369, pp. 157–163 (Mar. 1988).

Primary Examiner—Garnette D. Draper
Assistant Examiner—Sally P. Teng
Attorney, Agent, or Firm—Steve T. Zelson, Esq.; Cheryl H. Agris, Esq.

[57] ABSTRACT

The present invention relates to methods for producing aprotinin and analogs thereof in yeast, synthetic genes encoding such products, expression vectors and transformed yeast cells. The invention further relates to aprotinin analogs, particularly analogs with increased specific inhibitory activity and/or reduced nephrotoxicity compared to native aprotinin, as well as compositions comprising such analogs.

13 Claims, 17 Drawing Sheets

```
        3         5                10                 15
    AspPheCysLeuGluProProTyrThrGlyProCysLysAlaArgIle
AAAGAGATTTCTGTTTGGAACCTCCATACACTGGTCCATGTAAAGCTAGAATC
    CTAAAGACAAACCTTGGAGGTATGTGACCAGGTACATTTCGATCTTAG
```

```
       20                25                30                 35
   IleArgTyrPheTyrAsnAlaLysAlaGlyLeuCysGlnThrPheValTyrGly
   ATCAGATACTTCTACAACGCCAAGGCTGGTTTGTGTCAAACTTTCGTTTACGGT
   TAGTCTATGAAGATGTTGCGGTTCGACCAAACACAGTTTGAAAGCAAATGCCA
```

```
           40               45                 50
   GlyCysArgAlaLysArgAsnAsnPheLysSerAlaGluAspCysMetArgThr
   GGCTGCAGAGCTAAGAGAAACAACTTCAAGTCTGCTGAAGACTGCATGAGAACT
   CCGACGTCTCGATTCTCTTTGTTGAAGTTCAGACGACTTCTGACGTACTCTTGA
```

```
   55        58
CysGlyGlyAlaStopXbaI
TGTGGTGGTGCCTAAT
ACACCACCACGGATTAGATC
```

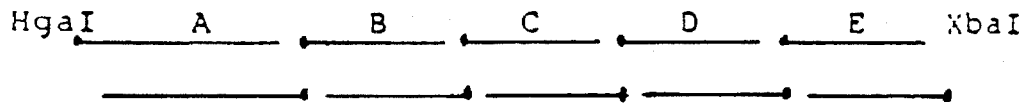

FIG. 1

```
      3       .5              10                  15
   AspPheCysLeuGluProProTyrThrGlyProCysLysAlaArgIle
AAAGAGATTTCTGTTTGGAACCTCCATACACTGGTCCATGTAAAGCTAGAATC
    CTAAAGACAAACCTTGGAGGTATGTGACCAGGTACATTTCGATCTTAG
                                 PflMI 20              25              30              35
   IleArgTyrPheTyrAsnAlaLysAlaGlyLeuCysGlnThrPheValTyrGly
ATCAGATACTTCTACAACGCCAAGGCTGGTTTGTGTCAAACTTTCGTTTACGGT
TAGTCTATGAAGATGTTGCGGTTCCGACCAAACACAGTTTGAAAGCAAATGCCA
                StyI 40              45              50
   GlyCysArgAlaLysSerAsnAsnPheLysSerAlaGluAspCysMetArgThr
GGCTGCAGAGCTAAGTCCAACAACTTCAAGTCTGCTGAAGACTGCATGAGAACT
CCGACGTCTCGATTCAGGTTGTTGAAGTTCAGACGACTTCTGACGTACTCTTGA
    PstI 55       58
CysGlyGlyAlaStop
TGTGGTGGTGCCTAAT
ACACCACCACGGATTAGATC
              XbaI
```

FIG. 5

```
                       1                   5
MetAlaGluArgLeuGluLysArgGluProAspPheCysLeuGluProPro-
NcoI
CATGGCTGAGAGATTGGAGAAGAGAGAGCCTGATTTCTGTTTGGAACCTCCA-
    CGACTCTTCAACCTCTTCTCTCGGACTAAAGACAAACCTTGGAGGT- 10              15              20              25
 TyrThrGlyProCysLysAlaArgIleIleArgTyrPheTyrAsnAlaGlu-
         AvaII
 TACACTGGTCCATGTAAAGCTAGAATCATCAGATACTTCTACAACGCCGAA-
 ATGTGACCAGGTACATTTCGATCTTAGTAGTCTATGAAGATGTTGCGGCTT- 30              35              40
 AlaGlyLeuCysGlnThrPheValTyrGlyGlyCysArgAlaGluArgAsn-

GCTGGTTTGTGTCAAACTTTCGTTTACGGTGGCTGCAGAGCTGAAAGAAAC-
 CGACCAAACACAGTTTGAAAGCAAATGCCACCGACGTCTCGACTTTCTTTG- 45              50              55        58
 AsnPheGluSerAlaGluAspCysMetArgThrCysGlyGlyAlaStop
                                              XbaI
 AACTTCGAATCTGCTGAAGACTGCATGAGAACTTGTGGTGGTGCCTAAT
 TTGAAGCTTAGACGACTTCTGACGTACTCTTGAACACCACCACGGATTAGATC
```

FIG. 10

```
      1                 5                 10                15
ArgProAspPheCysLeuGluProProTyrThrGlyProCysLysAlaArgIle
AGGCCTGATTTCTGTTTGGAACCTCCATACACTGGTCCATGTAAAGCTAGAATC
TCCGGACTAAAGACAAACCTTGGAGGTATGTGACCAGGTACATTTCGATCTTAG 20                25                30                35
IleArgTyrPheTyrAsnAlaLysAlaGlyLeuCysGlnThrPheValTyrGly
ATCAGATACTTCTACAACGCCAAGGCTGGTTTGTGTCAAACTTTCGTTTACGGT
TAGTCTATGAAGATGTTGCGGTTCCGACCAAACACAGTTTGAAAGCAAATGCCA 40                45                50
GlyCysArgAlaLysArgAsnAsnPheLysSerAlaGluAspCysMetArgThr
GGCTGCAGACGTAAGAGAAACAACTTCAAGTCTGCTGAAGACTGCATGAGAACT
CCGACGTCTCGATTCTCTTTGTTGAAGTTCAGACGACTTCTGACGTACTCTTGA 55       58
CysGlyGlyAlaStopXbaI
TGTGGTGGTGCCTAAT
ACACCACCACGGATTAGATC
```

FIG. 16

```
       1              5                 10                 15
ArgProAspPheCysLeuGluProProTyrThrGlyProCysLysAlaArgIle
AGGCCTGATTTCTGTTTGGAACCTCCATACACTGGTCCATGTAAAGCTAGAATC
TCCGGACTAAAGACAAACCTTGGAGGTATGTGACCAGGTACATTTCGATCTTAG 20             25                30                 35
IleArgTyrPheTyrAsnAlaLysAlaGlyLeuCysGlnThrPheValTyrGly
ATCAGATACTTCTACAACGCCAAGGCTGGTTTGTGTCAAACTTTCGTTTACGGT
TAGTCTATGAAGATGTTGCGGTTCCGACCAAACACAGTTTGAAAGCAAATGCCA 40             45                50
GlyCysArgAlaLysSerAsnAsnPheLysSerAlaGluAspCysMetArgThr
GGCTGCAGACGTAAGTCCAACAACTTCAAGTCTGCTGAAGACTGCATGAGAACT
CCGACGTCTCGATTCAGGTTGTTGAAGTTCAGACGACTTCTGACGTACTCTTGA 55       58
CysGlyGlyAlaStopXbaI
TGTGGTGGTGCCTAAT
ACACCACCACGGATTAGATC
```

FIG. 17

SEQUENCE LISTING ( 1 ) GENERAL INFORMATION:

( i i i ) NUMBER OF SEQUENCES: 83

( 2 ) INFORMATION FOR SEQ ID NO:1:

( i ) SEQUENCE CHARACTERISTICS:
      ( A ) LENGTH: 58 amino acids
      ( B ) TYPE: amino acid
      ( C ) STRANDEDNESS: single
      ( D ) TOPOLOGY: linear ( i i ) MOLECULE TYPE: protein ( v i ) ORIGINAL SOURCE:
      ( A ) ORGANISM: Bovine ( x i ) SEQUENCE DESCRIPTION: SEQ ID NO:1:

```
Arg Pro Asp Phe Cys Leu Glu Pro Pro Tyr Thr Gly Pro Cys Lys Ala
 1               5                   1 0                 1 5
```

```
        Arg   Ile   Ile   Arg   Tyr   Phe   Tyr   Asn   Ala   Lys   Ala   Gly   Leu   Cys   Gln   Thr
                          20                              25                              30

Phe   Val   Tyr   Gly   Gly   Cys   Arg   Ala   Lys   Arg   Asn   Asn   Phe   Lys   Ser   Ala
                          35                              40                              45

Glu   Asp   Cys   Met   Arg   Thr   Cys   Gly   Gly   Ala
                    50                              55
```

( 2 ) INFORMATION FOR SEQ ID NO:2:

( i ) SEQUENCE CHARACTERISTICS:
        ( A ) LENGTH: 57 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
        Xaa   Asp   Phe   Cys   Leu   Glu   Pro   Pro   Tyr   Thr   Xaa   Xaa   Xaa   Xaa   Xaa   Xaa
        1                       5                             10                              15

Xaa   Xaa   Arg   Tyr   Phe   Tyr   Asn   Ala   Lys   Ala   Gly   Leu   Cys   Gln   Thr   Phe
                          20                              25                              30

Val   Tyr   Gly   Gly   Xaa   Arg   Ala   Xaa   Xaa   Asn   Asn   Phe   Lys   Ser   Ala   Glu
                    35                              40                              45

Asp   Cys   Met   Arg   Thr   Cys   Gly   Gly   Ala
                    50                              55
```

( 2 ) INFORMATION FOR SEQ ID NO:3:

( i ) SEQUENCE CHARACTERISTICS:
        ( A ) LENGTH: 57 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
        Xaa   Asp   Phe   Cys   Leu   Glu   Pro   Pro   Tyr   Thr   Gly   Pro   Cys   Xaa   Xaa   Xaa
        1                       5                             10                              15

Xaa   Xaa   Arg   Tyr   Phe   Tyr   Asn   Ala   Lys   Ala   Gly   Leu   Cys   Gln   Thr   Phe
                          20                              25                              30

Val   Tyr   Gly   Gly   Cys   Arg   Ala   Xaa   Xaa   Asn   Asn   Phe   Lys   Ser   Ala   Glu
                    35                              40                              45

Asp   Cys   Met   Arg   Thr   Cys   Gly   Gly   Ala
                    50                              55
```

( 2 ) INFORMATION FOR SEQ ID NO:4:

( i ) SEQUENCE CHARACTERISTICS:
        ( A ) LENGTH: 57 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
        Xaa   Asp   Phe   Cys   Leu   Glu   Pro   Pro   Tyr   Thr   Gly   Pro   Cys   Lys   Xaa   Xaa
        1                       5                             10                              15

Xaa   Xaa   Arg   Tyr   Phe   Tyr   Asn   Ala   Lys   Ala   Gly   Leu   Cys   Gln   Thr   Phe
                          20                              25                              30

Val   Tyr   Gly   Gly   Cys   Arg   Ala   Xaa   Xaa   Asn   Asn   Phe   Lys   Ser   Ala   Glu
                    35                              40                              45
```

```
            Asp  Cys  Met  Arg  Thr  Cys  Gly  Gly  Ala
                 50                  55
```

( 2 ) INFORMATION FOR SEQ ID NO:5:

( i ) SEQUENCE CHARACTERISTICS:
        ( A ) LENGTH: 56 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
Asp  Phe  Cys  Leu  Glu  Pro  Pro  Tyr  Thr  Gly  Pro  Cys  Lys  Ala  Ala  Ile
1                   5                        10                       15

Ile  Arg  Tyr  Phe  Tyr  Asn  Ala  Lys  Ala  Gly  Leu  Cys  Gln  Thr  Phe  Val
               20                       25                       30

Tyr  Gly  Gly  Cys  Arg  Ala  Lys  Ser  Asn  Asn  Phe  Lys  Ser  Ala  Glu  Asp
          35                       40                       45

Cys  Met  Arg  Thr  Cys  Gly  Gly  Ala
     50                  55
```

( 2 ) INFORMATION FOR SEQ ID NO:6:

( i ) SEQUENCE CHARACTERISTICS:
        ( A ) LENGTH: 56 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Asp  Phe  Cys  Leu  Glu  Pro  Pro  Tyr  Thr  Gly  Pro  Cys  Lys  Ala  Ala  Ile
1                   5                        10                       15

Glu  Arg  Tyr  Phe  Tyr  Asn  Ala  Lys  Ala  Gly  Leu  Cys  Gln  Thr  Phe  Val
               20                       25                       30

Tyr  Gly  Gly  Cys  Arg  Ala  Lys  Ser  Asn  Asn  Phe  Lys  Ser  Ala  Glu  Asp
          35                       40                       45

Cys  Met  Arg  Thr  Cys  Gly  Gly  Ala
     50                  55
```

( 2 ) INFORMATION FOR SEQ ID NO:7:

( i ) SEQUENCE CHARACTERISTICS:
        ( A ) LENGTH: 56 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Asp  Phe  Cys  Leu  Glu  Pro  Pro  Tyr  Thr  Gly  Pro  Cys  Arg  Ala  Ala  Ile
1                   5                        10                       15

Ile  Arg  Tyr  Phe  Tyr  Asn  Ala  Lys  Ala  Gly  Leu  Cys  Gln  Thr  Phe  Val
               20                       25                       30

Tyr  Gly  Gly  Cys  Arg  Ala  Lys  Ser  Asn  Asn  Phe  Lys  Ser  Ala  Glu  Asp
          35                       40                       45

Cys  Met  Arg  Thr  Cys  Gly  Gly  Ala
     50                  55
```

( 2 ) INFORMATION FOR SEQ ID NO:8:

( i ) SEQUENCE CHARACTERISTICS:
      ( A ) LENGTH: 56 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:8:

```
Asp Phe Cys Leu Glu Pro Pro Tyr Thr Gly Pro Cys Lys Ala Ala Ile
 1               5                  10                  15
Ile Arg Tyr Phe Tyr Asn Ala Lys Ala Gly Leu Cys Gln Thr Phe Val
            20                  25                  30
Tyr Gly Gly Cys Arg Ala Lys Arg Asn Asn Phe Lys Ser Ala Glu Asp
        35                  40                  45
Cys Met Arg Thr Cys Gly Gly Ala
    50                  55
```

( 2 ) INFORMATION FOR SEQ ID NO:9:

( i ) SEQUENCE CHARACTERISTICS:
      ( A ) LENGTH: 56 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:9:

```
Asp Phe Cys Leu Glu Pro Pro Tyr Thr Gly Pro Cys Lys Ala Ala Ile
 1               5                  10                  15
Glu Arg Tyr Phe Tyr Asn Ala Lys Ala Gly Leu Cys Gln Thr Phe Val
            20                  25                  30
Tyr Gly Gly Cys Arg Ala Lys Arg Asn Asn Phe Lys Ser Ala Glu Asp
        35                  40                  45
Cys Met Arg Thr Cys Gly Gly Ala
    50                  55
```

( 2 ) INFORMATION FOR SEQ ID NO:10:

( i ) SEQUENCE CHARACTERISTICS:
      ( A ) LENGTH: 56 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:10:

```
Asp Phe Cys Leu Glu Pro Pro Tyr Thr Gly Pro Cys Arg Ala Ala Ile
 1               5                  10                  15
Ile Arg Tyr Phe Tyr Asn Ala Lys Ala Gly Leu Cys Gln Thr Phe Val
            20                  25                  30
Tyr Gly Gly Cys Arg Ala Lys Arg Asn Asn Phe Lys Ser Ala Glu Asp
        35                  40                  45
Cys Met Arg Thr Cys Gly Gly Ala
    50                  55
```

( 2 ) INFORMATION FOR SEQ ID NO:11:

( i ) SEQUENCE CHARACTERISTICS:
      ( A ) LENGTH: 58 amino acids
      ( B ) TYPE: amino acid (C) STRANDEDNESS: single
(D) TOPOLOGY: linear (ii) MOLECULE TYPE: protein (xi) SEQUENCE DESCRIPTION: SEQ ID NO:11:

| Arg | Pro | Asp | Phe | Cys | Leu | Glu | Pro | Pro | Tyr | Thr | Gly | Pro | Cys | Lys | Ala |
|---|---|---|---|---|---|---|---|---|---|---|---|---|---|---|---|
| 1 | | | | 5 | | | | | 10 | | | | | 15 | |
| Ala | Ile | Ile | Arg | Tyr | Phe | Tyr | Asn | Ala | Lys | Ala | Gly | Leu | Cys | Gln | Thr |
| | | | 20 | | | | | 25 | | | | | | 30 | |
| Phe | Val | Tyr | Gly | Gly | Cys | Arg | Ala | Lys | Ser | Asn | Asn | Phe | Lys | Ser | Ala |
| | | 35 | | | | | 40 | | | | | 45 | | | |
| Glu | Asp | Cys | Met | Arg | Thr | Cys | Gly | Gly | Ala | | | | | | |
| | | 50 | | | | 55 | | | | | | | | | |

(2) INFORMATION FOR SEQ ID NO:12:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:12:

| Arg | Pro | Asp | Phe | Cys | Leu | Glu | Pro | Pro | Tyr | Thr | Gly | Pro | Cys | Arg | Ala |
|---|---|---|---|---|---|---|---|---|---|---|---|---|---|---|---|
| 1 | | | | 5 | | | | | 10 | | | | | 15 | |
| Ala | Ile | Ile | Arg | Tyr | Phe | Tyr | Asn | Ala | Lys | Ala | Gly | Leu | Cys | Gln | Thr |
| | | | 20 | | | | | 25 | | | | | | 30 | |
| Phe | Val | Tyr | Gly | Gly | Cys | Arg | Ala | Lys | Ser | Asn | Asn | Phe | Lys | Ser | Ala |
| | | 35 | | | | | 40 | | | | | 45 | | | |
| Glu | Asp | Cys | Met | Arg | Thr | Cys | Gly | Gly | Ala | | | | | | |
| | | 50 | | | | 55 | | | | | | | | | |

(2) INFORMATION FOR SEQ ID NO:13:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:13:

| Arg | Pro | Asp | Phe | Cys | Leu | Glu | Pro | Pro | Tyr | Thr | Gly | Pro | Cys | Lys | Ala |
|---|---|---|---|---|---|---|---|---|---|---|---|---|---|---|---|
| 1 | | | | 5 | | | | | 10 | | | | | 15 | |
| Ala | Ile | Ile | Arg | Tyr | Phe | Tyr | Asn | Ala | Lys | Ala | Gly | Leu | Cys | Gln | Thr |
| | | | 20 | | | | | 25 | | | | | | 30 | |
| Phe | Val | Tyr | Gly | Gly | Cys | Arg | Ala | Lys | Arg | Asn | Asn | Phe | Lys | Ser | Ala |
| | | 35 | | | | | 40 | | | | | 45 | | | |
| Glu | Asp | Cys | Met | Arg | Thr | Cys | Gly | Gly | Ala | | | | | | |
| | | 50 | | | | 55 | | | | | | | | | |

(2) INFORMATION FOR SEQ ID NO:14:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: protein ( x i ) SEQUENCE DESCRIPTION: SEQ ID NO:14:

Arg Pro Asp Phe Cys Leu Glu Pro Pro Tyr Thr Gly Pro Cys Lys Ala
1               5                   10                  15

Ala Ile Glu Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

( 2 ) INFORMATION FOR SEQ ID NO:15:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:15:

Arg Pro Asp Phe Cys Leu Glu Pro Pro Tyr Thr Gly Pro Cys Arg Ala
1               5                   10                  15

Ala Ile Glu Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

( 2 ) INFORMATION FOR SEQ ID NO:16:

( i ) SEQUENCE CHARACTERISTICS:
        ( A ) LENGTH: 57 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:16:

Xaa Asp Phe Cys Leu Glu Pro Pro Xaa Thr Gly Pro Cys Lys Ala Arg
1               5                   10                  15

Ile Ile Xaa Tyr Phe Tyr Xaa Ala Xaa Ala Gly Leu Cys Xaa Thr Phe
            20                  25                  30

Val Tyr Gly Gly Cys Arg Xaa Xaa Xaa Asn Xaa Phe Xaa Ser Ala Glu
        35                  40                  45

Asp Cys Met Xaa Thr Cys Gly Gly Ala
    50                  55

( 2 ) INFORMATION FOR SEQ ID NO:17:

( i ) SEQUENCE CHARACTERISTICS:
        ( A ) LENGTH: 57 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:17:

Xaa Asp Phe Cys Leu Glu Pro Pro Xaa Thr Gly Pro Cys Xaa Xaa Xaa
1               5                   10                  15

```
    Xaa  Xaa  Xaa  Tyr  Phe  Tyr  Xaa  Ala  Xaa  Ala  Gly  Leu  Cys  Xaa  Thr  Phe
                   20                      25                           30

Xaa  Tyr  Xaa  Gly  Cys  Xaa  Xaa  Xaa  Xaa  Asn  Xaa  Phe  Xaa  Ser  Ala  Glu
              35                      40                      45

Asp  Cys  Met  Xaa  Thr  Cys  Gly  Gly  Ala
              50                   55
```

( 2 ) INFORMATION FOR SEQ ID NO:18:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

AAAGAGATTT CTGTTTGGAA CCTCCATACA CTGGTCC                                  37

( 2 ) INFORMATION FOR SEQ ID NO:19:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

TTACATGGAC CAGTGTATGG AGGTTCCAAA CAGAAACT                               38

( 2 ) INFORMATION FOR SEQ ID NO:20:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

ATGTAAAGCT AGAATCATCA GATACTTCTA CAACG                                    35

( 2 ) INFORMATION FOR SEQ ID NO:21:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

TTCGGCGTTG TAGAAGTATC TGATGATTCT AGCT                                     34

( 2 ) INFORMATION FOR SEQ ID NO:22:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

CCAAGGCTGG TTTGTGTCAA ACTTTCGTTT ACGGTGGCT 39

( 2 ) INFORMATION FOR SEQ ID NO:23:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

CTCTGCAGCC ACCGTAAACG AAAGTTTGAC ACAAACCAGC 40

( 2 ) INFORMATION FOR SEQ ID NO:24:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

GCAGAGCTAA GTCCAACAAC TTCAAGT 27

( 2 ) INFORMATION FOR SEQ ID NO:25:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

AGCAGACTTG AAGTTGTTGG ACTTAG 26

( 2 ) INFORMATION FOR SEQ ID NO:26:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

CTGCTGAAGA CTGCATGAGA ACTTGTGGTG GTGCCTAAT 39

( 2 ) INFORMATION FOR SEQ ID NO:27:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

CTAGATTAGG CACCACCACA AGTTCTCATG CAGTCTTC 38

( 2 ) INFORMATION FOR SEQ ID NO:28:

( i ) SEQUENCE CHARACTERISTICS:
        ( A ) LENGTH: 177 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 6..173

( x i ) SEQUENCE DESCRIPTION: SEQ ID NO:28:

```
AAAGA GAT TTC TGT TTG GAA CCT CCA TAC ACT GGT CCA TGT AAA GCT         47
      Asp Phe Cys Leu Glu Pro Pro Tyr Thr Gly Pro Cys Lys Ala
       1               5                  10

AGA ATC ATC AGA TAC TTC TAC AAC GCC AAG GCT GGT TTG TGT CAA ACT        95
Arg Ile Ile Arg Tyr Phe Tyr Asn Ala Lys Ala Gly Leu Cys Gln Thr
 15              20                  25                  30

TTC GTT TAC GGT GGC TGC AGA GCT AAG AGA AAC AAC TTC AAG TCT GCT       143
Phe Val Tyr Gly Gly Cys Arg Ala Lys Arg Asn Asn Phe Lys Ser Ala
                 35                  40                  45

GAA GAC TGC ATG AGA ACT TGT GGT GGT GCC TAAT                          177
Glu Asp Cys Met Arg Thr Cys Gly Gly Ala
                 50                  55
```

( 2 ) INFORMATION FOR SEQ ID NO:29:

( i ) SEQUENCE CHARACTERISTICS:
        ( A ) LENGTH: 56 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

```
Asp Phe Cys Leu Glu Pro Pro Tyr Thr Gly Pro Cys Lys Ala Arg Ile
 1               5                  10                  15

Ile Arg Tyr Phe Tyr Asn Ala Lys Ala Gly Leu Cys Gln Thr Phe Val
             20                  25                  30

Tyr Gly Gly Cys Arg Ala Lys Arg Asn Asn Phe Lys Ser Ala Glu Asp
             35                  40                  45

Cys Met Arg Thr Cys Gly Gly Ala
             50                  55
```

( 2 ) INFORMATION FOR SEQ ID NO:30:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:30:

```
Asp Phe Cys Leu Glu Pro Pro Tyr Thr Gly Pro Cys Lys Ala Arg Ile
 1               5                  10                  15

Ile Arg
```

( 2 ) INFORMATION FOR SEQ ID NO:31:

( i ) SEQUENCE CHARACTERISTICS:
        ( A ) LENGTH: 27 base pairs
        ( B ) TYPE: nucleic acid

```
          ( C ) STRANDEDNESS: single
          ( D ) TOPOLOGY: linear ( i i ) MOLECULE TYPE: cDNA ( x i ) SEQUENCE DESCRIPTION: SEQ ID NO:31:

GCAGAGCTAA GTCCAACAAC TTCAAGT                                                  27

( 2 ) INFORMATION FOR SEQ ID NO:32:

( i ) SEQUENCE CHARACTERISTICS:
          ( A ) LENGTH: 26 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:32:

AGCAGACTTG AAGTTGTTGG ACTTAG                                                   26

( 2 ) INFORMATION FOR SEQ ID NO:33:

( i ) SEQUENCE CHARACTERISTICS:
          ( A ) LENGTH: 177 base pairs
          ( B ) TYPE: nucleic acid
          ( C ) STRANDEDNESS: single
          ( D ) TOPOLOGY: linear ( i i ) MOLECULE TYPE: cDNA ( i x ) FEATURE:
          ( A ) NAME/KEY: CDS
          ( B ) LOCATION: 6..173

( x i ) SEQUENCE DESCRIPTION: SEQ ID NO:33:
```

```
AAAGA GAT TTC TGT TTG GAA CCT CCA TAC ACT GGT CCA TGT AAA GCT          47
      Asp Phe Cys Leu Glu Pro Pro Tyr Thr Gly Pro Cys Lys Ala
       1               5                   10

AGA ATC ATC AGA TAC TTC TAC AAC GCC AAG GCT GGT TTG TGT CAA ACT        95
Arg Ile Ile Arg Tyr Phe Tyr Asn Ala Lys Ala Gly Leu Cys Gln Thr
 15                  20                  25                  30

TTC GTT TAC GGT GGC TGC AGA GCT AAG TCC AAC AAC TTC AAG TCT GCT        143
Phe Val Tyr Gly Gly Cys Arg Ala Lys Ser Asn Asn Phe Lys Ser Ala
                 35                  40                  45

GAA GAC TGC ATG AGA ACT TGT GGT GGT GCC TAAT                           177
Glu Asp Cys Met Arg Thr Cys Gly Gly Ala
                 50                  55
```

( 2 ) INFORMATION FOR SEQ ID NO:34:

( i ) SEQUENCE CHARACTERISTICS:
          ( A ) LENGTH: 56 amino acids
          ( B ) TYPE: amino acid
          ( D ) TOPOLOGY: linear ( i i ) MOLECULE TYPE: protein ( x i ) SEQUENCE DESCRIPTION: SEQ ID NO:34:

```
Asp Phe Cys Leu Glu Pro Pro Tyr Thr Gly Pro Cys Lys Ala Arg Ile
 1               5                  10                  15

Ile Arg Tyr Phe Tyr Asn Ala Lys Ala Gly Leu Cys Gln Thr Phe Val
                 20                  25                  30

Tyr Gly Gly Cys Arg Ala Lys Ser Asn Asn Phe Lys Ser Ala Glu Asp
             35                  40                  45

Cys Met Arg Thr Cys Gly Gly Ala
         50                  55
```

( 2 ) INFORMATION FOR SEQ ID NO:35:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:35:

```
Asp Phe Cys Leu Glu Pro Pro Tyr Thr Gly Pro Cys Lys Ala Arg Ile
 1               5                  10                  15

Ile Arg Tyr Phe
            20
```

( 2 ) INFORMATION FOR SEQ ID NO:36:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:36:

CTGGTCCATG TAAAGCTGCT ATCATCAGAT ACTTCTACAA CGC        43

( 2 ) INFORMATION FOR SEQ ID NO:37:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

CTTGGCGTTG TAGAAGTATC TGATGATAGC AGCTTTACAT GGACCAGTGT        50

( 2 ) INFORMATION FOR SEQ ID NO:38:

( i ) SEQUENCE CHARACTERISTICS:
        ( A ) LENGTH: 178 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..174

( x i ) SEQUENCE DESCRIPTION: SEQ ID NO:38:

```
AGG CCT GAT TTC TGT TTG GAA CCT CCA TAC ACT GGT CCA TGT AAA GCT    48
Arg Pro Asp Phe Cys Leu Glu Pro Pro Tyr Thr Gly Pro Cys Lys Ala
 1               5                  10                  15

AGA ATC ATC AGA TAC TTC TAC AAC GCC AAG GCT GGT TTG TGT CAA ACT    96
Arg Ile Ile Arg Tyr Phe Tyr Asn Ala Lys Ala Gly Leu Cys Gln Thr
            20                  25                  30

TTC GTT TAC GGT GGC TGC AGA GCT AAG AGA AAC AAC TTC AAG TCT GCT   144
Phe Val Tyr Gly Gly Cys Arg Ala Lys Arg Asn Asn Phe Lys Ser Ala
        35                  40                  45

GAA GAC TGC ATG AGA ACT TGT GGT GGT GCC TAAT                      178
```

```
Glu  Asp  Cys  Met  Arg  Thr  Cys  Gly  Gly  Ala
     50                  55
```

( 2 ) INFORMATION FOR SEQ ID NO:39:

( i ) SEQUENCE CHARACTERISTICS:
       ( A ) LENGTH: 58 amino acids
       ( B ) TYPE: amino acid
       ( D ) TOPOLOGY: linear ( i i ) MOLECULE TYPE: protein ( x i ) SEQUENCE DESCRIPTION: SEQ ID NO:39:

```
Arg  Pro  Asp  Phe  Cys  Leu  Glu  Pro  Pro  Tyr  Thr  Gly  Pro  Cys  Lys  Ala
 1                   5                        10                       15

Arg  Ile  Ile  Arg  Tyr  Phe  Tyr  Asn  Ala  Lys  Ala  Gly  Leu  Cys  Gln  Thr
               20                       25                        30

Phe  Val  Tyr  Gly  Gly  Cys  Arg  Ala  Lys  Arg  Asn  Asn  Phe  Lys  Ser  Ala
          35                       40                        45

Glu  Asp  Cys  Met  Arg  Thr  Cys  Gly  Gly  Ala
     50                  55
```

( 2 ) INFORMATION FOR SEQ ID NO:40:

( i ) SEQUENCE CHARACTERISTICS:
       ( A ) LENGTH: 178 base pairs
       ( B ) TYPE: nucleic acid
       ( C ) STRANDEDNESS: single
       ( D ) TOPOLOGY: linear ( i i ) MOLECULE TYPE: cDNA ( i x ) FEATURE:
       ( A ) NAME/KEY: CDS
       ( B ) LOCATION: 1..174

( x i ) SEQUENCE DESCRIPTION: SEQ ID NO:40:

```
AGG  CCT  GAT  TTC  TGT  TTG  GAA  CCT  CCA  TAC  ACT  GGT  CCA  TGT  AAA  GCT      48
Arg  Pro  Asp  Phe  Cys  Leu  Glu  Pro  Pro  Tyr  Thr  Gly  Pro  Cys  Lys  Ala
 1                   5                        10                       15

AGA  ATC  ATC  AGA  TAC  TTC  TAC  AAC  GCC  AAG  GCT  GGT  TTG  TGT  CAA  ACT      96
Arg  Ile  Ile  Arg  Tyr  Phe  Tyr  Asn  Ala  Lys  Ala  Gly  Leu  Cys  Gln  Thr
               20                       25                        30

TTC  GTT  TAC  GGT  GGC  TGC  AGA  GCT  AAG  TCC  AAC  AAC  TTC  AAG  TCT  GCT     144
Phe  Val  Tyr  Gly  Gly  Cys  Arg  Ala  Lys  Ser  Asn  Asn  Phe  Lys  Ser  Ala
          35                       40                        45

GAA  GAC  TGC  ATG  AGA  ACT  TGT  GGT  GGT  GCC  TAAT                             178
Glu  Asp  Cys  Met  Arg  Thr  Cys  Gly  Gly  Ala
     50                  55
```

( 2 ) INFORMATION FOR SEQ ID NO:41:

( i ) SEQUENCE CHARACTERISTICS:
       ( A ) LENGTH: 58 amino acids
       ( B ) TYPE: amino acid
       ( D ) TOPOLOGY: linear ( i i ) MOLECULE TYPE: protein ( x i ) SEQUENCE DESCRIPTION: SEQ ID NO:41:

```
Arg  Pro  Asp  Phe  Cys  Leu  Glu  Pro  Pro  Tyr  Thr  Gly  Pro  Cys  Lys  Ala
 1                   5                        10                       15

Arg  Ile  Ile  Arg  Tyr  Phe  Tyr  Asn  Ala  Lys  Ala  Gly  Leu  Cys  Gln  Thr
               20                       25                        30

Phe  Val  Tyr  Gly  Gly  Cys  Arg  Ala  Lys  Ser  Asn  Asn  Phe  Lys  Ser  Ala
          35                       40                        45
```

Glu Asp Cys Met Arg Thr Cys Gly Gly Ala
 50                     55

( 2 ) INFORMATION FOR SEQ ID NO:42:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:42:

CTGGTCCATG TAAAGCTGCT ATCGAAAGAT ACTTCTACAA CGC     43

( 2 ) INFORMATION FOR SEQ ID NO:43:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:43:

CTTGGCGTTG TAGAAGTATC TTTCGATAGC AGCTTTACAT GGACCAGTGT     50

( 2 ) INFORMATION FOR SEQ ID NO:44:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:44:

CTGGTCCATG TAGAGCTGCT ATCATCAGAT ACTTCTACAA CGC     43

( 2 ) INFORMATION FOR SEQ ID NO:45:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:45:

CTTGGCGTTG TAGAAGTATC TGATGATAGC AGCTCTACAT GGACCAGTGT     50

( 2 ) INFORMATION FOR SEQ ID NO:46:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:46:

CATGGCTGAG AGATTGGAGA AGAGAGAGCC TGATTTCTGT TTGGAACCTC CATACACTGG     60
TCC     63

( 2 ) INFORMATION FOR SEQ ID NO:47:

( i ) SEQUENCE CHARACTERISTICS:
    ( A ) LENGTH: 65 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:47:

TTACATGGAC CAGTGTATGG AGGTTCCAAA CAGAAATCAG GCTCTCTCTT CTCCAATCTC    60

TCAGC    65

( 2 ) INFORMATION FOR SEQ ID NO:48:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:48:

CCGAAGCTGG TTTGTGTCAA ACTTTCGTTT ACGGTGGCT    39

( 2 ) INFORMATION FOR SEQ ID NO:49:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:49:

CTCTGCAGCC ACCGTAAACG AAAGTTTGAC ACAAACCAGC    40

( 2 ) INFORMATION FOR SEQ ID NO:50:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:50:

GCAGAGCTGA AAGAAACAAC TTCGAAT    27

( 2 ) INFORMATION FOR SEQ ID NO:51:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:51:

AGCAGATTCG AAGTTGTTTC TTTCAG    26

( 2 ) INFORMATION FOR SEQ ID NO:52:

( i ) SEQUENCE CHARACTERISTICS:
    ( A ) LENGTH: 418 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: sig_peptide
    ( B ) LOCATION: 77..235

( i x ) FEATURE:
    ( A ) NAME/KEY: mat_peptide
    ( B ) LOCATION: 236..409

( i x ) FEATURE:
    ( A ) NAME/KEY: CDS
    ( B ) LOCATION: 77..409

( x i ) SEQUENCE DESCRIPTION: SEQ ID NO:52:

```
GAATTCCATT  CAAGAATAGT  TCAAACAAGA  AGATTACAAA  CTATCAATTT  CATACACAAT        60

ATAAACGACC  AAAAGA ATG AAG GCT GTT TTC TTG GTT TTG TCC TTG ATC                109
                  Met Lys Ala Val Phe Leu Val Leu Ser Leu Ile
                  -53         -50                     -45

GGA TTC TGC TGG GCC CAA CCA GTC ACT GGC GAT GAA TCA TCT GTT GAG               157
Gly Phe Cys Trp Ala Gln Pro Val Thr Gly Asp Glu Ser Ser Val Glu
        -40             -35                     -30

ATT CCG GAA GAG TCT CTG ATC ATC GCT GAA AAC ACC ACT TTG GCT AAC               205
Ile Pro Glu Glu Ser Leu Ile Ile Ala Glu Asn Thr Thr Leu Ala Asn
    -25                 -20                     -15

GTC GCC ATG GCT GAG AGA TTG GAG AAG AGA GAG CCT GAT TTC TGT TTG               253
Val Ala Met Ala Glu Arg Leu Glu Lys Arg Glu Pro Asp Phe Cys Leu
-10                      -5                   1                 5

GAA CCT CCA TAC ACT GGT CCA TGT AAA GCT AGA ATC ATC AGA TAC TTC               301
Glu Pro Pro Tyr Thr Gly Pro Cys Lys Ala Arg Ile Ile Arg Tyr Phe
                10              15                  20

TAC AAC GCC GAA GCT GGT TTG TGT CAA ACT TTC GTT TAC GGT GGC TGC               349
Tyr Asn Ala Glu Ala Gly Leu Cys Gln Thr Phe Val Tyr Gly Gly Cys
            25              30                  35

AGA GCT GAA AGA AAC AAC TTC GAA TCT GCT GAA GAC TGC ATG AGA ACT               397
Arg Ala Glu Arg Asn Asn Phe Glu Ser Ala Glu Asp Cys Met Arg Thr
        40              45                  50

TGT GGT GGT GCC TAATCTAGA                                                     418
Cys Gly Gly Ala
55
```

( 2 ) INFORMATION FOR SEQ ID NO:53:

( i ) SEQUENCE CHARACTERISTICS:
        ( A ) LENGTH: 111 amino acids
        ( B ) TYPE: amino acid
        ( D ) TOPOLOGY: linear ( i i ) MOLECULE TYPE: protein ( x i ) SEQUENCE DESCRIPTION: SEQ ID NO:53:

```
Met Lys Ala Val Phe Leu Val Leu Ser Leu Ile Gly Phe Cys Trp Ala
-53         -50                 -45                 -40

Gln Pro Val Thr Gly Asp Glu Ser Ser Val Glu Ile Pro Glu Glu Ser
        -35                 -30              -25

Leu Ile Ile Ala Glu Asn Thr Thr Leu Ala Asn Val Ala Met Ala Glu
    -20                 -15                 -10

Arg Leu Glu Lys Arg Glu Pro Asp Phe Cys Leu Glu Pro Pro Tyr Thr
-5                    1                 5                    10
```

```
Gly Pro Cys Lys Ala Arg Ile Ile Arg Tyr Phe Tyr Asn Ala Glu Ala
         15                  20                  25

Gly Leu Cys Gln Thr Phe Val Tyr Gly Gly Cys Arg Ala Glu Arg Asn
         30                  35                  40

Asn Phe Glu Ser Ala Glu Asp Cys Met Arg Thr Cys Gly Gly Ala
         45                  50                  55
```

( 2 ) INFORMATION FOR SEQ ID NO:54:

( i ) SEQUENCE CHARACTERISTICS:
        ( A ) LENGTH: 418 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 77..409

( i x ) FEATURE:
        ( A ) NAME/KEY: sig_peptide
        ( B ) LOCATION: 77..235

( i x ) FEATURE:
        ( A ) NAME/KEY: mat_peptide
        ( B ) LOCATION: 236..409

( x i ) SEQUENCE DESCRIPTION: SEQ ID NO:54:

```
GAATTCCATT CAAGAATAGT TCAAACAAGA AGATTACAAA CTATCAATTT CATACACAAT         60

ATAAACGACC AAAAGA ATG AAG GCT GTT TTC TTG GTT TTG TCC TTG ATC           109
               Met Lys Ala Val Phe Leu Val Leu Ser Leu Ile
               -53         -50                     -45

GGA TTC TGC TGG GCC CAA CCA GTC ACT GGC GAT GAA TCA TCT GTT GAG         157
Gly Phe Cys Trp Ala Gln Pro Val Thr Gly Asp Glu Ser Ser Val Glu
        -40             -35                 -30

ATT CCG GAA GAG TCT CTG ATC ATC GCT GAA AAC ACC ACT TTG GCT AAC         205
Ile Pro Glu Glu Ser Leu Ile Ile Ala Glu Asn Thr Thr Leu Ala Asn
    -25             -20                 -15

GTC GCC ATG GCT GAG AGA TTG GAG AAG AGA GAG CCT GAT TTC TGT TTG         253
Val Ala Met Ala Glu Arg Leu Glu Lys Arg Glu Pro Asp Phe Cys Leu
-10              -5                   1              5

GAA CCT CCA TAC ACT GGT CCA TGT AAA GCT AGA ATC ATC AGA TAC TTC         301
Glu Pro Pro Tyr Thr Gly Pro Cys Lys Ala Arg Ile Ile Arg Tyr Phe
         10                  15                  20

TAC AAC GCC AAG GCT GGT TTG TGT CAA ACT TTC GTT TAC GGT GGC TGC         349
Tyr Asn Ala Lys Ala Gly Leu Cys Gln Thr Phe Val Tyr Gly Gly Cys
         25                  30                  35

AGA GCT AAG GAA AAC AAC TTC GAA TCT GCT GAA GAC TGC ATG AGA ACT         397
Arg Ala Lys Glu Asn Asn Phe Glu Ser Ala Glu Asp Cys Met Arg Thr
         40                  45                  50

TGT GGT GGT GCC TAATCTAGA                                               418
Cys Gly Gly Ala
 55
```

( 2 ) INFORMATION FOR SEQ ID NO:55:

( i ) SEQUENCE CHARACTERISTICS:
        ( A ) LENGTH: 111 amino acids
        ( B ) TYPE: amino acid
        ( D ) TOPOLOGY: linear ( i i ) MOLECULE TYPE: protein ( x i ) SEQUENCE DESCRIPTION: SEQ ID NO:55:

```
Met  Lys  Ala  Val  Phe  Leu  Val  Leu  Ser  Leu  Ile  Gly  Phe  Cys  Trp  Ala
-53            -50                      -45                      -40

Gln  Pro  Val  Thr  Gly  Asp  Glu  Ser  Ser  Val  Glu  Ile  Pro  Glu  Glu  Ser
          -35                      -30                      -25

Leu  Ile  Ile  Ala  Glu  Asn  Thr  Thr  Leu  Ala  Asn  Val  Ala  Met  Ala  Glu
          -20                 -15                      -10

Arg  Leu  Glu  Lys  Arg  Glu  Pro  Asp  Phe  Cys  Leu  Glu  Pro  Pro  Tyr  Thr
-5                  1                   5                             10

Gly  Pro  Cys  Lys  Ala  Arg  Ile  Ile  Arg  Tyr  Phe  Tyr  Asn  Ala  Lys  Ala
               15                  20                       25

Gly  Leu  Cys  Gln  Thr  Phe  Val  Tyr  Gly  Gly  Cys  Arg  Ala  Lys  Glu  Asn
          30                      35                       40

Asn  Phe  Glu  Ser  Ala  Glu  Asp  Cys  Met  Arg  Thr  Cys  Gly  Gly  Ala
          45                      50                  55
```

(2) INFORMATION FOR SEQ ID NO:56:

(i) SEQUENCE CHARACTERISTICS:
    (A) LENGTH: 418 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 77..409

(ix) FEATURE:
    (A) NAME/KEY: sig_peptide
    (B) LOCATION: 77..235

(ix) FEATURE:
    (A) NAME/KEY: mat_peptide
    (B) LOCATION: 236..409

(xi) SEQUENCE DESCRIPTION: SEQ ID NO:56:

```
GAATTCCATT CAAGAATAGT TCAAACAAGA AGATTACAAA CTATCAATTT CATACACAAT              60

ATAAACGACC AAAAGA ATG AAG GCT GTT TTC TTG GTT TTG TCC TTG ATC                 109
               Met Lys Ala Val Phe Leu Val Leu Ser Leu Ile
               -53          -50                      -45

GGA TTC TGC TGG GCC CAA CCA GTC ACT GGC GAT GAA TCA TCT GTT GAG               157
Gly Phe Cys Trp Ala Gln Pro Val Thr Gly Asp Glu Ser Ser Val Glu
         -40                 -35                      -30

ATT CCG GAA GAG TCT CTG ATC ATC GCT GAA AAC ACC ACT TTG GCT AAC               205
Ile Pro Glu Glu Ser Leu Ile Ile Ala Glu Asn Thr Thr Leu Ala Asn
-25                  -20                      -15

GTC GCC ATG GCT GAG AGA TTG GAG AAG AGA AGG CCT GAT TTC TGT TTG               253
Val Ala Met Ala Glu Arg Leu Glu Lys Arg Arg Pro Asp Phe Cys Leu
-10                      -5                  1                   5

GAA CCT CCA TAC ACT GGT CCA TGT AAA GCT AGA ATC ATC AGA TAC TTC               301
Glu Pro Pro Tyr Thr Gly Pro Cys Lys Ala Arg Ile Ile Arg Tyr Phe
              10                  15                      20

TAC AAC GCC AAG GCT GGT TTG TGT CAA ACT TTC GTT TAC GGT GGC TGC               349
Tyr Asn Ala Lys Ala Gly Leu Cys Gln Thr Phe Val Tyr Gly Gly Cys
          25                      30                      35

AGA GCT AAG GAA AAC AAC TTC GAA TCT GCT GAA GAC TGC ATG AGA ACT               397
Arg Ala Lys Glu Asn Asn Phe Glu Ser Ala Glu Asp Cys Met Arg Thr
          40                      45                      50

TGT GGT GGT GCC TAATCTAGA                                                     418
Cys Gly Gly Ala
55
```

(2) INFORMATION FOR SEQ ID NO:57:

(i) SEQUENCE CHARACTERISTICS:
        (A) LENGTH: 111 amino acids
        (B) TYPE: amino acid
        (D) TOPOLOGY: linear (ii) MOLECULE TYPE: protein (xi) SEQUENCE DESCRIPTION: SEQ ID NO:57:

```
Met Lys Ala Val Phe Leu Val Leu Ser Leu Ile Gly Phe Cys Trp Ala
-53         -50                 -45                 -40
Gln Pro Val Thr Gly Asp Glu Ser Ser Val Glu Ile Pro Glu Glu Ser
        -35                 -30                 -25
Leu Ile Ile Ala Glu Asn Thr Thr Leu Ala Asn Val Ala Met Ala Glu
    -20                 -15                 -10
Arg Leu Glu Lys Arg Arg Pro Asp Phe Cys Leu Glu Pro Pro Tyr Thr
 -5              1           5                       10
Gly Pro Cys Lys Ala Arg Ile Ile Arg Tyr Phe Tyr Asn Ala Lys Ala
            15              20              25
Gly Leu Cys Gln Thr Phe Val Tyr Gly Gly Cys Arg Ala Lys Glu Asn
        30              35              40
Asn Phe Glu Ser Ala Glu Asp Cys Met Arg Thr Cys Gly Gly Ala
    45              50              55
```

(2) INFORMATION FOR SEQ ID NO:58:

(i) SEQUENCE CHARACTERISTICS:
        (A) LENGTH: 418 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 77..409

(ix) FEATURE:
        (A) NAME/KEY: sig_peptide
        (B) LOCATION: 77..235

(ix) FEATURE:
        (A) NAME/KEY: sig_peptide
        (B) LOCATION: 236..409

(xi) SEQUENCE DESCRIPTION: SEQ ID NO:58:

```
GAATTCCATT CAAGAATAGT TCAAACAAGA AGATTACAAA CTATCAATTT CATACACAAT      60

ATAAACGACC AAAAGA ATG AAG GCT GTT TTC TTG GTT TTG TCC TTG ATC        109
                  Met Lys Ala Val Phe Leu Val Leu Ser Leu Ile
                   1               5                      10

GGA TTC TGC TGG GCC CAA CCA GTC ACT GGC GAT GAA TCA TCT GTT GAG      157
Gly Phe Cys Trp Ala Gln Pro Val Thr Gly Asp Glu Ser Ser Val Glu
            15              20                  25

ATT CCG GAA GAG TCT CTG ATC ATC GCT GAA AAC ACC ACT TTG GCT AAC      205
Ile Pro Glu Glu Ser Leu Ile Ile Ala Glu Asn Thr Thr Leu Ala Asn
        30              35              40

GTC GCC ATG GCT GAG AGA TTG GAG AAG AGA AGG CCT GAT TTC TGT TTG      253
Val Ala Met Ala Glu Arg Leu Glu Lys Arg Arg Pro Asp Phe Cys Leu
    45              50              55

GAA CCT CCA TCT ACT GGT CCA TGT AAA GCT AGA ATC ATC AGA TAC TTC      301
Glu Pro Pro Ser Thr Gly Pro Cys Lys Ala Arg Ile Ile Arg Tyr Phe
 60              65                  70              75
```

| | | | | | | | | | | | | | | | | |
|---|---|---|---|---|---|---|---|---|---|---|---|---|---|---|---|---|
| TAC | GAC | GCC | ACT | GCT | GGT | TTG | TGT | GAA | ACT | TTC | GTT | TAC | GGT | GGC | TGC | 349 |
| Tyr | Asp | Ala | Thr | Ala | Gly | Leu | Cys | Glu | Thr | Phe | Val | Tyr | Gly | Gly | Cys | |
| | | | 80 | | | | | 85 | | | | | | 90 | | |
| AGA | GCT | AAC | AGA | AAC | AAC | TTC | AAG | TCT | GCT | GAA | GAC | TGC | ATG | GAA | ACT | 397 |
| Arg | Ala | Asn | Arg | Asn | Asn | Phe | Lys | Ser | Ala | Glu | Asp | Cys | Met | Glu | Thr | |
| | | | 95 | | | | | 100 | | | | | 105 | | | |
| TGT | GGT | GGT | GCC | TAATCTAGA | | | | | | | | | | | | 418 |
| Cys | Gly | Gly | Ala | | | | | | | | | | | | | |
| | | | 110 | | | | | | | | | | | | | |

( 2 ) INFORMATION FOR SEQ ID NO:59:

( i ) SEQUENCE CHARACTERISTICS:
        ( A ) LENGTH: 111 amino acids
        ( B ) TYPE: amino acid
        ( D ) TOPOLOGY: linear ( i i ) MOLECULE TYPE: protein ( x i ) SEQUENCE DESCRIPTION: SEQ ID NO:59:

| | | | | | | | | | | | | | | |
|---|---|---|---|---|---|---|---|---|---|---|---|---|---|---|
| Met | Lys | Ala | Val | Phe | Leu | Val | Leu | Ser | Leu | Ile | Gly | Phe | Cys | Trp | Ala |
| 1 | | | | 5 | | | | | 10 | | | | | 15 | |

| | | | | | | | | | | | | |
|---|---|---|---|---|---|---|---|---|---|---|---|---|
| Gln | Pro | Val | Thr | Gly | Asp | Glu | Ser | Ser | Val | Glu | Ile | Pro | Glu | Glu | Ser |
| | | | 20 | | | | | 25 | | | | | 30 | | |

| | | | | | | | | | | | | |
|---|---|---|---|---|---|---|---|---|---|---|---|---|
| Leu | Ile | Ile | Ala | Glu | Asn | Thr | Thr | Leu | Ala | Asn | Val | Ala | Met | Ala | Glu |
| | | | 35 | | | | | 40 | | | | | 45 | | |

| | | | | | | | | | | | | |
|---|---|---|---|---|---|---|---|---|---|---|---|---|
| Arg | Leu | Glu | Lys | Arg | Arg | Pro | Asp | Phe | Cys | Leu | Glu | Pro | Pro | Ser | Thr |
| | 50 | | | | | 55 | | | | | 60 | | | | |

| | | | | | | | | | | | | |
|---|---|---|---|---|---|---|---|---|---|---|---|---|
| Gly | Pro | Cys | Lys | Ala | Arg | Ile | Ile | Arg | Tyr | Phe | Tyr | Asp | Ala | Thr | Ala |
| 65 | | | | | 70 | | | | | 75 | | | | | 80 |

| | | | | | | | | | | | | |
|---|---|---|---|---|---|---|---|---|---|---|---|---|
| Gly | Leu | Cys | Glu | Thr | Phe | Val | Tyr | Gly | Gly | Cys | Arg | Ala | Asn | Arg | Asn |
| | | | 85 | | | | | 90 | | | | | 95 | | |

| | | | | | | | | | | | | |
|---|---|---|---|---|---|---|---|---|---|---|---|---|
| Asn | Phe | Lys | Ser | Ala | Glu | Asp | Cys | Met | Glu | Thr | Cys | Gly | Gly | Ala | |
| | | | 100 | | | | | 105 | | | | | 110 | | |

( 2 ) INFORMATION FOR SEQ ID NO:60:

( i ) SEQUENCE CHARACTERISTICS:
        ( A ) LENGTH: 418 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 77..409

( i x ) FEATURE:
        ( A ) NAME/KEY: sig_peptide
        ( B ) LOCATION: 77..235

( i x ) FEATURE:
        ( A ) NAME/KEY: mat_peptide
        ( B ) LOCATION: 236..409

( x i ) SEQUENCE DESCRIPTION: SEQ ID NO:60:

| | | | | | |
|---|---|---|---|---|---|
| GAATTCCATT | CAAGAATAGT | TCAAACAAGA | AGATTACAAA | CTATCAATTT | CATACACAAT | 60 |

| | | | | | | | | | | | | | |
|---|---|---|---|---|---|---|---|---|---|---|---|---|---|
| ATAAACGACC | AAAAGA | ATG | AAG | GCT | GTT | TTC | TTG | GTT | TTG | TCC | TTG | ATC | 109 |
| | | Met | Lys | Ala | Val | Phe | Leu | Val | Leu | Ser | Leu | Ile | |
| | | -53 | | -50 | | | | | -45 | | | | |

| | | | | | | | | | | | | | | | |
|---|---|---|---|---|---|---|---|---|---|---|---|---|---|---|---|
| GGA | TTC | TGC | TGG | GCC | CAA | CCA | GTC | ACT | GGC | GAT | GAA | TCA | TCT | GTT | GAG | 157 |
| Gly | Phe | Cys | Trp | Ala | Gln | Pro | Val | Thr | Gly | Asp | Glu | Ser | Ser | Val | Glu | |
| | | -40 | | | | -35 | | | | | -30 | | | | | |

| | | | | | | | | | | | | | | | |
|---|---|---|---|---|---|---|---|---|---|---|---|---|---|---|---|
| ATT | CCG | GAA | GAG | TCT | CTG | ATC | ATC | GCT | GAA | AAC | ACC | ACT | TTG | GCT | AAC | 205 |
| Ile | Pro | Glu | Glu | Ser | Leu | Ile | Ile | Ala | Glu | Asn | Thr | Thr | Leu | Ala | Asn | |
| | -25 | | | | | -20 | | | | | -15 | | | | | |
| GTC | GCC | ATG | GCT | GAG | AGA | TTG | GAG | AAG | AGA | AGG | CCT | GAT | TTC | TGT | TTG | 253 |
| Val | Ala | Met | Ala | Glu | Arg | Leu | Glu | Lys | Arg | Arg | Pro | Asp | Phe | Cys | Leu | |
| -10 | | | | | -5 | | | | | 1 | | | | 5 | | |
| GAA | CCT | CCA | TCT | ACT | GGT | CCA | TGT | AAA | GCT | AGA | ATC | ATC | TTG | TAC | TTC | 301 |
| Glu | Pro | Pro | Ser | Thr | Gly | Pro | Cys | Lys | Ala | Arg | Ile | Ile | Leu | Tyr | Phe | |
| | | | 10 | | | | | 15 | | | | | 20 | | | |
| TAC | AAC | GCC | AAG | GCT | GGT | TTG | TGT | CAA | ACT | TTC | GTT | TAC | GGT | GGC | TGC | 349 |
| Tyr | Asn | Ala | Lys | Ala | Gly | Leu | Cys | Gln | Thr | Phe | Val | Tyr | Gly | Gly | Cys | |
| | | 25 | | | | | 30 | | | | | 35 | | | | |
| AGA | GGT | AAC | GGT | AAC | CAA | TTC | TAC | TCT | GCT | GAA | GAC | TGC | ATG | AGA | ACT | 397 |
| Arg | Gly | Asn | Gly | Asn | Gln | Phe | Tyr | Ser | Ala | Glu | Asp | Cys | Met | Arg | Thr | |
| | 40 | | | | | 45 | | | | 50 | | | | | | |
| TGT | GGT | GGT | GCC | TAATCTAGA | | | | | | | | | | | | 418 |
| Cys | Gly | Gly | Ala | | | | | | | | | | | | | |
| 55 | | | | | | | | | | | | | | | | |

(2) INFORMATION FOR SEQ ID NO:61:

(i) SEQUENCE CHARACTERISTICS:
        (A) LENGTH: 111 amino acids
        (B) TYPE: amino acid
        (D) TOPOLOGY: linear (ii) MOLECULE TYPE: protein (xi) SEQUENCE DESCRIPTION: SEQ ID NO:61:

| | | | | | | | | | | | | | |
|---|---|---|---|---|---|---|---|---|---|---|---|---|---|
| Met | Lys | Ala | Val | Phe | Leu | Val | Leu | Ser | Leu | Ile | Gly | Phe | Cys | Trp | Ala |
| -53 | | | -50 | | | | | -45 | | | | | | -40 | |
| Gln | Pro | Val | Thr | Gly | Asp | Glu | Ser | Ser | Val | Glu | Ile | Pro | Glu | Glu | Ser |
| | | -35 | | | | | -30 | | | | | | -25 | | |
| Leu | Ile | Ile | Ala | Glu | Asn | Thr | Thr | Leu | Ala | Asn | Val | Ala | Met | Ala | Glu |
| | -20 | | | | | -15 | | | | | -10 | | | | |
| Arg | Leu | Glu | Lys | Arg | Arg | Pro | Asp | Phe | Cys | Leu | Glu | Pro | Pro | Ser | Thr |
| -5 | | | | | 1 | | | | 5 | | | | | 10 | |
| Gly | Pro | Cys | Lys | Ala | Arg | Ile | Ile | Leu | Tyr | Phe | Tyr | Asn | Ala | Lys | Ala |
| | | | | 15 | | | | 20 | | | | | 25 | | |
| Gly | Leu | Cys | Gln | Thr | Phe | Val | Tyr | Gly | Gly | Cys | Arg | Gly | Asn | Gly | Asn |
| | | 30 | | | | | 35 | | | | | 40 | | | |
| Gln | Phe | Tyr | Ser | Ala | Glu | Asp | Cys | Met | Arg | Thr | Cys | Gly | Gly | Ala | |
| | 45 | | | | | 50 | | | | 55 | | | | | |

(2) INFORMATION FOR SEQ ID NO:62:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:62:

```
CAAGGCTGGT TTGTGTCAAA CTTTCGTTTA CGGTGGCTGC AGAGCTAAGT CCAACAACTT        60
CGAATCTGCT GAAGACTGCA TGAGAACTTG TGGTGGTGCC TAATCTAGAG                  110
```

(2) INFORMATION FOR SEQ ID NO:63:

(i) SEQUENCE CHARACTERISTICS:
        (A) LENGTH: 110 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:63:

| | | | | | |
|---|---|---|---|---|---|
| TCGACTCTAG | ATTAGGCACC | ACCACAAGTT | CTCATGCAGT | CTTCAGCAGA | TTCGAAGTTG | 60 |
| TTGGACTTAG | CTCTGCAGCC | ACCGTAAACG | AAAGTTTGAC | ACAAACCAGC | | 110 |

(2) INFORMATION FOR SEQ ID NO:64:

(i) SEQUENCE CHARACTERISTICS:
(A) LENGTH: 508 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 77..499

(ix) FEATURE:
(A) NAME/KEY: sig_peptide
(B) LOCATION: 77..331

(ix) FEATURE:
(A) NAME/KEY: mat_peptide
(B) LOCATION: 332..499

(xi) SEQUENCE DESCRIPTION: SEQ ID NO:64:

```
GAATTCCATT  CAAGAATAGT  TCAAACAAGA  AGATTACAAA  CTATCAATTT  CATACACAAT              60

ATAAACGATT  AAAAGA  ATG  AGA  TTT  CCT  TCA  ATT  TTT  ACT  GCA  GTT  TTA            109
                    Met  Arg  Phe  Pro  Ser  Ile  Phe  Thr  Ala  Val  Leu
                    -85            -80                           -75

TTC  GCA  GCA  TCC  TCC  GCA  TTA  GCT  GCT  CCA  GTC  AAC  ACT  ACA  ACA  GAA      157
Phe  Ala  Ala  Ser  Ser  Ala  Leu  Ala  Ala  Pro  Val  Asn  Thr  Thr  Thr  Glu
               -70                      -65                           -60

GAT  GAA  ACG  GCA  CAA  ATT  CCG  GCT  GAA  GCT  GTC  ATC  GGT  TAC  TCA  GAT      205
Asp  Glu  Thr  Ala  Gln  Ile  Pro  Ala  Glu  Ala  Val  Ile  Gly  Tyr  Ser  Asp
               -55                      -50                           -45

TTA  GAA  GGG  GAT  TTC  GAT  GTT  GCT  GTT  TTG  CCA  TTT  TCC  AAC  AGC  ACA      253
Leu  Glu  Gly  Asp  Phe  Asp  Val  Ala  Val  Leu  Pro  Phe  Ser  Asn  Ser  Thr
               -40                      -35                           -30

AAT  AAC  GGG  TTA  TTG  TTT  ATA  AAT  ACT  ACT  ATT  GCC  AGC  ATT  GCT  GCT      301
Asn  Asn  Gly  Leu  Leu  Phe  Ile  Asn  Thr  Thr  Ile  Ala  Ser  Ile  Ala  Ala
-25                                 -20                      -15

AAA  GAA  GAA  GGG  GTA  TCT  TTG  GAT  AAA  AGA  GAT  TTC  TGT  TTG  GAA  CCT      349
Lys  Glu  Glu  Gly  Val  Ser  Leu  Asp  Lys  Arg  Asp  Phe  Cys  Leu  Glu  Pro
-10                           -5                       1                       5

CCA  TAC  ACT  GGT  CCA  TGT  AAA  GCT  AGA  ATC  ATC  AGA  TAC  TTC  TAC  AAC      397
Pro  Tyr  Thr  Gly  Pro  Cys  Lys  Ala  Arg  Ile  Ile  Arg  Tyr  Phe  Tyr  Asn
                10                      15                       20

GCC  AAG  GCT  GGT  TTG  TGT  CAA  ACT  TTC  GTT  TAC  GGT  GGC  TGC  AGA  GCT      445
Ala  Lys  Ala  Gly  Leu  Cys  Gln  Thr  Phe  Val  Tyr  Gly  Gly  Cys  Arg  Ala
          25                        30                           35

AAG  TCC  AAC  AAC  TTC  GAA  TCT  GCT  GAA  GAC  TGC  ATG  AGA  ACT  TGT  GGT      493
Lys  Ser  Asn  Asn  Phe  Glu  Ser  Ala  Glu  Asp  Cys  Met  Arg  Thr  Cys  Gly
     40                        45                           50

GGT  GCC  TAATCTAGA                                                                  508
Gly  Ala
55
```

( 2 ) INFORMATION FOR SEQ ID NO:65:

( i ) SEQUENCE CHARACTERISTICS:
        ( A ) LENGTH: 141 amino acids
        ( B ) TYPE: amino acid
        ( D ) TOPOLOGY: linear ( i i ) MOLECULE TYPE: protein ( x i ) SEQUENCE DESCRIPTION: SEQ ID NO:65:

```
Met   Arg   Phe   Pro   Ser   Ile   Phe   Thr   Ala   Val   Leu   Phe   Ala   Ala   Ser   Ser
-85                     -80                           -75                              -70

Ala   Leu   Ala   Ala   Pro   Val   Asn   Thr   Thr   Thr   Glu   Asp   Glu   Thr   Ala   Gln
                        -65                           -60                              -55

Ile   Pro   Ala   Glu   Ala   Val   Ile   Gly   Tyr   Ser   Asp   Leu   Glu   Gly   Asp   Phe
                  -50                           -45                        -40

Asp   Val   Ala   Val   Leu   Pro   Phe   Ser   Asn   Ser   Thr   Asn   Asn   Gly   Leu   Leu
            -35                         -30                              -25

Phe   Ile   Asn   Thr   Thr   Ile   Ala   Ser   Ile   Ala   Ala   Lys   Glu   Glu   Gly   Val
-20                                 -15                        -10

Ser   Leu   Asp   Lys   Arg   Asp   Phe   Cys   Leu   Glu   Pro   Pro   Tyr   Thr   Gly   Pro
-5                            1                 5                                   10

Cys   Lys   Ala   Arg   Ile   Ile   Arg   Tyr   Phe   Tyr   Asn   Ala   Lys   Ala   Gly   Leu
                  15                        20                              25

Cys   Gln   Thr   Phe   Val   Tyr   Gly   Gly   Cys   Arg   Ala   Lys   Ser   Asn   Asn   Phe
            30                        35                              40

Glu   Ser   Ala   Glu   Asp   Cys   Met   Arg   Thr   Cys   Gly   Gly   Ala
      45                        50                        55
```

( 2 ) INFORMATION FOR SEQ ID NO:66:

( i ) SEQUENCE CHARACTERISTICS:
        ( A ) LENGTH: 110 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:66:

```
CAAGGCTGGT   TTGTGTCAAA   CTTTCGTTTA   CGGTGGCTGC   AGAGCTAAGT   CCAACAACTT        60
CGCTTCTGCT   GAAGACTGCA   TGAGAACTTG   TGGTGGTGCC   TAATCTAGAG                    110
```

( 2 ) INFORMATION FOR SEQ ID NO:67:

( i ) SEQUENCE CHARACTERISTICS:
        ( A ) LENGTH: 110 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:67:

```
TCGACTCTAG   ATTAGGCACC   ACCACAAGTT   CTCATGCAGT   CTTCAGCAGA   AGCGAAGTTG        60
TTGGACTTAG   CTCTGCAGCC   ACCGTAAACG   AAAGTTTGAC   ACAAACCAGC                    110
```

( 2 ) INFORMATION FOR SEQ ID NO:68:

( i ) SEQUENCE CHARACTERISTICS:
        ( A ) LENGTH: 508 base pairs
        ( B ) TYPE: nucleic acid
        ( C ) STRANDEDNESS: single
        ( D ) TOPOLOGY: linear (i i) MOLECULE TYPE: cDNA (i x) FEATURE:
    (A) NAME/KEY: CDS
    (B) LOCATION: 77..499

(i x) FEATURE:
    (A) NAME/KEY: sig_peptide
    (B) LOCATION: 77..331

(i x) FEATURE:
    (A) NAME/KEY: mat_peptide
    (B) LOCATION: 332..499

(x i) SEQUENCE DESCRIPTION: SEQ ID NO:68:

```
GAATTCCATT CAAGAATAGT TCAAACAAGA AGATTACAAA CTATCAATTT CATACACAAT           60

ATAAACGATT AAAAGA ATG AGA TTT CCT TCA ATT TTT ACT GCA GTT TTA             109
               Met Arg Phe Pro Ser Ile Phe Thr Ala Val Leu
               -85              -80                 -75

TTC GCA GCA TCC TCC GCA TTA GCT GCT CCA GTC AAC ACT ACA ACA GAA           157
Phe Ala Ala Ser Ser Ala Leu Ala Ala Pro Val Asn Thr Thr Thr Glu
            -70              -65                 -60

GAT GAA ACG GCA CAA ATT CCG GCT GAA GCT GTC ATC GGT TAC TCA GAT           205
Asp Glu Thr Ala Gln Ile Pro Ala Glu Ala Val Ile Gly Tyr Ser Asp
        -55              -50                 -45

TTA GAA GGG GAT TTC GAT GTT GCT GTT TTG CCA TTT TCC AAC AGC ACA           253
Leu Glu Gly Asp Phe Asp Val Ala Val Leu Pro Phe Ser Asn Ser Thr
        -40              -35                 -30

AAT AAC GGG TTA TTG TTT ATA AAT ACT ACT ATT GCC AGC ATT GCT GCT           301
Asn Asn Gly Leu Leu Phe Ile Asn Thr Thr Ile Ala Ser Ile Ala Ala
    -25              -20                 -15

AAA GAA GAA GGG GTA TCT TTG GAT AAA AGA GAT TTC TGT TTG GAA CCT           349
Lys Glu Glu Gly Val Ser Leu Asp Lys Arg Asp Phe Cys Leu Glu Pro
-10                   -5                    1                5

CCA TAC ACT GGT CCA TGT AAA GCT AGA ATC ATC AGA TAC TTC TAC AAC           397
Pro Tyr Thr Gly Pro Cys Lys Ala Arg Ile Ile Arg Tyr Phe Tyr Asn
             10              15                  20

GCC AAG GCT GGT TTG TGT CAA ACT TTC GTT TAC GGT GGC TGC AGA GCT           445
Ala Lys Ala Gly Leu Cys Gln Thr Phe Val Tyr Gly Gly Cys Arg Ala
         25              30                  35

AAG TCC AAC AAC TTC GCT TCT GCT GAA GAC TGC ATG AGA ACT TGT GGT           493
Lys Ser Asn Asn Phe Ala Ser Ala Glu Asp Cys Met Arg Thr Cys Gly
     40              45                  50

GGT GCC TAATCTAGA                                                          508
Gly Ala
55
```

(2) INFORMATION FOR SEQ ID NO:69:

(i) SEQUENCE CHARACTERISTICS:
        (A) LENGTH: 141 amino acids
        (B) TYPE: amino acid
        (D) TOPOLOGY: linear (i i) MOLECULE TYPE: protein (x i) SEQUENCE DESCRIPTION: SEQ ID NO:69:

```
Met Arg Phe Pro Ser Ile Phe Thr Ala Val Leu Phe Ala Ala Ser Ser
-85              -80                 -75                 -70

Ala Leu Ala Ala Pro Val Asn Thr Thr Thr Glu Asp Glu Thr Ala Gln
             -65                 -60                 -55

Ile Pro Ala Glu Ala Val Ile Gly Tyr Ser Asp Leu Glu Gly Asp Phe
         -50                 -45                 -40
```

| | | | | | | | | | | | | | | |
|---|---|---|---|---|---|---|---|---|---|---|---|---|---|---|
| Asp | Val | Ala | Val | Leu | Pro | Phe | Ser | Asn | Ser | Thr | Asn | Asn | Gly | Leu | Leu |
| | | -35 | | | | | -30 | | | | | -25 | | | |
| Phe | Ile | Asn | Thr | Thr | Ile | Ala | Ser | Ile | Ala | Ala | Lys | Glu | Glu | Gly | Val |
| | -20 | | | | -15 | | | | | | -10 | | | | |
| Ser | Leu | Asp | Lys | Arg | Asp | Phe | Cys | Leu | Glu | Pro | Pro | Tyr | Thr | Gly | Pro |
| -5 | | | | | 1 | | | | 5 | | | | | 10 | |
| Cys | Lys | Ala | Arg | Ile | Ile | Arg | Tyr | Phe | Tyr | Asn | Ala | Lys | Ala | Gly | Leu |
| | | | 15 | | | | | 20 | | | | | 25 | | |
| Cys | Gln | Thr | Phe | Val | Tyr | Gly | Gly | Cys | Arg | Ala | Lys | Ser | Asn | Asn | Phe |
| | | 30 | | | | | 35 | | | | | 40 | | | |
| Ala | Ser | Ala | Glu | Asp | Cys | Met | Arg | Thr | Cys | Gly | Gly | Ala | | | |
| | 45 | | | | | 50 | | | | | 55 | | | | |

( 2 ) INFORMATION FOR SEQ ID NO:70:

( i ) SEQUENCE CHARACTERISTICS:
        ( A ) LENGTH: 412 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 77..403

( i x ) FEATURE:
        ( A ) NAME/KEY: sig_peptide
        ( B ) LOCATION: 77..235

( i x ) FEATURE:
        ( A ) NAME/KEY: mat_peptide
        ( B ) LOCATION: 236..403

( x i ) SEQUENCE DESCRIPTION: SEQ ID NO:70:

| | | | | | | | | | | | |
|---|---|---|---|---|---|---|---|---|---|---|---|
| GAATTCCATT | CAAGAATAGT | TCAAACAAGA | AGATTACAAA | CTATCAATTT | CATACACAAT | | | | | | 60 |
| ATAAACGACC | AAAAGA | ATG | AAG | GCT | GTT | TTC | TTG | GTT | TTG | TCC | TTG ATC | 109 |
| | | Met | Lys | Ala | Val | Phe | Leu | Val | Leu | Ser | Leu Ile | |
| | | -53 | | | -50 | | | | | | -45 | |

| GGA | TTC | TGC | TGG | GCC | CAA | CCA | GTC | ACT | GGC | GAT | GAA | TCA | TCT | GTT | GAG | 157 |
|---|---|---|---|---|---|---|---|---|---|---|---|---|---|---|---|---|
| Gly | Phe | Cys | Trp | Ala | Gln | Pro | Val | Thr | Gly | Asp | Glu | Ser | Ser | Val | Glu | |
| | | -40 | | | | | -35 | | | | | -30 | | | | |

| ATT | CCG | GAA | GAG | TCT | CTG | ATC | ATC | GCT | GAA | AAC | ACC | ACT | TTG | GCT | AAC | 205 |
|---|---|---|---|---|---|---|---|---|---|---|---|---|---|---|---|---|
| Ile | Pro | Glu | Glu | Ser | Leu | Ile | Ile | Ala | Glu | Asn | Thr | Thr | Leu | Ala | Asn | |
| | -25 | | | | | -20 | | | | | | -15 | | | | |

| GTC | GCC | ATG | GCT | GAG | AGA | TTG | GAG | AAG | AGG | GAT | TTC | TGT | TTG | GAA | CCT | 253 |
|---|---|---|---|---|---|---|---|---|---|---|---|---|---|---|---|---|
| Val | Ala | Met | Ala | Glu | Arg | Leu | Glu | Lys | Arg | Asp | Phe | Cys | Leu | Glu | Pro | |
| -10 | | | | | -5 | | | | | | 1 | | | | 5 | |

| CCA | TCT | ACT | GGT | CCA | TGT | AAA | GCT | AGA | ATC | ATC | AGA | TAC | TTC | TAC | GAC | 301 |
|---|---|---|---|---|---|---|---|---|---|---|---|---|---|---|---|---|
| Pro | Ser | Thr | Gly | Pro | Cys | Lys | Ala | Arg | Ile | Ile | Arg | Tyr | Phe | Tyr | Asp | |
| | | | 10 | | | | | 15 | | | | | | 20 | | |

| GCC | ACT | GCT | GGT | TTG | TGT | GAA | ACT | TTC | GTT | TAC | GGT | GGC | TGC | AGA | GCT | 349 |
|---|---|---|---|---|---|---|---|---|---|---|---|---|---|---|---|---|
| Ala | Thr | Ala | Gly | Leu | Cys | Glu | Thr | Phe | Val | Tyr | Gly | Gly | Cys | Arg | Ala | |
| | | | 25 | | | | | 30 | | | | | 35 | | | |

| AAC | AGA | AAC | AAC | TTC | AAG | TCT | GCT | GAA | GAC | TGC | ATG | GAA | ACT | TGT | GGT | 397 |
|---|---|---|---|---|---|---|---|---|---|---|---|---|---|---|---|---|
| Asn | Arg | Asn | Asn | Phe | Lys | Ser | Ala | Glu | Asp | Cys | Met | Glu | Thr | Cys | Gly | |
| | 40 | | | | | 45 | | | | | 50 | | | | | |

| GGT | GCC | TAATCTAGA | | | | | | | | | | | | | | 412 |
|---|---|---|---|---|---|---|---|---|---|---|---|---|---|---|---|---|
| Gly | Ala | | | | | | | | | | | | | | | |
| | 55 | | | | | | | | | | | | | | | |

( 2 ) INFORMATION FOR SEQ ID NO:71:

( i ) SEQUENCE CHARACTERISTICS:
    ( A ) LENGTH: 109 amino acids
    ( B ) TYPE: amino acid
    ( D ) TOPOLOGY: linear ( i i ) MOLECULE TYPE: protein ( x i ) SEQUENCE DESCRIPTION: SEQ ID NO:71:

```
Met Lys Ala Val Phe Leu Val Leu Ser Leu Ile Gly Phe Cys Trp Ala
-53         -50                 -45                 -40

Gln Pro Val Thr Gly Asp Glu Ser Ser Val Glu Ile Pro Glu Glu Ser
        -35                 -30                 -25

Leu Ile Ile Ala Glu Asn Thr Thr Leu Ala Asn Val Ala Met Ala Glu
    -20                 -15                 -10

Arg Leu Glu Lys Arg Asp Phe Cys Leu Glu Pro Pro Ser Thr Gly Pro
-5                   1               5                   10

Cys Lys Ala Arg Ile Ile Arg Tyr Phe Tyr Asp Ala Thr Ala Gly Leu
            15                  20                  25

Cys Glu Thr Phe Val Tyr Gly Gly Cys Arg Ala Asn Arg Asn Asn Phe
        30                  35                  40

Lys Ser Ala Glu Asp Cys Met Glu Thr Cys Gly Gly Ala
    45                  50                  55
```

( 2 ) INFORMATION FOR SEQ ID NO:72:

( i ) SEQUENCE CHARACTERISTICS:
        ( A ) LENGTH: 508 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 77..499

( i x ) FEATURE:
        ( A ) NAME/KEY: sig_peptide
        ( B ) LOCATION: 77..331

( i x ) FEATURE:
        ( A ) NAME/KEY: mat_peptide
        ( B ) LOCATION: 332..499

( x i ) SEQUENCE DESCRIPTION: SEQ ID NO:72:

```
GAATTCCATT CAAGAATAGT TCAAACAAGA AGATTACAAA CTATCAATTT CATACACAAT        60

ATAAACGATT AAAAGA ATG AGA TTT CCT TCA ATT TTT ACT GCA GTT TTA          109
                 Met Arg Phe Pro Ser Ile Phe Thr Ala Val Leu
                 -85                 -80                 -75

TTC GCA GCA TCC TCC GCA TTA GCT GCT CCA GTC AAC ACT ACA ACA GAA        157
Phe Ala Ala Ser Ser Ala Leu Ala Ala Pro Val Asn Thr Thr Thr Glu
            -70                 -65                 -60

GAT GAA ACG GCA CAA ATT CCG GCT GAA GCT GTC ATC GGT TAC TCA GAT        205
Asp Glu Thr Ala Gln Ile Pro Ala Glu Ala Val Ile Gly Tyr Ser Asp
        -55                 -50                 -45

TTA GAA GGG GAT TTC GAT GTT GCT GTT TTG CCA TTT TCC AAC AGC ACA        253
Leu Glu Gly Asp Phe Asp Val Ala Val Leu Pro Phe Ser Asn Ser Thr
        -40                 -35                 -30

AAT AAC GGG TTA TTG TTT ATA AAT ACT ACT ATT GCC AGC ATT GCT GCT        301
Asn Asn Gly Leu Leu Phe Ile Asn Thr Thr Ile Ala Ser Ile Ala Ala
    -25                 -20                 -15

AAA GAA GAA GGG GTA TCT TTG GAT AAA AGA GAT TTC TGT TTG GAA CCT        349
Lys Glu Glu Gly Val Ser Leu Asp Lys Arg Asp Phe Cys Leu Glu Pro
-10                 -5                  1                   5
```

```
CCA TAC ACT GGT CCA TGT AAA GCT AGA ATC ATC AGA TAC TTC TAC GAC    397
Pro Tyr Thr Gly Pro Cys Lys Ala Arg Ile Ile Arg Tyr Phe Tyr Asp
        10                      15                  20

GCC ACT GCT GGT TTG TGT GAA ACT TTC GTT TAC GGT GGC TGC AGA GCT    445
Ala Thr Ala Gly Leu Cys Glu Thr Phe Val Tyr Gly Gly Cys Arg Ala
        25                      30                  35

AAG AGA AAC AAC TTC AAG TCT GCT GAA GAC TGC ATG GAA ACT TGT GGT    493
Lys Arg Asn Asn Phe Lys Ser Ala Glu Asp Cys Met Glu Thr Cys Gly
    40                      45                  50

GGT GCC TAATCTAGA                                                   508
Gly Ala
55
```

(2) INFORMATION FOR SEQ ID NO:73:

(i) SEQUENCE CHARACTERISTICS:
        (A) LENGTH: 141 amino acids
        (B) TYPE: amino acid
        (D) TOPOLOGY: linear (ii) MOLECULE TYPE: protein (xi) SEQUENCE DESCRIPTION: SEQ ID NO:73:

```
Met Arg Phe Pro Ser Ile Phe Thr Ala Val Leu Phe Ala Ala Ser Ser
-85             -80              -75             -70

Ala Leu Ala Ala Pro Val Asn Thr Thr Thr Glu Asp Glu Thr Ala Gln
            -65              -60             -55

Ile Pro Ala Glu Ala Val Ile Gly Tyr Ser Asp Leu Glu Gly Asp Phe
        -50              -45             -40

Asp Val Ala Val Leu Pro Phe Ser Asn Ser Thr Asn Asn Gly Leu Leu
        -35              -30             -25

Phe Ile Asn Thr Thr Ile Ala Ser Ile Ala Ala Lys Glu Glu Gly Val
    -20              -15             -10

Ser Leu Asp Lys Arg Asp Phe Cys Leu Glu Pro Pro Tyr Thr Gly Pro
-5              1                5                   10

Cys Lys Ala Arg Ile Ile Arg Tyr Phe Tyr Asp Ala Thr Ala Gly Leu
            15                  20                  25

Cys Glu Thr Phe Val Tyr Gly Gly Cys Arg Ala Lys Arg Asn Asn Phe
        30                  35                  40

Lys Ser Ala Glu Asp Cys Met Glu Thr Cys Gly Gly Ala
    45                  50                  55
```

(2) INFORMATION FOR SEQ ID NO:74:

(i) SEQUENCE CHARACTERISTICS:
        (A) LENGTH: 412 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 77..403

(ix) FEATURE:
        (A) NAME/KEY: sig_peptide
        (B) LOCATION: 77..235

(ix) FEATURE:
        (A) NAME/KEY: mat_peptide
        (B) LOCATION: 236..403

(xi) SEQUENCE DESCRIPTION: SEQ ID NO:74:

```
GAATTCCATT CAAGAATAGT TCAAACAAGA AGATTACAAA CTATCAATTT CATACACAAT        60

ATAAACGACC AAAAGA ATG AAG GCT GTT TTC TTG GTT TTG TCC TTG ATC          109
              Met Lys Ala Val Phe Leu Val Leu Ser Leu Ile
              -53     -50                 -45

GGA TTC TGC TGG GCC CAA CCA GTC ACT GGC GAT GAA TCA TCT GTT GAG        157
Gly Phe Cys Trp Ala Gln Pro Val Thr Gly Asp Glu Ser Ser Val Glu
        -40                 -35                 -30

ATT CCG GAA GAG TCT CTG ATC ATC GCT GAA AAC ACC ACT TTG GCT AAC        205
Ile Pro Glu Glu Ser Leu Ile Ile Ala Glu Asn Thr Thr Leu Ala Asn
    -25             -20                     -15

GTC GCC ATG GCT GAG AGA TTG GAG AAG AGG GAT TTC TGT TTG GAA CCT        253
Val Ala Met Ala Glu Arg Leu Glu Lys Arg Asp Phe Cys Leu Glu Pro
-10                     -5                  1               5

CCA TCT ACT GGT CCA TGT AAA GCT AGA ATC ATC AGA TAC TTC TAC AAC        301
Pro Ser Thr Gly Pro Cys Lys Ala Arg Ile Ile Arg Tyr Phe Tyr Asn
            10                  15                  20

GCC AAG GCT GGT TTG TGT CAA ACT TTC GTT TAC GGT GGC TGC AGA GGT        349
Ala Lys Ala Gly Leu Cys Gln Thr Phe Val Tyr Gly Gly Cys Arg Gly
        25                  30                  35

AAC GGC AAC AAC TTC AAG TCT GCT GAA GAC TGC ATG GAA ACT TGT GGT        397
Asn Gly Asn Asn Phe Lys Ser Ala Glu Asp Cys Met Glu Thr Cys Gly
        40                  45                  50

GGT GCC TAATCTAGA                                                       412
Gly Ala
55
```

( 2 ) INFORMATION FOR SEQ ID NO:75:

( i ) SEQUENCE CHARACTERISTICS:
        ( A ) LENGTH: 109 amino acids
        ( B ) TYPE: amino acid
        ( D ) TOPOLOGY: linear ( i i ) MOLECULE TYPE: protein ( x i ) SEQUENCE DESCRIPTION: SEQ ID NO:75:

```
Met Lys Ala Val Phe Leu Val Leu Ser Leu Ile Gly Phe Cys Trp Ala
-53         -50                 -45                 -40

Gln Pro Val Thr Gly Asp Glu Ser Ser Val Glu Ile Pro Glu Glu Ser
        -35                 -30                 -25

Leu Ile Ile Ala Glu Asn Thr Thr Leu Ala Asn Val Ala Met Ala Glu
    -20                 -15                 -10

Arg Leu Glu Lys Arg Asp Phe Cys Leu Glu Pro Pro Ser Thr Gly Pro
-5                   1               5                   10

Cys Lys Ala Arg Ile Ile Arg Tyr Phe Tyr Asn Ala Lys Ala Gly Leu
            15                  20                  25

Cys Gln Thr Phe Val Tyr Gly Gly Cys Arg Gly Asn Gly Asn Asn Phe
        30                  35                  40

Lys Ser Ala Glu Asp Cys Met Glu Thr Cys Gly Gly Ala
        45                  50                  55
```

( 2 ) INFORMATION FOR SEQ ID NO:76:

( i ) SEQUENCE CHARACTERISTICS:
        ( A ) LENGTH: 508 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:

(A) NAME/KEY: CDS
(B) LOCATION: 77..499

(ix) FEATURE:
(A) NAME/KEY: sig_peptide
(B) LOCATION: 77..331

(ix) FEATURE:
(A) NAME/KEY: mat_peptide
(B) LOCATION: 332..499

(xi) SEQUENCE DESCRIPTION: SEQ ID NO:76:

```
GAATTCCATT CAAGAATAGT TCAAACAAGA AGATTACAAA CTATCAATTT CATACACAAT        60

ATAAACGATT AAAAGA ATG AGA TTT CCT TCA ATT TTT ACT GCA GTT TTA          109
               Met Arg Phe Pro Ser Ile Phe Thr Ala Val Leu
               -85         -80                     -75

TTC GCA GCA TCC TCC GCA TTA GCT GCT CCA GTC AAC ACT ACA ACA GAA        157
Phe Ala Ala Ser Ser Ala Leu Ala Ala Pro Val Asn Thr Thr Thr Glu
                -70                 -65                     -60

GAT GAA ACG GCA CAA ATT CCG GCT GAA GCT GTC ATC GGT TAC TCA GAT        205
Asp Glu Thr Ala Gln Ile Pro Ala Glu Ala Val Ile Gly Tyr Ser Asp
            -55                 -50                 -45

TTA GAA GGG GAT TTC GAT GTT GCT GTT TTG CCA TTT TCC AAC AGC ACA        253
Leu Glu Gly Asp Phe Asp Val Ala Val Leu Pro Phe Ser Asn Ser Thr
        -40                 -35                 -30

AAT AAC GGG TTA TTG TTT ATA AAT ACT ACT ATT GCC AGC ATT GCT GCT        301
Asn Asn Gly Leu Leu Phe Ile Asn Thr Thr Ile Ala Ser Ile Ala Ala
    -25                 -20                 -15

AAA GAA GAA GGG GTA TCT TTG GAT AAA AGA GAT TTC TGT TTG GAA CCT        349
Lys Glu Glu Gly Val Ser Leu Asp Lys Arg Asp Phe Cys Leu Glu Pro
-10                  -5                   1                   5

CCA TAC ACT GGT CCA TGT AAA GCT AGA ATC ATC AGA TAC TTC TAC AAC        397
Pro Tyr Thr Gly Pro Cys Lys Ala Arg Ile Ile Arg Tyr Phe Tyr Asn
             10                  15                  20

GCC AAG GCT GGT TTG TGT CAA ACT TTC GTT TAC GGT GGC TGC AGA GCT        445
Ala Lys Ala Gly Leu Cys Gln Thr Phe Val Tyr Gly Gly Cys Arg Ala
         25                  30                  35

AAG TCC AAC AAC TTC AAG TCT GCT GAA GAC TGC ATG GAA ACT TGT GGT        493
Lys Ser Asn Asn Phe Lys Ser Ala Glu Asp Cys Met Glu Thr Cys Gly
     40                  45                  50

GGT GCC TAATCTAGA                                                      508
Gly Ala
 55
```

(2) INFORMATION FOR SEQ ID NO:77:

(i) SEQUENCE CHARACTERISTICS:
(A) LENGTH: 141 amino acids
(B) TYPE: amino acid
(D) TOPOLOGY: linear (ii) MOLECULE TYPE: protein (xi) SEQUENCE DESCRIPTION: SEQ ID NO:77:

```
Met Arg Phe Pro Ser Ile Phe Thr Ala Val Leu Phe Ala Ala Ser Ser
-85              -80                  -75                  -70

Ala Leu Ala Ala Pro Val Asn Thr Thr Thr Glu Asp Glu Thr Ala Gln
                 -65                 -60                  -55

Ile Pro Ala Glu Ala Val Ile Gly Tyr Ser Asp Leu Glu Gly Asp Phe
             -50                 -45                 -40

Asp Val Ala Val Leu Pro Phe Ser Asn Ser Thr Asn Asn Gly Leu Leu
         -35                 -30                 -25

Phe Ile Asn Thr Thr Ile Ala Ser Ile Ala Ala Lys Glu Glu Gly Val
```

```
                -20                      -15                       -10
Ser  Leu  Asp  Lys  Arg  Asp  Phe  Cys  Leu  Glu  Pro  Pro  Tyr  Thr  Gly  Pro
 -5                       1                 5                                10

Cys  Lys  Ala  Arg  Ile  Ile  Arg  Tyr  Phe  Tyr  Asn  Ala  Lys  Ala  Gly  Leu
                15                      20                      25

Cys  Gln  Thr  Phe  Val  Tyr  Gly  Gly  Cys  Arg  Ala  Lys  Ser  Asn  Asn  Phe
               30                       35                      40

Lys  Ser  Ala  Glu  Asp  Cys  Met  Glu  Thr  Cys  Gly  Gly  Ala
      45                     50                      55
```

( 2 ) INFORMATION FOR SEQ ID NO:78:

( i ) SEQUENCE CHARACTERISTICS:
        ( A ) LENGTH: 508 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 77..499

( i x ) FEATURE:
        ( A ) NAME/KEY: sig_peptide
        ( B ) LOCATION: 77..331

( i x ) FEATURE:
        ( A ) NAME/KEY: mat_peptide
        ( B ) LOCATION: 332..499

( x i ) SEQUENCE DESCRIPTION: SEQ ID NO:78:

```
GAATTCCATT  CAAGAATAGT  TCAAACAAGA  AGATTACAAA  CTATCAATTT  CATACACAAT              60

ATAAACGATT  AAAAGA  ATG  AGA  TTT  CCT  TCA  ATT  TTT  ACT  GCA  GTT  TTA          109
                    Met  Arg  Phe  Pro  Ser  Ile  Phe  Thr  Ala  Val  Leu
                    -85            -80                           -75

TTC  GCA  GCA  TCC  TCC  GCA  TTA  GCT  GCT  CCA  GTC  AAC  ACT  ACA  ACA  GAA    157
Phe  Ala  Ala  Ser  Ser  Ala  Leu  Ala  Ala  Pro  Val  Asn  Thr  Thr  Thr  Glu
               -70                      -65                      -60

GAT  GAA  ACG  GCA  CAA  ATT  CCG  GCT  GAA  GCT  GTC  ATC  GGT  TAC  TCA  GAT    205
Asp  Glu  Thr  Ala  Gln  Ile  Pro  Ala  Glu  Ala  Val  Ile  Gly  Tyr  Ser  Asp
          -55                      -50                           -45

TTA  GAA  GGG  GAT  TTC  GAT  GTT  GCT  GTT  TTG  CCA  TTT  TCC  AAC  AGC  ACA    253
Leu  Glu  Gly  Asp  Phe  Asp  Val  Ala  Val  Leu  Pro  Phe  Ser  Asn  Ser  Thr
          -40                      -35                      -30

AAT  AAC  GGG  TTA  TTG  TTT  ATA  AAT  ACT  ACT  ATT  GCC  AGC  ATT  GCT  GCT    301
Asn  Asn  Gly  Leu  Leu  Phe  Ile  Asn  Thr  Thr  Ile  Ala  Ser  Ile  Ala  Ala
-25                      -20                      -15

AAA  GAA  GAA  GGG  GTA  TCT  TTG  GAT  AAA  AGA  GAT  TTC  TGT  TTG  GAA  CCT    349
Lys  Glu  Glu  Gly  Val  Ser  Leu  Asp  Lys  Arg  Asp  Phe  Cys  Leu  Glu  Pro
-10                       -5                      1                 5

CCA  TAC  ACT  GGT  CCA  TGT  AAA  GCT  AGA  ATC  ATC  AGA  TAC  TTC  TAC  AAC    397
Pro  Tyr  Thr  Gly  Pro  Cys  Lys  Ala  Arg  Ile  Ile  Arg  Tyr  Phe  Tyr  Asn
               10                       15                      20

GCC  AAG  GCT  GGT  TTG  TGT  CAA  ACT  TTC  GTT  TAC  GGT  GGC  TGC  AGA  GCT    445
Ala  Lys  Ala  Gly  Leu  Cys  Gln  Thr  Phe  Val  Tyr  Gly  Gly  Cys  Arg  Ala
          25                       30                      35

AAG  GAA  AAC  AAC  TTC  AAG  TCT  GCT  GAA  GAC  TGC  ATG  GAA  ACT  TGT  GGT    493
Lys  Glu  Asn  Asn  Phe  Lys  Ser  Ala  Glu  Asp  Cys  Met  Glu  Thr  Cys  Gly
     40                       45                      50

GGT  GCC  TAATCTAGA                                                                 508
Gly  Ala
55
```

( 2 ) INFORMATION FOR SEQ ID NO:79:

( i ) SEQUENCE CHARACTERISTICS:
        ( A ) LENGTH: 141 amino acids
        ( B ) TYPE: amino acid
        ( D ) TOPOLOGY: linear ( i i ) MOLECULE TYPE: protein ( x i ) SEQUENCE DESCRIPTION: SEQ ID NO:79:

```
Met  Arg  Phe  Pro  Ser  Ile  Phe  Thr  Ala  Val  Leu  Phe  Ala  Ala  Ser  Ser
-85                 -80                 -75                      -70

Ala  Leu  Ala  Ala  Pro  Val  Asn  Thr  Thr  Thr  Glu  Asp  Glu  Thr  Ala  Gln
                -65                      -60                      -55

Ile  Pro  Ala  Glu  Ala  Val  Ile  Gly  Tyr  Ser  Asp  Leu  Glu  Gly  Asp  Phe
          -50                      -45                      -40

Asp  Val  Ala  Val  Leu  Pro  Phe  Ser  Asn  Ser  Thr  Asn  Asn  Gly  Leu  Leu
          -35                      -30                      -25

Phe  Ile  Asn  Thr  Thr  Ile  Ala  Ser  Ile  Ala  Ala  Lys  Glu  Glu  Gly  Val
     -20                      -15                      -10

Ser  Leu  Asp  Lys  Arg  Asp  Phe  Cys  Leu  Glu  Pro  Pro  Tyr  Thr  Gly  Pro
 -5                       1                 5                         10

Cys  Lys  Ala  Arg  Ile  Ile  Arg  Tyr  Phe  Tyr  Asn  Ala  Lys  Ala  Gly  Leu
               15                    20                    25

Cys  Gln  Thr  Phe  Val  Tyr  Gly  Gly  Cys  Arg  Ala  Lys  Glu  Asn  Asn  Phe
          30                        35                    40

Lys  Ser  Ala  Glu  Asp  Cys  Met  Glu  Thr  Cys  Gly  Gly  Ala
     45                    50                    55
```

( 2 ) INFORMATION FOR SEQ ID NO:80:

( i ) SEQUENCE CHARACTERISTICS:
        ( A ) LENGTH: 508 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 77..499

( i x ) FEATURE:
        ( A ) NAME/KEY: sig_peptide
        ( B ) LOCATION: 77..331

( i x ) FEATURE:
        ( A ) NAME/KEY: mat_peptide
        ( B ) LOCATION: 332..499

( x i ) SEQUENCE DESCRIPTION: SEQ ID NO:80:

```
GAATTCCATT  CAAGAATAGT  TCAAACAAGA  AGATTACAAA  CTATCAATTT  CATACACAAT        60

ATAAACGATT  AAAAGA ATG  AGA TTT CCT  TCA ATT TTT  ACT GCA GTT  TTA           109
                   Met  Arg Phe Pro  Ser Ile Phe  Thr Ala Val  Leu
                   -85                -80                       -75

TTC GCA GCA TCC TCC GCA TTA GCT GCT CCA GTC AAC ACT ACA ACA GAA              157
Phe Ala Ala Ser Ser Ala Leu Ala Ala Pro Val Asn Thr Thr Thr Glu
            -70                 -65                 -60

GAT GAA ACG GCA CAA ATT CCG GCT GAA GCT GTC ATC GGT TAC TCA GAT              205
Asp Glu Thr Ala Gln Ile Pro Ala Glu Ala Val Ile Gly Tyr Ser Asp
            -55                 -50                 -45

TTA GAA GGG GAT TTC GAT GTT GCT GTT TTG CCA TTT TCC AAC AGC ACA              253
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| Leu | Glu | Gly | Asp | Phe | Asp | Val | Ala | Val | Leu | Pro | Phe | Ser | Asn | Ser | Thr |     |
|     | -40 |     |     |     |     | -35 |     |     |     |     | -30 |     |     |     |     |     |
| AAT | AAC | GGG | TTA | TTG | TTT | ATA | AAT | ACT | ACT | ATT | GCC | AGC | ATT | GCT | GCT | 301 |
| Asn | Asn | Gly | Leu | Leu | Phe | Ile | Asn | Thr | Thr | Ile | Ala | Ser | Ile | Ala | Ala |     |
|     | -25 |     |     |     |     | -20 |     |     |     |     | -15 |     |     |     |     |     |
| AAA | GAA | GAA | GGG | GTA | TCT | TTG | GAT | AAA | AGA | GAT | TTC | TGT | TTG | GAA | CCT | 349 |
| Lys | Glu | Glu | Gly | Val | Ser | Leu | Asp | Lys | Arg | Asp | Phe | Cys | Leu | Glu | Pro |     |
| -10 |     |     |     |     | -5  |     |     |     |     | 1   |     |     |     |     | 5   |     |
| CCA | TAC | ACT | GGT | CCA | TGT | AAA | GCT | AGA | ATC | ATC | AGA | TAC | TTC | TAC | AAC | 397 |
| Pro | Tyr | Thr | Gly | Pro | Cys | Lys | Ala | Arg | Ile | Ile | Arg | Tyr | Phe | Tyr | Asn |     |
|     |     |     | 10  |     |     |     |     | 15  |     |     |     |     | 20  |     |     |     |
| GCC | GAA | GCT | GGT | TTG | TGT | CAA | ACT | TTC | GTT | TAC | GGT | GGC | TGC | AGA | GCT | 445 |
| Ala | Glu | Ala | Gly | Leu | Cys | Gln | Thr | Phe | Val | Tyr | Gly | Gly | Cys | Arg | Ala |     |
|     |     | 25  |     |     |     |     | 30  |     |     |     |     | 35  |     |     |     |     |
| AAG | TCC | AAC | AAC | TTC | AAG | TCT | GCT | GAA | GAC | TGC | ATG | GAA | ACT | TGT | GGT | 493 |
| Lys | Ser | Asn | Asn | Phe | Lys | Ser | Ala | Glu | Asp | Cys | Met | Glu | Thr | Cys | Gly |     |
|     | 40  |     |     |     |     | 45  |     |     |     |     | 50  |     |     |     |     |     |
| GGT | GCC | TAATCTAGA |   |   |   |   |   |   |   |   |   |   |   |   |   | 508 |
| Gly | Ala |     |     |     |     |     |     |     |     |     |     |     |     |     |     |     |
| 55  |     |     |     |     |     |     |     |     |     |     |     |     |     |     |     |     |

( 2 ) INFORMATION FOR SEQ ID NO:81:

( i ) SEQUENCE CHARACTERISTICS:
        ( A ) LENGTH: 141 amino acids
        ( B ) TYPE: amino acid
        ( D ) TOPOLOGY: linear ( i i ) MOLECULE TYPE: protein ( x i ) SEQUENCE DESCRIPTION: SEQ ID NO:81:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Arg | Phe | Pro | Ser | Ile | Phe | Thr | Ala | Val | Leu | Phe | Ala | Ala | Ser | Ser |
| -85 |     |     |     |     | -80 |     |     |     |     | -75 |     |     |     |     | -70 |
| Ala | Leu | Ala | Ala | Pro | Val | Asn | Thr | Thr | Thr | Glu | Asp | Glu | Thr | Ala | Gln |
|     |     |     |     | -65 |     |     |     |     | -60 |     |     |     |     | -55 |     |
| Ile | Pro | Ala | Glu | Ala | Val | Ile | Gly | Tyr | Ser | Asp | Leu | Glu | Gly | Asp | Phe |
|     |     |     | -50 |     |     |     |     | -45 |     |     |     |     | -40 |     |     |
| Asp | Val | Ala | Val | Leu | Pro | Phe | Ser | Asn | Ser | Thr | Asn | Asn | Gly | Leu | Leu |
|     |     | -35 |     |     |     |     | -30 |     |     |     |     | -25 |     |     |     |
| Phe | Ile | Asn | Thr | Thr | Ile | Ala | Ser | Ile | Ala | Ala | Lys | Glu | Glu | Gly | Val |
|     | -20 |     |     |     |     | -15 |     |     |     |     | -10 |     |     |     |     |
| Ser | Leu | Asp | Lys | Arg | Asp | Phe | Cys | Leu | Glu | Pro | Pro | Tyr | Thr | Gly | Pro |
| -5  |     |     |     |     | 1   |     |     |     | 5   |     |     |     |     | 10  |     |
| Cys | Lys | Ala | Arg | Ile | Ile | Arg | Tyr | Phe | Tyr | Asn | Ala | Glu | Ala | Gly | Leu |
|     |     |     | 15  |     |     |     |     | 20  |     |     |     |     | 25  |     |     |
| Cys | Gln | Thr | Phe | Val | Tyr | Gly | Gly | Cys | Arg | Ala | Lys | Ser | Asn | Asn | Phe |
|     |     | 30  |     |     |     |     | 35  |     |     |     |     | 40  |     |     |     |
| Lys | Ser | Ala | Glu | Asp | Cys | Met | Glu | Thr | Cys | Gly | Gly | Ala |     |     |     |
|     | 45  |     |     |     |     | 50  |     |     |     |     | 55  |     |     |     |     |

( 2 ) INFORMATION FOR SEQ ID NO:82:

( i ) SEQUENCE CHARACTERISTICS:
        ( A ) LENGTH: 508 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 77..499

( i x ) FEATURE:
    ( A ) NAME/KEY: sig_peptide
    ( B ) LOCATION: 77..331

( i x ) FEATURE:
    ( A ) NAME/KEY: mat_peptide
    ( B ) LOCATION: 332..499

( x i ) SEQUENCE DESCRIPTION: SEQ ID NO:82:

```
GAATTCCATT CAAGAATAGT TCAAACAAGA AGATTACAAA CTATCAATTT CATACACAAT           60

ATAAACGATT AAAAGA ATG AGA TTT CCT TCA ATT TTT ACT GCA GTT TTA              109
               Met Arg Phe Pro Ser Ile Phe Thr Ala Val Leu
               -85             -80                 -75

TTC GCA GCA TCC TCC GCA TTA GCT GCT CCA GTC AAC ACT ACA ACA GAA            157
Phe Ala Ala Ser Ser Ala Leu Ala Ala Pro Val Asn Thr Thr Thr Glu
            -70             -65                 -60

GAT GAA ACG GCA CAA ATT CCG GCT GAA GCT GTC ATC GGT TAC TCA GAT            205
Asp Glu Thr Ala Gln Ile Pro Ala Glu Ala Val Ile Gly Tyr Ser Asp
        -55             -50             -45

TTA GAA GGG GAT TTC GAT GTT GCT GTT TTG CCA TTT TCC AAC AGC ACA            253
Leu Glu Gly Asp Phe Asp Val Ala Val Leu Pro Phe Ser Asn Ser Thr
    -40             -35             -30

AAT AAC GGG TTA TTG TTT ATA AAT ACT ACT ATT GCC AGC ATT GCT GCT            301
Asn Asn Gly Leu Leu Phe Ile Asn Thr Thr Ile Ala Ser Ile Ala Ala
-25             -20             -15

AAA GAA GAA GGG GTA TCT TTG GAT AAA AGA GAT TTC TGT TTG GAA CCT            349
Lys Glu Glu Gly Val Ser Leu Asp Lys Arg Asp Phe Cys Leu Glu Pro
-10             -5              1              5

CCA TAC ACT GGT CCA TGT AAA GCT AGA ATC ATC AGA TAC TTC TAC AAC            397
Pro Tyr Thr Gly Pro Cys Lys Ala Arg Ile Ile Arg Tyr Phe Tyr Asn
            10              15              20

GCC GAA GCT GGT TTG TGT CAA ACT TTC GTT TAC GGT GGC TGC AGA GCT            445
Ala Glu Ala Gly Leu Cys Gln Thr Phe Val Tyr Gly Gly Cys Arg Ala
        25              30              35

AAG GAA AAC AAC TTC AAG TCT GCT GAA GAC TGC ATG GAA ACT TGT GGT            493
Lys Glu Asn Asn Phe Lys Ser Ala Glu Asp Cys Met Glu Thr Cys Gly
    40              45              50

GGT GCC TAATCTAGA                                                           508
Gly Ala
55
```

( 2 ) INFORMATION FOR SEQ ID NO:83:

( i ) SEQUENCE CHARACTERISTICS:
        ( A ) LENGTH: 141 amino acids
        ( B ) TYPE: amino acid
        ( D ) TOPOLOGY: linear ( i i ) MOLECULE TYPE: protein ( x i ) SEQUENCE DESCRIPTION: SEQ ID NO:83:

```
Met Arg Phe Pro Ser Ile Phe Thr Ala Val Leu Phe Ala Ala Ser Ser
-85             -80             -75             -70

Ala Leu Ala Ala Pro Val Asn Thr Thr Thr Glu Asp Glu Thr Ala Gln
            -65             -60             -55

Ile Pro Ala Glu Ala Val Ile Gly Tyr Ser Asp Leu Glu Gly Asp Phe
        -50             -45             -40

Asp Val Ala Val Leu Pro Phe Ser Asn Ser Thr Asn Asn Gly Leu Leu
            -35             -30             -25

Phe Ile Asn Thr Thr Ile Ala Ser Ile Ala Ala Lys Glu Glu Gly Val
    -20             -15             -10
```

| Ser -5 | Leu | Asp | Lys | Arg 1 | Asp | Phe | Cys | Leu 5 | Glu | Pro | Pro | Tyr | Thr 10 | Gly | Pro |
|---|---|---|---|---|---|---|---|---|---|---|---|---|---|---|---|
| Cys | Lys | Ala | Arg 15 | Ile | Ile | Arg | Tyr 20 | Phe | Tyr | Asn | Ala | Glu 25 | Ala | Gly | Leu |
| Cys | Gln | Thr 30 | Phe | Val | Tyr | Gly | Gly 35 | Cys | Arg | Ala | Lys | Glu 40 | Asn | Asn | Phe |
| Lys | Ser 45 | Ala | Glu | Asp | Cys | Met 50 | Glu | Thr | Cys | Gly | Gly 55 | Ala | | | |

PROCESS FOR PREPARING APROTININ AND APROTININ ANALOGS IN YEAST CELLS

This application is a continuation-in-part of application Ser. No. 08/024,925, filed Feb. 26, 1993, now abandoned, which is a continuation of application Ser. No. 07/466,408, now abandoned, filed Jun. 21, 1990. This application is also a continuation-in-part of application Ser. No. 07/598,737, U.S. Pat. No. 5,373,090, filed Nov. 19, 1990 and a continuation-in-part of application Ser. No. 07/827,687, now abandoned, filed Jan. 29, 1992. This application also claims priority under 35 U.S.C. §120 to PCT application no. PCT/DK88/00138, filed Aug. 26, 1988, PCT application no. PCT/DK89/0096, filed Apr. 25, 1989, and PCT application on. PCT/DK91/0029, filed Oct. 1, 1991.

1. FIELD OF INVENTION

The present invention relates to methods for producing aprotinin and analogs thereof in yeast, synthetic genes encoding such products, expression vectors and transformed yeast cells. The invention further relates to aprotinin analogs, compositions comprising such analogs.

2. BACKGROUND OF THE INVENTION

Aprotinin (also known as bovine pancreatic trypsin inhibitor, BPTI) is a basic protein present in several bovine organs and tissues, such as the lymph nodes, pancreas, lungs, parotid gland, spleen and liver. It is a single-chain polypeptide of 58 amino acid residues with the following amino acid sequence Arg Pro Asp Phe Cys Leu Glu Pro Pro Tyr Thr Gly Pro Cys Lys Ala Arg Ile Ile Arg Tyr Phe Tyr Asn Ala Lys Ala Gly Leu Cys Gln Thr Phe Val Tyr Gly Gly Cys Arg Ala Lys Arg Asn Asn Phe Lys Ser Ala Glu Asp Cys Met Arg Thr Cys Gly Gly Ala (SEQ ID NO:1).

The amino acid chain is cross-linked by three disulphide bridges formed between Cys(5) and Cys(55), Cys(14) and Cys(38) and Cys(30) and Cys(51), respectively.

The isoelectric point of aprotinin is quite high (approximately 10.5). This is mainly caused by a relatively high content of the positively charged amino acids lysine and arginine. The three-dimensional structure of the aprotinin molecule is very compact which makes it highly stable against denaturation at high temperatures, or by acids, alkalis or organic solvents, or against proteolytic degradation (cf. B. Kassell, *Meth. Enzym.* 19, 1970, pp. 844–852).

Aprotinin is known to inhibit various serine proteases, including trypsin, chymotrypsin, plasmin and kallikrein, and is used therapeutically in the treatment of acute pancreatitis, various states of shock syndrome, hyperfibrinolytic hemorrhage and myocardial infarction (cf., for instance, J. E. Trapnell et al, *Brit. J. Surg.* 61, 1974, p. 177; J. McMichan et al., *Circulatory shock* 9, 1982, p. 107; L. M. Auer et al., *Acta Neurochir.* 49, 1979, p. 207; G. Sher, *Am. J. Obstet. Gynecol,* 129, 1977, p. 164; and B. Schneider, *Artzneim.-Forsch.* 26, 1976, p. 1606). Administration of aprotinin in high doses significantly reduces blood loss in connection with cardiac surgery, including cardiopulmonary bypass operations (cf., for instance, B. P. Bidstrup et al., *J. Thorac. Cardiovasc. Surg.* 97, 1989, pp. 364–372; W. van Oeveren et al., *Ann. Thorac. Surg.* 44, 1987, pp. 640–645).

2.1. PRODUCTION OF APROTININ

Aprotinin, hereinafter referred to as "native aprotinin" can be extracted from various bovine organs or tissues, such as lung, pancreas and parotid glands. Extraction from animal tissues is a cumbersome process and requires large amounts of the bovine organ or tissue.

A gene for aprotinin has been fused to the coding sequence for *E. coli* alkaline phosphatase signal peptide and expressed in *E. coli* under the control of the alkaline phosphatase promoter (Marks et al., 1986, J. Biol. Chem. 261:7115–7118). Also, a synthetic gene encoding the protein sequence of Met-aprotinin has been cloned in an *E. coli* expression vector (von Wilcken-Berman et al., 1986, EMBO J. 5:3219–3225).

However, it has been found that a small protein such as aprotinin is likely to be degraded by the host proteases. Furthermore, it has been found to be difficult to establish correct disulphide bridges and correct folding in *E. coli*.

2.2. APROTININ ANALOGS

Certain aprotinin analogs are known, e.g. from U.S. Pat. No. 4,595,674 disclosing aprotinin analogs and derivatives wherein Lye(15) is replaced with Gly, Ala, Val, Leu, Ils, Met, Arg, L-α-butyric acid,. L-norvaline, L-norleucine, dehydroalanine or L-homoserine. EP 238 993 discloses aprotinin analogs wherein Lys (15) is replaced with Arg, Val, Ile, Leu, Phe, Gly, Ser, Trp, Tyr or Ala, and wherein Met (52) is furthermore replaced with Glu, Val, Leu, Thr or Ser. EP 307 592 discloses aprotinin analogs wherein one or more of the amino acids in position 15, 16, 17, 18, 34, 39 and 52 are replaced with another amino acid residue. In position 17, the amino acid is preferably Leu, Arg, Ils or Val. Marks et al., 1987, Science 235:1370–1373 describes mutants of aprotinin which are substituted by Ala or Thr in positions 14 and 38. It is reported that these mutants were expressed in *E. coli* and properly folded.

The known aprotinin analogs are claimed to have modified effects and efficacies towards different proteinases. For instance, aprotinin(15Val) has a relatively high selectivity for granulocyte elastase and an inhibitory effect on elastase and aprotinin (15Gly) has an outstanding antitrypsin activity and surprisingly inhibits kallikrein.

2.3. TOXICITY OF APROTININ

It has previously been described that after intravenous injection of native aprotinin in animals or human volunteers, the plasma level of the inhibitor decreases rather quickly owing to distribution in the extracellular fluid and subsequently accumulation in the kidneys (I. Trautschold et al., in K. Heinkel and H. Schön (Eds.): *Pathogenese: Diagnostik: Klinik und Therapie der Erkrankungen des Exokrinen Pankreas,* Schattauer, Stuttgart, 1964, p. 289; E. Habermann et al., *Med. Welt* 24(29), 1973, pp. 1163–1167; H. Fritz et al., *Hoppe-Seylers Z. Physiol. Chem.* 350, 1969, pp. 1541–1550; and H. Kaller et al., *Eur. J. Drug Metab. Pharmacokin,* 2, 1978, pp. 79–85). Following glomerulus filtration, aprotinin is almost quantitatively bound to the brush border membrane of the proximal tubulus cells. Aprotinin is then reabsorbed into micropinocytic vesicles and phagosomes followed by a very slow degradation in phagolysosomes. This type of transport has been suggested to be representative for peptides in general (M. Just and E. Habermann, *Naynyn-Scmiedebergs Arch. Pharmacol.* 280, 1973, pp. 161–176; M. Just, *Naynyn-Schmiedebergs Arch. Pharmacol.* 287, 1975, pp. 85–95).

Macroscopic and histopathological examination following administration of aprotinin reveal changes in the renal tissues of rats, rabbits and dogs after repeated injections of relatively high doses of aprotinin (Bayer, *Trasylol, Inhibitor of proteinase;* E. Glaser et al. in "Verhandlungen der Deutschen Gesellschaft für Innere Medizin, 78. Kongress", Bergmann, München, 1972, pp. 1612–1614). The nephrotoxicity (i.a. appearing in the form of lesions) observed for aprotinin might be ascribable to the accumulation of aprotinin in the proximal tubulus cells of the kidneys. This nephrotoxicity makes aprotinin less suitable for clinical purposes, in particular those requiring administration of large doses of the inhibitor (such as cardiopulmonary bypass operations).

3. OBJECTS OF THE INVENTION

It would be commercially advantageous to develop a method for producing high yields of properly folded aprotinin or aprotinin analogs in mature form.

Furthermore, it would be beneficial to obtain aprotinin analogs which have a more specific inhibitory effect towards certain serine proteases, such as elastase, kallikrein, t-PA, urokinase and coagulation factors, such as thrombin compared to native aprotinin.

It would also be commercially beneficial to produce aprotinin analogues with a reduced nephrotoxicity compared to native aprotinin.

4. SUMMARY OF THE INVENTION

The invention is directed to a method for producing high yields of aprotinin or analogs thereof. In a preferred embodiment, the aprotinin or aprotinin analog is produced in yeast by cultivation of a yeast strain containing a replicable expression vector containing a synthetic gene encoding aprotinin or analog thereof in a suitable nutrient medium followed by recovery of the aprotinin or analog thereof from the culture medium. The aprotinin produced by the present invention can be characterized by the following formula $$X\text{-aprotinin}(3\text{-}40)\text{-}Y_n\text{-}Z_m\text{-aprotinin}(43\text{-}58)$$

in which X means Arg-Pro, Pro or hydrogen, aprotinin(3-40) means the amino acid sequence from amino acid residue 3 to 40 in native aprotinin, Y may be Lys, or a non-basic amino acid residue, e.g., Ser, Thr or Ala, Z may be Arg, or a non basic amino acid residue, e.g. Ser, Thr or Ala, n and m are each 0 or 1, and aprotinin(43-58) means the amino acid sequence from amino acid residue 43 to 58 in native aprotinin.

The present invention is also directed to a DNA sequence comprising a synthetic gene encoding aprotinin or analog thereof.

The invention is also directed to a replicable expression vector comprising a DNA sequence or gene encoding aprotinin or analog thereof and a DNA sequence that allows for the expression of the aprotinin or analog thereof in yeast. The invention further provides a yeast strain transformed with such a vector.

The present invention is also related to novel aprotinin analogs. In one embodiment, the aprotinin analogs have a more specific inhibitory effect towards certain serine proteases such as elastase, kallikrein, t-PA, urokinase and coagulation factors such as thrombin than native protein.

In a specific embodiment, the aprotinin analog has the formula as set forth in the Sequence Listing as SEQ ID NO:2.

$$X_1\text{—Asp—Phe—Cys—Leu—Glu—Pro—Pro—Tyr—Thr—}X_2\text{—}X_3\text{—}X_4\text{—}X_5\text{—}X_6\text{—}X_7\text{—}X_8\text{—} \quad \text{(I)}$$
$$X_9\text{—Arg—Tyr—Phe—Tyr—Asn—Ala—Lys—Ala—Gly—Leu—Cys—Gln—Thr—Phe—}$$
$$\text{Val—Tyr—Gly—Gly—}X_{10}\text{—Arg—Ala—}X_{11}\text{—}X_{12}\text{—Asn—Asn—Phe—Lys—Ser—}$$
$$\text{Ala—Glu—Asp—Cys—Met—Arg—Thr—Cys—Gly—Gly—Ala}$$

in which $X_1$ is Arg-Pro, Pro or hydrogen; $X_2$ and $X_3$ are independently any naturally occurring amino acid residue; $X_4$ and $X_{10}$ are both Cys; $X_5$ is nys, Arg, Val, Thr, Ile, Leu, Phe, Gly, Ser, Met, Trp, Tyr or Ala; $X_6$ is Ala or Gly; $X_7$ is Ala or Gly; $X_8$ is Ile, Leu, Met, Val or Phe; $X_9$ is any naturally occurring amino acid residue; $X_{11}$ is any naturally occurring amino acid residue; $X_{12}$ is Lys, Arg or Ser, provided that $X_7$ is Ala or Gly and each of $X_2$-$X_6$ and $X_8$-$X_{12}$ is different from the corresponding amino acid residue in native aprotinin.

In another specific embodiment, the aprotinin analog has the formula as set forth in the Sequence Listing as SEQ ID No:2.

$$X_1\text{—Asp—Phe—Cys—Leu—Glu—Pro—Pro—Tyr—Thr—}X_2\text{—}X_3\text{—}X_4\text{—}X_5\text{—}X_6\text{—}X_7\text{—}X_8\text{—} \quad \text{(II)}$$
$$X_9\text{—Arg—Tyr—Phe—Tyr—Asn—Ala—Lys—Ala—Gly—Leu—Cys—Gln—Thr—Phe—}$$
$$\text{Val—Tyr—Gly—Gly—}X_{10}\text{—Arg—Ala—}X_{11}\text{—}X_{12}\text{—Asn—Asn—Phe—Lys—Ser—Ala—}$$
$$\text{Glu—Asp—Cys—Met—Arg—Thr—Cys—Gly—Gly—Ala}$$

in which $X_1$ is Pro or hydrogen; $X_2$ and $X_3$ are independently any naturally occurring amino acid residue; $X_4$ and $X_{10}$ are both Cys; $X_5$ is Lys, Arg, Val, Thr, Ile, Leu, Phe, Gly, Ser, Met, Try, Tyr or Ala; $X_6$ is Ala or Gly; $X_7$ is any naturally occuring amino acid residue; $X_8$ is Ile, Leu, Met, Val or Phe; $X_9$ is any naturally occurring amino acid residue; $X_{11}$ is any naturally occurring amino acid residue; $X_{12}$ is Lys, Arg or Ser, provided that $X_1$ is Pro or hydrogen and at least one of the amino acid residues $X_2$ to $X_9$ is different from the corresponding amino acid residue in native aprotinin.

In another embodiment, the present invention further relates to an aprotinin analog with reduced nephrotoxicity compared to native aprotinin. In a preferred embodiment, such an analog has a reduced net positive charge and reduced stability compared to native aprotinin. To provide a reduced positive net charge, at least one positively charged amino acid residue outside the protease-binding site is removed or replaced with a neutral or negatively charged amino acid residue, and/or at least one negatively charged amino acid residue is inserted or added, and/or wherein at least one neutral amino acid residue is replaced with a negatively charged amino acid residue. To provide reduced stability, one or more amino acid residues are deleted, added or replaced with one or more other amino acid residues. In a specific embodiment, the aprotinin analog has the following formula $$X'\text{-aprotinin}(3\text{-}40)\text{-}Y'_n\text{-}Z'_m\text{-aprotinin (43-58)}$$

in which X' means Pro or hydrogen, aprotinin(3-40) means the amino acid sequence from amino acid residue 3 to 40 in native aprotinin, Y' is Lys or a non-basic amino acid residue, Z' may be Arg or a non-basic amino acid residue with the proviso that at least Y' or Z' is a non-basic amino acid residue, n and m are each 0 or 1, and aprotinin(43-58) means the amino acid sequence from amino acid residue 43 to 58 in native aprotinin.

In the present context, the term "reduced positive net charge" is understood to include analogues with a lower positive net charge than that of native aprotinin (which has a positive net charge of +6) as well as with no net charge or a negative net charge. It should be noted that the net charge of aprotinin may vary according to pH, and that the terms "positive net charge", "negative net charge", "positively charged" or "negatively charged" are used about the charge of the molecule at a neutral pH.

The term "protease-binding site" is intended to indicate the amino acid residues which are important for protease inhibition, i.e. the amino acid residues which are in intimate contact with the protease by binding to amino acid residues at or close to the active site of the enzyme. These are currently understood to include (and are, in the present context defined as) the amino acid residues in position 12-18 and 34-39 (cf. H. Fritz and G. Wunderer, *Artzneim.-Forsch.* 33(1), 1983, p. 484). It is preferred to remove, insert or replace amino acid residues outside the protease-binding site only in order to avoid substantially changing the protease inhibition profile of the analogue of the invention compared to that of native aprotinin.

5. BRIEF DESCRIPTION OF THE DRAWINGS

The present invention will be further illustrated by reference to the accompanying drawings in which:

FIG. 1 shows a synthetic gene encoding aprotinin (3-58).

FIG. 5 shows a synthetic gene encoding aprotinin (3-58; 42 Ser).

FIG. 10 shows the construction of a synthetic aprotinin gene from oligonucleotide sequences.

FIG. 16 shows a synthetic gene encoding aprotinin(1-58).

FIG. 17 shows a synthetic gene encoding aprotinin(1-58, 42 Ser).

6. DETAILED DESCRIPTION OF THE INVENTION

Figure 2:
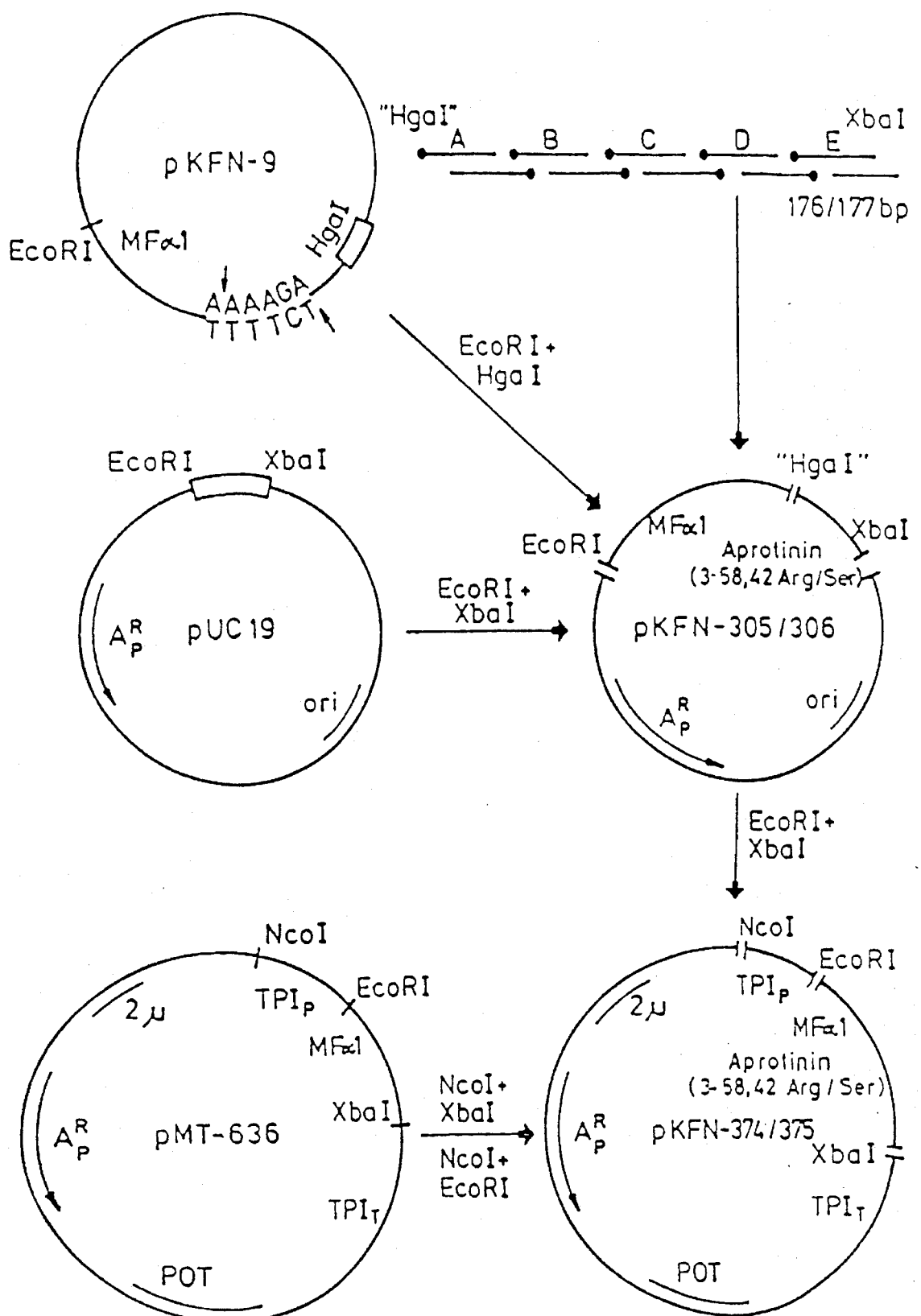
FIG. 2 illustrates the construction of plasmids pKFN374 and pKFN375.

The invention is related to a method for producing high yields of aprotinin or analogs thereof, as well as genes encoding aprotinin and analogs thereof, vectors comprising such genes, and host cells capable of expressing the genes. The invention is directed to novel aprotinin analogs, specifically analogs having a more specific inhibitory effect towards certain serine proteases and analogs having a reduced nephrotoxicity compared to native aprotinin, as well as pharmaceutical compositions comprising such novel analogs.

6.1. PRODUCTION OF APROTININ AND APROTININ ANALOGS

Aprotinin and the aprotinin analogs of the present invention may be obtained by recombinant DNA methods known in the art exemplified below and described in the examples herein. A DNA construct is prepared comprising a gene encoding aprotinin or an analog thereof.

The DNA construct may be prepared synthetically by established standard methods, e.g. the phosphoramidite method described by S. L. Beaucage and M. H. Caruthers, *Tetrahedron Letters* 22, 1981, pp. 1859–1869, or the method described by Matthes et al., *EMBO Journal* 3, 1984, pp. 801–805. According to the phosphoramidite method, oligonucleotides are synthesized, e.g. in an automatic DNA synthesizer, purified, annealed, ligated and cloned in suitable vectors.

Alternatively, it is possible to use genomic or cDNA coding for native aprotinin (e.g. obtained by screening a genomic or cDNA library using synthetic oligonucleotide probes) and modified at one or more sites corresponding to the site(s) at which it is desired to introduce amino acid substitutions, e.g. by site-directed mutagenesis using synthetic oligonucleotides encoding the desired amino acid sequence for homologous recombination in accordance with well-known procedures.

A vector which comprises the DNA construct and is capable of expressing the gene encoding the aprotinin or analog thereof in a host cell is any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In a preferred embodiment, the vector is capable of replicating in yeast cells. As will be detailed in the Examples herein, aprotinin and aprotinin analogs can surprisingly be produced in high yields with correctly positioned disulphide bridges by cultivation of a yeast cell transformed with a gene encoding such products.

The gene encoding aprotinin or an aprotinin analog in the vector should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA encoding the aprotinin or aprotinin analog are the SV 40 promoter (Subramani et al., *Mol. Cell Biol.* 1, 1981, pp. 854–864), the MT-1 (metallothionein gene) promoter (Palmiter et al., *Science* 222, 1983, pp. 809–814) or the adenovirus 2 major late promoter. Suitable promoters for use in yeast host cells include promoters from yeast glycolytic genes (Hitzeman et al., *J. Biol. Chem.* 255, 1980, pp. 12073–12080; Alber and Kawasaki, *J. Mol. Appl. Gen.* 1, 1982, pp. 419–434) or alcohol dehydrogenase genes (Young et al., in *Genetic Engineering of Microorganisms for Chemicals* (Hollaender et al, eds.), Plenum Press, New York, 1982), or the TPI1 (U.S. Pat. No. 4,599,311) or ADH2-4c (Russell et al., *Nature* 304, 1983, pp. 652–654) promoters. Suitable promoters for use in filamentous fungus host cells are, for instance, the ADH3 promoter (McKnight et al., *The EMBO J.* 4, 1985, pp. 2093–2099) or the tpiA promoter.

For secretion purposes, the DNA sequence encoding the desired aprotinin or aprotinin analog may be fused to a DNA sequence encoding a signal and leader peptide sequence. The signal and leader peptides are cleaved off by the transformed microorganism during the secretion of the expressed protein product from the cells ensuring a more simple isolation procedure of the desired product. A well suited leader peptide system for yeast is the yeast MFαl leader sequence or a part thereof (Kurjan, J. and Herskowitz, I., Cell 30 (1982) 933–943) or a leader described in Danish patent application No. 4638/87. However, any signal- or leader-sequence which provides for secretion in yeast may be employed and the present invention is not contemplated to be restricted to a specific secretion system.

The DNA sequence encoding the aprotinin analogue of the invention may also be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) promoters. The vector may further comprise elements such as polyadenylation signals (e.g. from SV 40 or the adenovirus 5 Elb region), transcriptional enhancer sequences (e.g. the SV 40 enhancer) and translational enhancer sequences (e.g. the ones encoding adenovirus VA RNAs).

The vector of the invention may further comprise a DNA sequence enabling the vector to replicate in the host cell in question. Examples of such a sequence (when the host cell is a mammalian cell) is the SV 40 origin of replication, or (when the host cell is a yeast cell) the yeast plasmid 2μ replication genes REP 1-3 and origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hygromycin or methotrexate, or the *Schizosaccharomyces pombe* TPI gene (described by P. R. Russell, *Gene* 40, 1985, pp. 125–130).

The procedures used to ligate the DNA sequences coding for the aprotinin or aprotinin analog, the promoter, and the terminator, respectively, and to insert them into suitable vectors containing the information necessary for replication, are well known to persons skilled in the art (cf., for instance, Sambrook et al., *Molecular Cloning: A Laboratory Manual*, Cold Spring Harbor, New York, 1989).

The host cell into which the vector of the invention is introduced may be any cell which is capable of producing aprotinin or an aprotinin analog and is preferably a eukaryotic cell, such as a mammalian, yeast or fungal cell.

Examples of suitable mammalian cell lines are the COS (ATCC CRL 1650), BHK (ATCC CRL 1632, ATCC CCL 10) or CHO (ATCC CCL 61) cell lines. Methods of transfecting mammalian cells and expressing DNA sequences introduced in the cells are described in e.g. Kaufman and Sharp, *J. Mol. Biol.* 159, 1982, pp. 601–621; Southern and Berg, *J. Mol. Appl. Genet.* 1, 1982, pp. 327–341; Loyter et al., *Proc. Natl. Acad. Sci. USA* 79, 1982, pp. 422–426; Wigler et al., *Cell* 14, 1978, p. 725; Corsaro and Pearson, *Somatic Cell Genetics*, 7, 1981, p. 603, Graham and van der Eb, *Virology* 52, 1973, p. 456; and Neumann et al., *EMBO J.* 1, 1982, pp. 841–845.

In a preferred embodiment, the yeast organism used as the host cell according to the invention may be any yeast organism which, on cultivation, produces large quantities of the aprotinin analog of the invention. Examples of suitable yeast organisms are strains of the yeast species *Saccharomyces cerevisiae, Saccharomyces kluyveri, Schizosaccharomyces pombe* or *Saccharomyces uvarum*. The transformation of yeast cells may for instance be effected by protoplast formation followed by transformation in a manner known per se. The methods for transformation of yeast and cultivation of transformed yeast strains that can be used in the practice of the invention are those known in the art such as those described in the above mentioned EP patent application Nos. 0163529A and 0189998A.

Alternatively, fungal cells may be used as host cells of the invention. Examples of suitable fungal cells are cells of filamentous fungi, e.g. Aspergillus spp. or Neurospora spp., in particular strains of *Aspergillus oryzae* or *Aspergillus niger*. The use of Aspergillus spp. for the expression of proteins is described in, e.g., EP 272 277.

The medium used to cultivate the cells may be any conventional medium suitable for growing mammalian cells or yeast organisms, depending on the choice of host cell. The aprotinin or aprotinin analog will be secreted by the host cells to the growth medium and may be recovered therefrom by conventional procedures including separating the cells from the medium by centrifugation or filtration, precipitating the proteinaceous components of the supernatant or filtrate by means of a salt, e.g. ammonium sulfate, purification by a variety of chromatographic procedures, e.g. ion exchange chromatography or affinity chromatography, or the like.

6.2. ANALOGS HAVING A MORE SPECIFIC INHIBITORY EFFECT TOWARDS CERTAIN SERINE PROTEASES

The present aprotinin analogs may be represented by the formula as set forth in the Sequence Listing as SEQ ID NO:2 and in Formulae I and II (see Section 4, supra).

According to a more narrow aspect, the present aprotinin analogs may be represented by the following formula set forth in the Sequence Listing as SEQ ID NO:3:

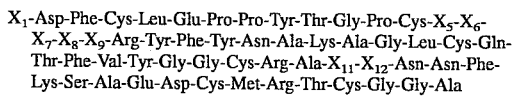

in which $X_1$, $X_5$, $X_6$, $X_7$, $X_8$, $X_9$, $X_{11}$ and $X_{12}$ are as defined above for SEQ ID NO:2, at least one of the amino acid residues $X_5$ to $X_9$, preferably $X_6$ to $X_9$ being different from the corresponding amino acid residue in native aprotinin.

According to an even narrower aspect the aprotinin analogues may be represented by the following formula set forth in the Sequence Listing as SEQ ID NO:4:

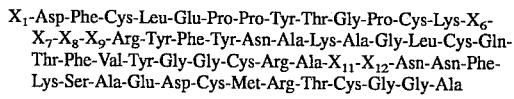

in which $X_1$, $X_6$, $X_7$, $X_8$, $X_9$, $X_{11}$ and $X_{12}$ are as defined above for SEQ ID NO:2, at least one of the amino acid residues $X_6$ to $X_9$ being different from the corresponding amino acid residue in native aprotinin.

In the sequence represend by formula I or II above, $X_1$ is preferably hydrogen; $X_2$ is preferably Gly; $X_3$ is preferably Pro; $X_5$ is preferably Lys or Arg; $X_6$ is preferably Ala; $X_7$ is preferably Ala; $X_8$ is preferably Ile; $X_9$ is preferably Ile; $X_{11}$ is preferably Lys; and/or $X_{12}$ is preferably Arg or Ser.

Examples of preferred aprotinin analogs according to the present invention are aprotinin (3-58; 17 Ala+42 Ser; SEQ ID NO:5) which lacks the first two amino acid residues of native aprotinin and has Ala substituted for Arg in position 17 and Ser substituted for Arg in position 42; aprotinin (3-58; 17 Ala+19 Glu+42 Ser; SEQ ID NO:6) which lacks the first two amino acid residues of native aprotinin and has Ala substituted for Arg in position 17, Glu substituted for Ile in position 19 and Ser substituted for Arg in position 42; and aprotinin (3-58; 15 Arg+17 Ala+42 Ser; SEQ ID NO:7) which lacks the first two amino acid residues of native aprotinin and has Arg substituted for Lys in position 15, Ala substituted for Arg in position 17 and Ser substituted for Arg in position 42, respectively.

Further examples of aprotinin analogs to the present invention are:
Aprotinin (3-58; 17 Ala) (SEQ ID NO:8)
Aprotinin (3-58; 17 Ala+19 Glu) (SEQ ID NO:9)
Aprotinin (3-58; 15 Arg+17 Ala) (SEQ ID NO:10)
Aprotinin (17 Ala+42 Ser) (SEQ ID NO:11)
Aprotinin (15 Arg+17 Ala+42 Ser) (SEQ ID NO:12)
Aprotinin (17 Ala) (SEQ ID NO:13)
Aprotinin (17 Ala+19 Glu) (SEQ ID NO:14)
Aprotinin (15 Arg+17 Ala) (SEQ ID NO:15)

6.3. APROTININ ANALOGS WITH REDUCED NEPHROTOXICITY

The invention is also directed to aprotinin analogs having reduced nephrotoxicity compared to native aprotinin. In a specific embodiment, such analogs have a reduced positive charge and reduced stability.

According to the invention, any of the positively charged amino acid residues outside the protease-binding site might be replaced with either the negatively charged amino acid residues Glu or Asp or with any one of the neutral amino acid residues Ala, Cys, Phe, Gly, His, Ile, Leu, Met, Asn, Pro, Glu, Ser, Thr, Val, Trp or Tyr. However, in order to avoid inactive analogs or analogs with an inappropriate three-dimensional structure arising from an undesired folding of the molecule, it is preferred to select substitutions which are identical to amino acid residues in corresponding positions of other protease inhibitors or in domains of larger structures exhibiting a high degree of homology to native aprotinin. In other words, the selection of substituent amino acid residues is preferably based on an analysis of molecules which are homologous to aprotinin. It should be noted that, concomitantly with the amino acid substitution(s) directly contributing to a reduction in the positive net charge, one or more other amino acid substitutions may be carried out which do not in themselves result in a reduced positive net charge, but which may be required in order to produce an active analogue with an appropriate three-dimensional structure.

Accordingly, in a more specific aspect, the present invention relates to an aprotinin analog having the following formula set forth in the Sequence Listing as SEQ ID NO:16:

$X_1$ Asp Phe Cys Leu Glu Pro Pro $X_2$ Thr Gly Pro Cys Lys Ala

Arg Ile Ile $X_3$ Tyr Phe Tyr $X_4$ Ala $X_5$ Ala Gly Leu Cys $X_6$ Thr

Phe Val Tyr Gly Gly Cys Arg $X_7$ $X_8$ $X_9$ Asn $X_{10}$ Phe $X_{11}$ Ser Ala

Glu Asp Cys Met $X_{12}$ Thr Cys Gly Gly Ala wherein $X_1$ is an amino acid residue selected from the group consisting of Tyr, Glu, Asp, Ser, Thr, Ala and Val, $X_2$ is an amino acid residue selected from the group consisting of Tyr, Glu, Asp, Ser, Thr, Ala and Val, $X_3$ is an amino acid residue selected from the group consisting of Arg, Glu, Asp, Leu, Ser, Ala, Gln and Thr, $X_4$ is an amino acid residue selected from the group consisting of Asn, Glu and Asp, $X_5$ is an amino acid residue selected from the group consisting of Lys, Glu, Asp, Thr, Val, Ala, Ser, Phe, Gln and Gly, $X_6$ is an amino acid residue selected from the group consisting of Gln, Glu, Asp, Val and Ala, $X_7$ is an amino acid residue selected from the group consisting of Ala, Asp, Glu and Gly, $X_8$ is an amino acid residue selected from the group consisting of Lys, Glu, Asp, Asn, Ser, Thr and Ala, $X_9$ is an amino acid residue selected from the group consisting of Arg, Glu, Asp, Ser, Asn, Leu, Gly, Gln, Met and Thr, $X_{10}$ is an amino acid residue selected from the group consisting of Asn, Glu and Asp, $X_{11}$ is an amino acid residue selected from the group consisting of Lys, Glu, Asp, Leu, Tyr, Ala, Val, Thr, Ser, Pro, His and Ile, and $X_{12}$ is an amino acid residue selected from the group consisting of Arg, Glu, Asp, Gln, Ala, Asn, His, Gly, Ser and Thr, with the proviso that at least one of the amino acid residues $X_1$-$X_2$ is different from the corresponding amino acid residue of native aprotinin.

Apart from these internal substitutions in the aprotinin molecule, it may be possible to add a peptide containing one or more negatively charged amino acid residues (i.e. Glu or Asp) at the N- or C-terminal end of the aprotinin molecule in order to provide the requisite reduction in the positive net charge. It may further be possible, in order to provide a reduction in the stability of the molecule, to add one or more neutral amino acid residues to the N- or C-terminal end of the molecule. Such additions may be done either to the native aprotinin molecule or in addition to other modifications as indicated above.

If it is desired to change the protease inhibition properties of the aprotinin analogue apart from reducing its nephrotoxicity, it is possible additionally to modify the analog in the protease-binding site. For instance, it has previously been demonstrated (cf. H. R. Wenzel and H. Tschesche, *Angew. Chem. Internat. Ed.* 20, 1981, p. 295) that aprotinin(1-58, Val15) exhibits a relatively high selectivity for granulocyte elastase and an inhibitory effect on collagenase, aprotinin (1-58, Ala15) has a weak effect on elastase, and aprotinin (1-58, Gly15) exhibits an outstanding antitrypsin activity and surprisingly also inhibits kallikrein. Furthermore, it may be possible to modify the inhibitory effect of aprotinin concomitantly with reducing the positive net chargeby replacing one or more positively charged amino acids in the protease-binding site by neutral or negatively charged amino acid(s).

Thus, the present invention further relates to an aprotinin analog having the following formula set forth in the Sequence Listing as SEQ ID NO:17:

$X_1$ Asp Phe Cys Leu Glu Pro Pro $X_2$ Thr Gly Pro Cys $X_{13}$ $X_{14}$ $X_{15}$ $X_{16}$ $X_{17}$ $X_3$ Tyr Phe Tyr $X_4$ Ala $X_5$ Ala Gly Leu Cys $X_6$ Thr Phe $X_{18}$ Tyr $X_{19}$ Gly Cys $X_{20}$ $X_7$ $X_8$ $X_9$ Asn $X_{10}$ Phe $X_{11}$ Ser Ala Glu Asp Cys Met $X_{12}$ Thr Cys Gly Gly Ala wherein $X_1$-$X_2$ are as defined above, $X_{13}$ is an amino acid residue selected from the group consisting of Lys, Arg, Glu, Leu, Met, Tyr and Phe, $X_{14}$ is an amino acid residue selected from the group consisting of Ala and Gly, $X_{15}$ is an amino acid residue selected from the group consisting of Arg, Ala, Gly, Lys, Leu, Met, Phe, Tyr, Ile and Asn, $X_{16}$ is an amino acid residue selected from the group consisting of Ile, Met, Leu, Phe, Thr and Glu, $X_{17}$ is an amino acid residue selected from the group consisting of Ile, Leu, Lys, Gln, Glu, Ser, Arg, Thr and Asn, $X_{18}$ is an amino acid residue selected from the group consisting of Val, Thr, Leu, Ser, Tyr, Gln, His, Pro, Phe, Asn, Ile and Lys, $X_{19}$ is an amino acid residue selected from the group consisting of Gly, Thr and Ser, and $X_{20}$ is an amino acid residue selected from the group consisting of Gln, Lys, Met, Asn, Leu, Gly and Glu, with the proviso that at least one of the amino acid residues $X_1$-$X_{12}$ and at least one of the amino acid residues $X_{13}$-$X_{20}$ are different from the corresponding amino acid residue of native aprotinin.

Examples of currently favored aprotinin analogs of the general formula (SEQ ID NO: 16) include an analog wherein $X_1$ is Glu-Pro, $X_5$ is Glu, $X_8$ is Glu, $X_{11}$ is Glu, and $X_2$, $X_3$, $X_4$, $X_6$, $X_7$, $X_9$, $X_{10}$ and $X_{12}$ are as in the native aprotinin sequence; or wherein $X_1$ is Glu-Pro, $X_9$ is Glu, $X_{11}$ is Glu, and $X_2$, $X_3$, $X_4$, $X_6$, $X_7$, $X_8$, $X_{10}$ and $X_{12}$ are as in the native aprotinin sequence; or wherein $X_9$ is Glu, $X_{11}$ is Glu, and $X_1$, $X_2$, $X_3$, $X_4$, $X_5$, $X_6$, $X_7$, $X_8$, $X_{10}$ and $X_{12}$ are as in the native aprotinin sequence; or wherein $X_2$ is Ser, $X_4$ is Asp, $X_5$ is Thr, $X_6$ is Glu, $X_8$ is Asn, $X_{12}$ is Glu, and $X_1$, $X_3$, $X_7$, $X_9$, $X_{10}$, and $X_{11}$ are as in the native aprotinin sequence; or wherein $X_2$ is Ser, $X_3$ is Leu, $X_7$ is Gly, $X_8$ is Asn, $X_9$ is Gly, $X_{10}$ is Gln, $X_{11}$ is Tyr, and $X_1$, $X_4$, $X_5$, $X_6$, and $X_{12}$ are as in the native aprotinin sequence; or wherein $X_1$ is a peptide bond, $X_9$ is Ser, $X_{11}$ is Glu, and $X_2$, $X_3$, $X_4$, $X_5$, $X_6$, $X_7$, $X_8$, $X_{10}$ and $X_{12}$ are as in the native aprotinin sequence or wherein $X_1$ is a peptide bond, $X_9$ is Ser, $X_{11}$ is Ala, and $X_2$, $X_3$, $X_4$, $X_5$, $X_6$, $X_7$, $X_8$, $X_{10}$ and $X_{12}$ are as in the native aprotinin sequence; or wherein $X_1$ is a peptide bond, $X_2$ is Ser, $X_4$ is Asp, $X_5$ is Thr, $X_6$ is Glu, $X_8$ is Ash, $X_{12}$ is Glu, and $X_3$, $X_7$, $X_9$, $X_{10}$ and $X_{11}$ are as in the native aprotinin sequence; or wherein $X_1$ is a peptide bond, $X_4$ is Asp, $X_5$ is Thr, $X_6$ is Glu, $X_{12}$ is Glu, and $X_2$, $X_3$, $X_7$, $X_8$, $X_9$, $X_{10}$ and $X_{11}$ are as in the native aprotinin sequence; or wherein $X_1$ is a peptide bond, $X_2$ is Ser, $X_7$ is Gly, $X_8$ is Ash, $X_9$ is Gly, $X_{12}$ is Glu, and $X_3$, $X_4$, $X_5$, $X_6$, $X_{10}$ and $X_{11}$ are as in the native aprotinin sequence; or wherein $X_1$ is a peptide bond, $X_9$ is Ser, $X_{12}$ is Glu, and $X_2$, $X_3$, $X_4$, $X_5$, $X_6$, $X_7$, $X_8$, $X_{10}$ and $X_{11}$ are as in the native aprotinin sequence; or wherein $X_1$ is a peptide bond, $X_9$ is Glu, $X_{12}$ is Glu, and $X_2$, $X_3$, $X_4$, $X_5$, $X_6$, $X_7$, $X_8$, $X_{10}$ and $X_{11}$ are as in the native aprotinin sequence; or wherein $X_1$ is a peptide bond, $X_5$ is Glu, $X_9$ is Ser, $X_{12}$ is Glu, and $X_2$, $X_3$, $X_4$, $X_6$, $X_7$, $X_8$, $X_{10}$ and $X_{11}$ are as in the native aprotinin sequence; or wherein $X_1$ is a peptide bond, $X_5$ is Glu, $X_9$ is Glu, $X_2$ is Glu, and $X_2$, $X_3$, $X_4$, $X_6$, $X_7$, $X_8$, $X_{10}$ and $X_{11}$ are as in the native aprotinin sequence.

In another embodiment, the aprotinin analogs of the present invention have the formula $$X'\text{-aprotinin}(3\text{-}40)\text{-}Y'_n\text{-}Z'_m\text{-aprotinin}(43\text{-}58)$$

in which X' means Pro or hydrogen, aprotinin(3-40) means the amino acid sequence from amino acid residue 3 to 40 in native aprotinin, Y' is Lys or a non-basic amino acid residue, Z' may be Arg or a non-basic amino acid residue with the proviso that at least Y' or Z' is a non-basic amino acid residue, n and m are each 0 or 1, and aprotinin(43-58) means the amino acid sequence from amino acid residue 43 to 58 in native aprotinin.

6.4. USES FOR APROTININ ANALOGS

The analogs of the present invention as a result of their inhibition of human serine proteases may be used to treat acute pancreatitis, inflammation, thrombocytopenia, preservation of platelet function, organ preservation, wound healing, shock (including shock lung) and conditions involving hyperfibrinolytic hemorrhage. A high dose of aprotinin is indicated during and after cardiopulmonary bypass operations. The aprotinin analogs of the present invention having a lower nephrotoxicity is of particular interest for this application and possibly in other surgery involving a major loss of blood, as is the possibly reduced risk of causing anaphylactoid response due to the lower positive net charge of the analog.

The analogs of the present invention may be formulated in a pharmaceutical composition with an acceptable carrier. The pharmaceutical carriers may be such physiologically compatible buffers as Hank's or Ringer's solution, physiological saline, a mixture consisting of saline and glucose, and heparinized sodium-citrate-citric acid-dextrose solution. The aprotinin analogs of the present invention produced by the methods of the present invention can be mixed with colloidal-like plasma substitutes and plasma expanders such as linear polysaccharides (e.g. dextran), hydroxyethyl starch, balanced fluid gelatin, and other plasma proteins. Additionally, the aprotinin analogs may be mixed with water soluble, physiologically acceptable, polymeric plasma substitutes, examples of which include polyvinyl alcohol, poly-(ethylene oxide), polyvinylpyrrolidone, and ethylene oxide-polypropylene glycol condensates. Techniques and formulations for administering the compositions comprising the aprotinin analogs generally may be found in Remington's Pharmaceutical Sciences, Meade Publishing Col., Easton, Pa., latest edition.

The following examples are offered by way of illustration and not byway of limitation.

7. EXAMPLES

7.1. EXAMPLE 1: PRODUCTION OF APROTININ(3-58)

A sequence encoding aprotinin (3-58) was constructed from a number of oligonucleotides by ligation.

The oligonucleotides were synthesized on an automatic DNA synthesizer using phosphoramidite chemistry on a controlled pore glass support (S. L. Beaucage and N. H. Caruthers (1981) Tetrahedron Letters 22, 1859–1869).

The following 10 oligonucleotides were synthesized:

I:   AAAGAGATTTCTGTTTGGAACCTCCATACACTGGTCC
     37-mer (SEQ ID NO:18)

II:  TTACATGGACCAGTGTATGGAGGTTCCAAACAGAAACT
     38-mer (SEQ ID NO:19)

III: ATGTAAAGCTAGAATCATCAGATACTTCTACAACG
     35-mer (SEQ ID NO:20)

IV:  TTCGGCGTTGTAGAAGTATCTGATGATTCTAGCT
     34-mer (SEQ ID NO:21)

V:   CCAAGGCTGGTTTGTGTCAAACTTTCGTTTACGGTGGCT
     39-mer (SEQ ID NO:22)

VI:  CTCTGCAGCCACCGTAAACGAAAGTTTGACACKAAACCAGC
     40-mer (SEQ ID NO:23)

VII: GCAGAGCTAAGTCCAACAACTTCAAGT
     27-mer (SEQ ID NO:24)

VIII: AGCAGACTTGAAGTTGTTGGACTTAG
      26-mer (SEQ ID NO:25)

IX:  CTGCTGAAGACTGCATGAGAACTTGTGGTGGTGCCTAAT
     39-mer (SEQ ID NO:26)

X:   CTAGATTAGGCACCACCACAAGTTCTCATGCAGTCTTC
     38-mer (SEQ ID NO:27)

5 duplexes A-E formed from the above 10 oligonucleotides as shown in FIG. 1.

20 pmole of each of the duplexes A-E was formed from the corresponding pairs of the above oligonucleotides by heating for 5 min. at 90° C. followed by cooling to room temperature over a period of 75 minutes. The five duplexes were mixed and treated with T4 ligase. The synthetic gene was isolated as a 176 bp band after electrophoresis of the ligation mixture on a 2% agarose gel. The obtained synthetic gene is shown in FIG. 1 and set forth in the Sequence Listing as SEQ ID NOS:28 AND 29. The synthetic gene was ligated to a 330 bp EcoRI-HgaI fragment from plasmid pKFN9 coding for MFα1 signal and leader sequence(1-85) and to the large EcoRI-XbaI fragment from pUC19. The construction of pKFN9 containing a HgaI site immediately after the MFα1 leader sequence is described in EP application No. 0214826.

The ligation mixture was used to transform a competent E. coli strain ($r^-$, $m^+$) selecting for ampicillin resistance. Sequencing of a $^{32}$P-XbaI-EcoRI fragment (Maxam, A. and Gilbert, W., Methods Enzymol. 65 (1980) 499–60) showed that plasmids from the resulting colonies contained the correct DNA-sequence for aprotinin(3-58).

Figure 3:
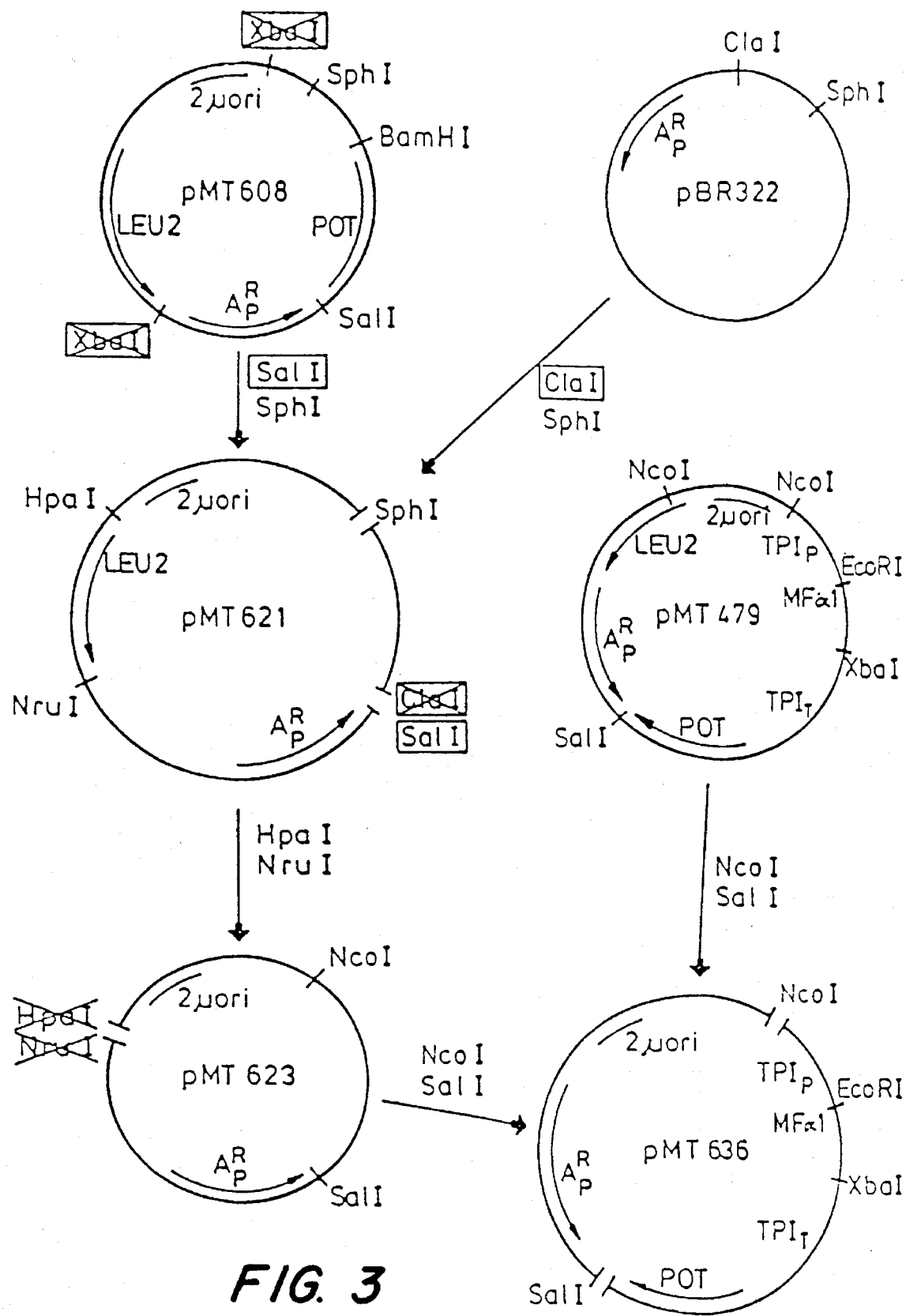
FIG. 3 illustrates the construction of plasmid pMT 636.

One plasmid pKNF305 was selected for further use. The construction of plasmid pKFN305 is illustrated in FIG. 2. pKFN305 was cut with EcoRI and XbaI and the 0.5 kb fragment was ligated to the 9.5 kb NcoI-XbaI fragment from pMT636 and the 1.4 kb NcoI-EcoRI fragment from pMT636, resulting in plasmid pKFN374 (see FIG. 2). Plasmid pMT636 was constructed from pMT608 after deletion of the LEU-2 gene and from pMT479 (see FIG. 3). pMT608 is described in EP application No. 1956911. pMT479 is described in EP application No. 163529. pMT479 contains the *Schizo. pombe* TPI gene (POT), the *S. cerevisiae* triose-phosphate isomerase promoter and terminator, $TPI_P$ and $TPI_T$ (Alber, T. and Kawasaki, G. J. Mol. Appl. Gen. 1 (1982) 419–434). Plasmid pKFN374 contains the following sequence Duplex A Duplex B Duplex C Duplex D Duplex E TPI$_p$-MFα1-signal-leader(1-85)-aprotinin(3-58)-TPI$_T$ where MFα1 is the *S. cerevisiae* mating factor alpha 1 coding sequence (Kurjan, J. and Herskowitz, I., Cell 30, (1982) 933-943), signal-leader(1-85) means that the sequence contains the first 85 amino acid residues of the MFα1 signal-leader sequence and aprotinin(3-58) is the synthetic sequence encoding an aprotinin derivative lacking the first two amino acid residues.

*S. cerevisiae* strain MT663 (E2-7B XE11-36 a/α, Δtpi Δtpi, pep 4-3/pep 4-3) was grown on YPGaL (1% Bacto yeast extract, 2% Bacto peptone, 2% galactose, 1% lactate) to an O.D. at 600 nm of 0.6.

100 ml of culture was harvested by centrifugation, washed with 10 ml of water, recentrifuged and resuspended in 10 ml of a solution containing 1.2M sorbitol, 25 mM Na$_2$EDTA pH=8.0, and 6.7 mg/ml dithiothreitol. The suspension was incubated at 30° C. for 15 minutes, centrifuged and the cells resuspended in 10 ml of a solution containing 1.2M sorbitol, 10 mM Na$_2$EDTA, 0.1M sodium citrate, pH=5.8, and 2 mg Novozym® 234. The suspension was incubated at 30° C. for 30 minutes, the cells collected by centrifugation, washed in 10 ml of 1.2M sorbitol and 10 ml of CAS (1.2M sorbitol, 10 mM CaCl$_2$, 10 mM Tris HCl (Tris=Tris (hydroxymethyl) aminomethane, pH=7.5) and resuspended in 2 ml of CAS. For transformation 0.1 ml of CAS-resuspended cells were mixed with approximately 1 μg of plasmid pKFN374 and left at room temperature for 15 minutes. 1 ml of (20% polyethylene glycol 4000, 10 mM CaCl$_2$, 10 mMTris HCl, pH=7.5) was added and the mixture left for further 30 minutes at room temperature. The mixture was centrifuged and the pellet resuspended in 0.1 ml of SOS (1.2M sorbitol, 33% v/v YPD, 6.7 mM CaCl$_2$, 14 μg/ml leucine) and incubated at 30° C. for 2 hours. The suspension was then centrifuged and the pellet resuspended in 0.5 ml of 1.2M sorbitol. Then, 6 ml of top. agar (the SC medium of Sherman et al., Methods in Yeast Genetics, Cold Spring Harbor Laboratory, 1981) containing 1.2M sorbitol plus 2.5% agar) at 52° C. was added and the suspension poured on top of plates containing the same agar-solidified, sorbitol containing medium. Transformant colonies were picked after 3 days at 30° C., reisolated and used to start liquid cultures. One such transformant KFN322 was chosen for further characterization.

Yeast strain KFN322 was grown on YUPD medium (1% yeast extract, 2% peptone (from Difco Laboratories), and 2% glucose). A 10 ml culture of the strain was shaken at 30° C. to an O.D. at 600 nm of 32. After centrifugation, the supernatant was analyzed by FPLC ion exchange chromatography. The yeast supernatant was filtered through a 0.22 μm Millex® GV filter unit and 1 ml was applied on a MonoS cation exchange column (0.5×5 cm) equilibrated with 20 mMBicine, pH 8.7. After wash with equilibration buffer the column was eluted with a linear NaCl gradient (0-1M) in equilibration buffer. Trypsin inhibitor activity was quantified in the eluted fractions by spectrophotometric assay and furthermore by integration of absorption at 280 nm from $E^{1\%}_{280}$ (aprotinin)=8.3

The yield was about 3 mg/liter of aprotinin(3-58).

For amino acid analysis and N-terminal sequencing, the yeast supernatant (7 ml) was adjusted to pH 8.7 with 0.1M NaOH and filtered (0.22 μm). The effluent from a Q-Sepharose anion exchange column (1×4 cm) equilibrated with 20 mM Bicine, pH 8.7 was applied to a MonoS cation exchange column (0.5×5 cm). The cation exchange chromatography was carried out as described above. Concentration of the gradient eluted aprotinin(3-58) was accomplished by rechromatography on MonoS and elution with a steep NaCl-gradient. The collected fractions were further concentrated by vacuum centrifugation to about 100 μl and applied to a RP-HPLC column (Vydac C4, 4.6×250 mm). Elution was carried out with CH$_3$CN gradient in 0.1% TFA. The collected fractions were concentrated to about 100 μl by vacuum centrifugation and samples were taken for N-terminal sequencing and amino acid analysis.

By N-terminal sequencing the following sequence was found

Asp—Phe—Cys—Leu—Glu—Pro—Pro—Tyr—Thr—Gly—Pro—Cys—Lys—Ala—
Arg—Ile—Ile—Arg (SEQ ID NO:31)

confirming that the N-terminal end is correct.

The amino acid analysis is shown in following Table 1. From this table it appears that the product has the expected amino acid composition, i.e., less Arg and Pro. The slightly lowered content of Ile can most probably be ascribed incomplete hydrolysis of Ile(18)-Ile(19) (this is well known in the art). Also, Pro and Arg is slightly higher than expected. This is, however, also seen with aprotinin itself (Table 1, second column).

When compared by the above mentioned method of Erlanger et al. the specific activity of aprotinin(3-58) was found to be identical within the experimental error with the specific activity of native aprotinin.

TABLE 1

| Amino Acid | Aprotinin (Theoretical) | Aprotinin (Found) | Aprotinin(3-58) (Found) | Aprotinin (3-58,42 Ser) (Found) |
|---|---|---|---|---|
| Asx | 5 | 5.00 | 4.96 | 5.02 |
| Thr | 3 | 2.86 | 2.83 | 2.85 |
| Ser | 1 | 0.94 | 0.97 | 1.78 |
| Glx | 3 | 3.04 | 3.01 | 3.02 |
| Pro | 4 | 4.18 | 3.15 | 3.19 |
| Gly | 6 | 5.95 | 6.00 | 5.99 |
| Ala | 6 | 5.85 | 5.93 | 6.01 |
| Cys | 6 | 5.20 | 5.03 | 5.41 |
| Val | 1 | 0.99 | 0.98 | 0.98 |
| Met | 1 | 0.83 | 0.85 | 0.96 |
| Ile | 2 | 1.39 | 1.41 | 1.50 |
| Leu | 2 | 1.97 | 1.98 | 2.03 |
| Tyr | 4 | 3.84 | 3.80 | 3.82 |
| Phe | 4 | 3.98 | 3.92 | 3.96 |
| Lys | 4 | 3.92 | 4.02 | 3.93 |
| Arg | 6 | 6.39 | 5.20 | 4.28 |
| Total | 58 | 56.33 | 54.04 | 54.73 |

7.2. EXAMPLE 2: PRODUCTION OF APROTININ (3-58, 42 Ser)

A synthetic gene for aprotinin(3-58, 42 Ser; SEQ ID NO:29) was constructed as described in Example 1 (Section 7.1., supra). With the purpose of substituting Arg(42) with Ser the following oligonucleotides VIIa and VIIIa were used instead of VII and VIII:

VIIa:   GCAGAGCTAAGTCCAACAACTTCAAGT 27-mer (SEQ ID NO:31)

VIIIa:  AGCAGACTTGAAGTTGTTGGACTTAG 26-mer (SEQ ID NO:32)

The obtained synthetic gene is shown in FIG. 5 (SEQ ID NOS:33 and 34). This gene fused to the MFα1 signal-eader(1-85) sequence was cloned in a pUC19 derived plasmid pKFN306 (see FIG. 6).

By following the procedure of Example 1 a plasmid pKFN375 was obtained containing the following construction TPI$_P$-MFα1-signal-leader(1-85)-aprotinin(3-58, 42 Ser) -TPI$_T$.

where aprotinin(3-58, 42 Ser) is the synthetic gene encoding an aprotinin derivative lacking the first two amino acid residues and containing a Ser instead of Arg in position 42.

Yeast strain MT663 was transformed with plasmid pKFN375 as described above, and culturing of the transformed strain KFN324 gave about 12 mg/liter of aprotinin(3-58, 42 Ser).

N-terminal sequencing carried out as described above confirmed the following N-terminal sequence Asp—Phe—Cys—Leu—Glu—Pro—Pro—Tyr—Thr—Gly—Pro—Cys—Lys—Ala—

Arg—Ile—Ile—Arg—Tyr—Phe  (SEQ ID NO:35)

i.e., the correct sequence.

The amino acid analysis is shown in Table 1 and confirms the expected amino acid composition, i.e., less Pro and Arg and more Ser (see also the above remarks in Example 1).

When compared by the above mentioned method of Erlanger et al. the specific activity of aprotinin(3-58, 42 Ser) was found to be identical within the experimental error with the specific activity of native aprotinin.

7.3. EXAMPLE 3: PRODUCTION OF APROTININ (1-58)

Figure 4:
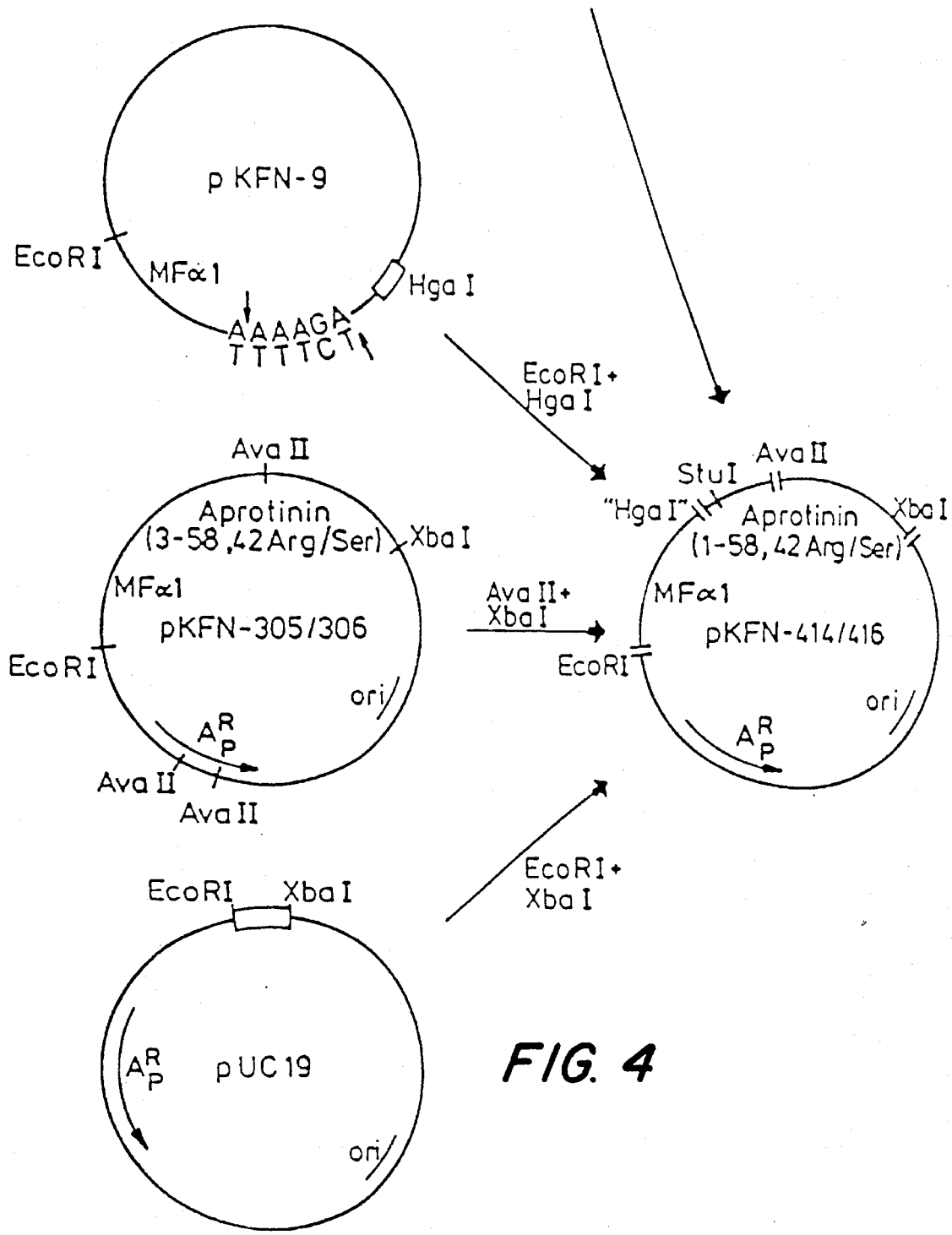
FIG. 4 illustrates the construction of plasmids pKFN414 and pKFN416.

The synthetic duplex (SEQ ID NOS:36 and 37) shown in FIG. 4 was ligated to the 330 bp EcoRI-HgaI fragment from plasmid pKFN9 coding for MFα1 signal and leader sequence and to the 144 bp AvaII-XbaI fragment from pKFN305 and to the large EcoRI-XbaI fragment from pUC19.

The ligation mixture was used to transform a competent E. coli strain (r⁻m⁺) selecting for ampicillin resistance. Sequencing of a $^{32}$P-labelled XbaI-EcoRI fragment showed that plasmids from the resulting colonies contained the correct DNA sequence for aprotinin(1-58).

One plasmid pKFN414 was selected for further use. The construction of plasmid pKFN414 is illustrated in FIG. 4.

By following the procedure of Example 1 (Section 7.1., supra) a yeast plasmid pKFN418 was obtained containing the following construction:

TPI$_P$-MFα1-signal-leader(1-85)-aprotinin(1-58)-TPI$_T$.

Yeast strain MT633 was transformed with plasmid pKFN418 as described above. Culturing of the transformed strain KFN385 gave about 1–13 mg/l of aprotinin(1-58).

When compared with the above mentioned method of Erlanger et al., the specific activity of aprotinin(1-58), produced according to this example was found to be identical within the experimental error with the specific activity of native aprotinin. The sequence of the synthetic gene encoding aprotinin(1-58) is shown in FIG. 16 and set forth in the Sequence Listing as SEQ ID NOS:38 and 39.

7.4. EXAMPLE 4: PRODUCTION OF APROTININ(1-58, 42 Ser)

A plasmid pKFN416 containing a gene for aprotinin(1-58, 42 Ser) was constructed from pKFN306 as described in Example 3 (Section 7.3., supra). The synthetic gene encoding aprotinin(1-58, 42 Ser) is shown in FIG. 17 and set forth in the Sequence Listing as SEQ ID NOS:40 and 41. By following the procedure of Example 1 (Section 7.1., supra) a yeast plasmid pKFN420 was obtained containing the following construction:

TPI$_P$-MFα1-signal-leader(1-85)-aprotinin(1-58,42 Ser) -TPI$_T$.

Yeast strain MT663 was transformed with plasmid pKFN420 as described above. Culturing of the transformed strain KFN387 gave about 1–13 mg/l of aprotinin(1-58, 42 Ser).

When compared with the above mentioned method of Erlanger et al., the specific activity of aprotinin(1-58,42 Ser) was found to be identical within the experimental error with the specific activity of native aprotinin.

7.5. EXAMPLE 5: APROTININ (3-58; 17 Ala+42 Ser) (KFN 396)

A sequence encoding aprotinin (3-58; 42 Ser) was constructed from a number of oligonucleotides by ligation using procedures described in Example 2 (Section 7.2., supra).

Figure 6:
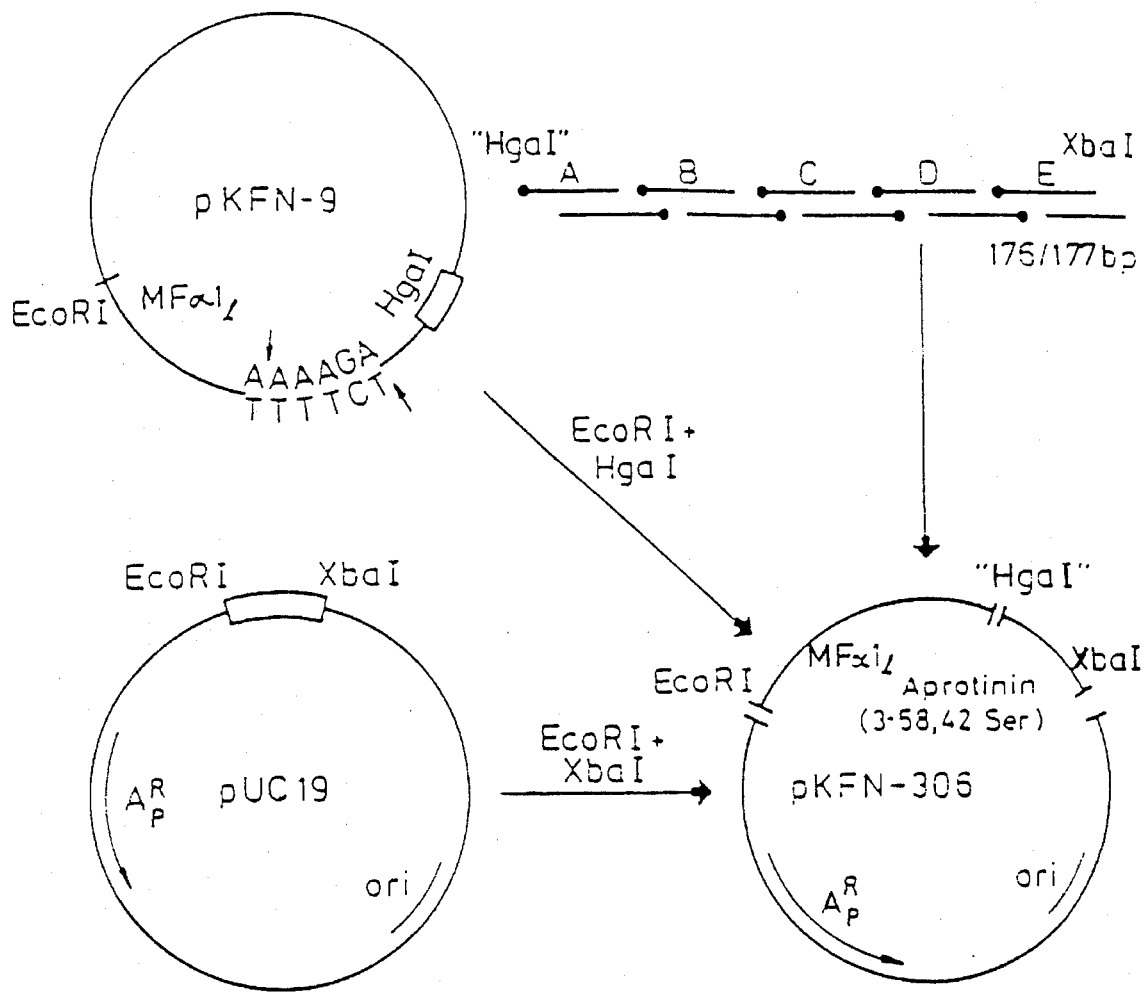
FIG. 6 illustrates the construction of the plasmid pKFN 306.
Figure 7:
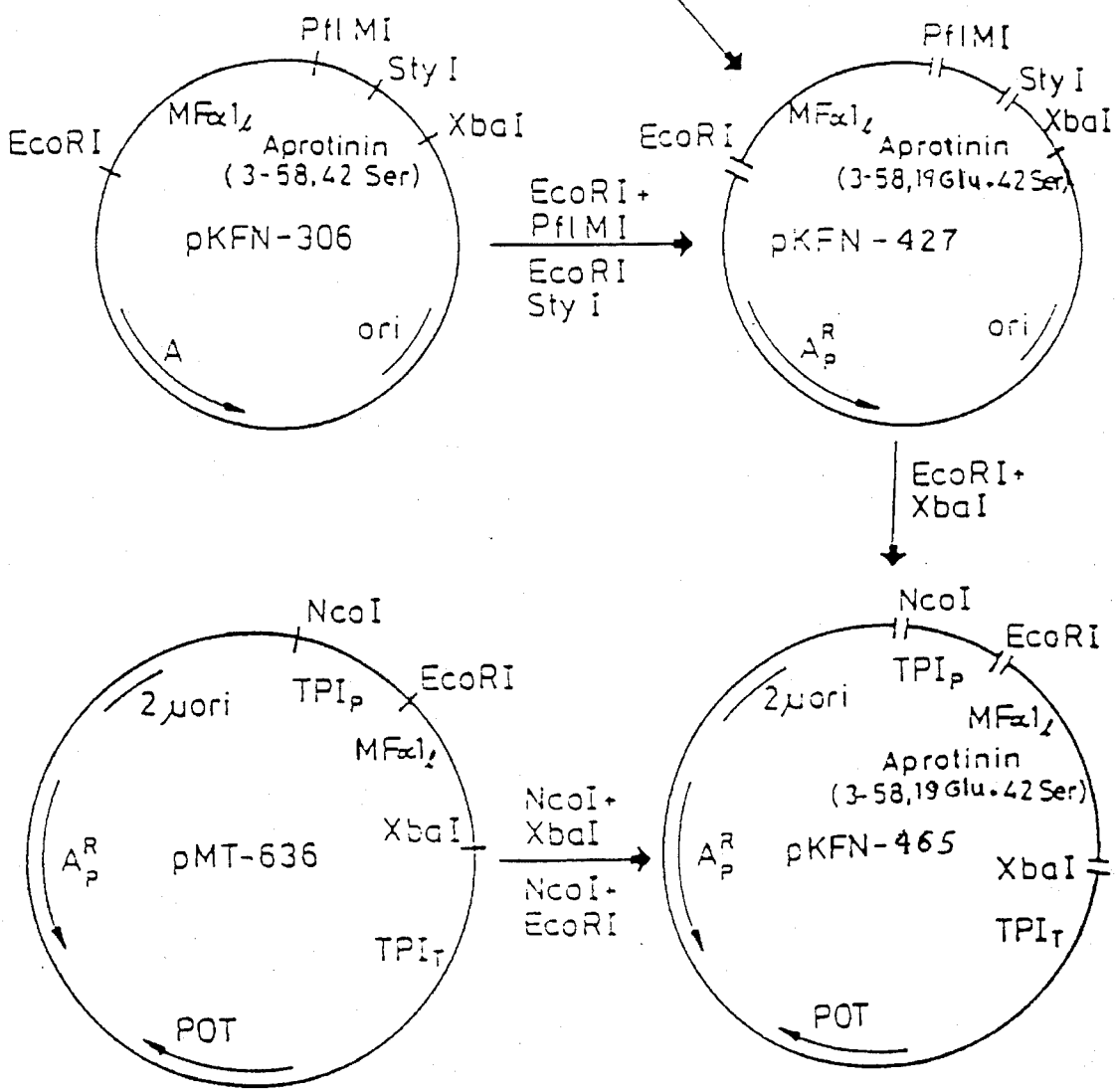
FIG. 7 illustrates the construction of the plasmid pKFN 504.
Figure 8:
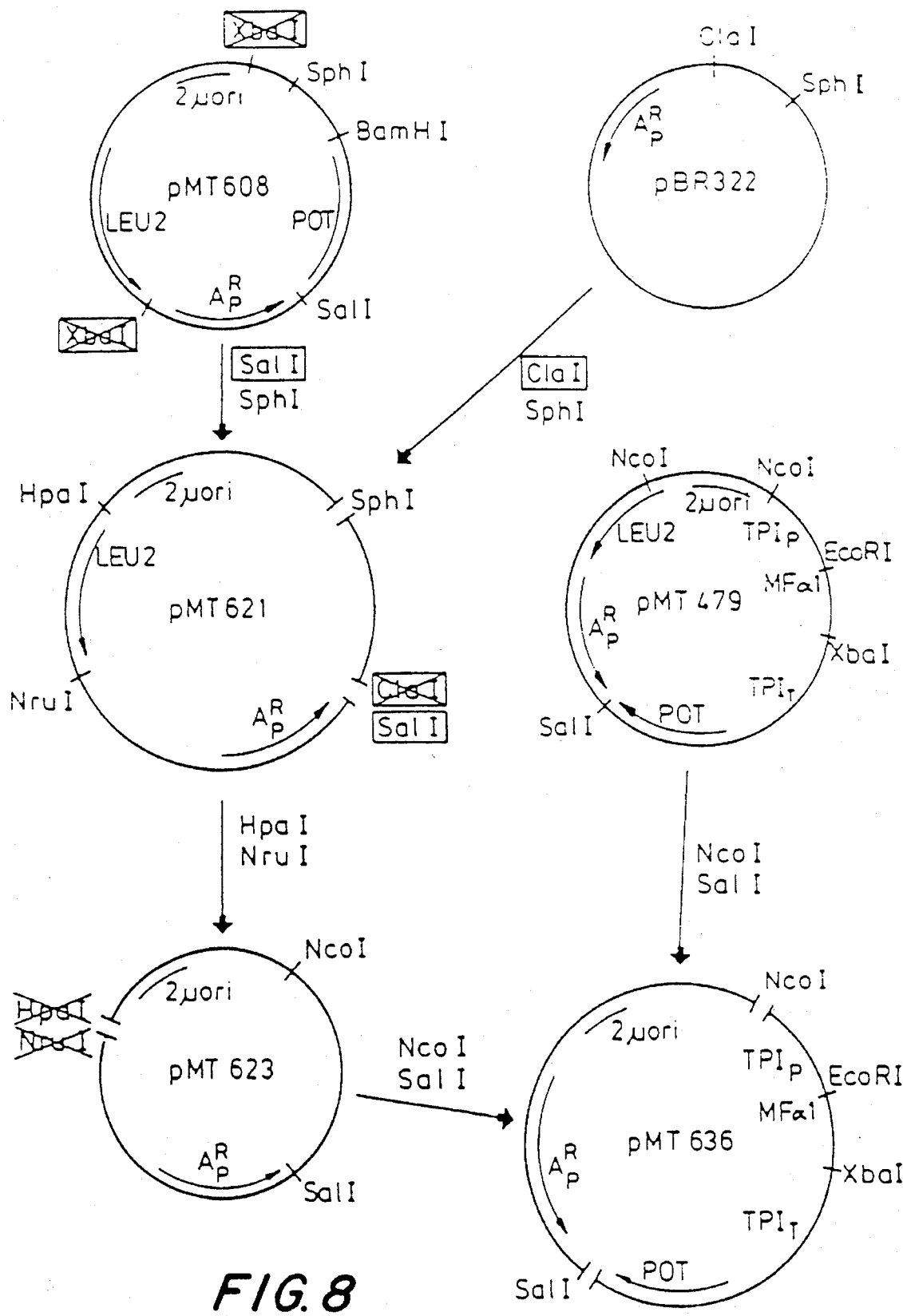
FIG. 8 illustrates the construction of the plasmid pMT 636.

One plasmid, pKFN306, was selected for further use. The construction of plasmid pKFN306 is illustrated in FIG. 6.

To introduce Ala in position 17 the following oligonucleotides were synthesized as described below:

Ia:   CTGGTCCATGTAAAGCTGCTATCATCAGATACTTCTACAACGC 43-mer (SEQ ID NO:34)

IIa:  CTTGGCGTTGTAGAAGTATCTGATGATAGCAGCTTTACATGGACCAGTGT 50-mer (SEQ ID NO:35)

The oligonucleotides were 5'-phosphorylated by treatment with ATP and T4 kinase.

A duplex formed by annealing 5'-phosphorylated oligonucleotides Ia and IIa was ligated to the 352 bp EcoRI-PflMI fragment and the 3 kbp EcoRI-StyI fragment, both from pKFN306. pKFN306 encodes the S. cerevisiae mating factor αl signal leader (1-85) fused to the synthetic aprotinin (3-58; 42 Ser) gene.

The ligation mixture was used to transform a competent E. coli strain (r⁻, m⁺) selecting for ampicillin resistance. Sequencing of a $^{32}$P-XbaI-EcoRI fragment (Maxam, A. and Gilbert, W. (1980) Methods Enzymol. 65:499–560) showed that plasmids from the resulting colonies contained the correct DNA sequence for aprotinin (3-58; 17 Ala+42 Ser).

One plasmid, pKFN501 was selected for further use. The construction of plasmid pKFN501 is illustrated in FIG. 4.

pKFN501 was cut with EcoRI and XbaI and the 0.5 kb fragment was ligated to the 9.5 kb NcoI-XbaI fragment from pMT636 and the 1.4 kb NcoI-EcoRI fragment from pMT636, resulting in plasmid pKFN504 (see FIG. 4). Plasmid pMT 636 was constructed from pMT608 after deletion of the LEU-2 gene and from pMT479 (see FIG. 3). pMT608 is described in European Application NO. 195691. pMT479 is described in European Patent Application NO. 163529. pMT479 contains the Schizo, pombe TPI gene (POT), the S. cerevisiae triosephosphate isomerase promoter and terminator, TPI$_P$ and TPI$_T$ (Alber, T. and Kawasaki, G. (1982) J. Mol. Appl. Gen. 1, 419–434). Plasmid pKFN504 contains the following sequence: TPI$_P$-MFαl-signal-leader (1-85)-aprotinin(3-58; 17 Ala+42 Ser)-TPI$_T$ where MFαl is the S. cerevisiae mating factor alpha 1 coding sequence (Kurjan, J. and Herskowitz, I. (1982) Cell 30, 933–943), signal leader (1-85) means that the sequence contains the first 85 amino acid residues of the MFαl signal leader sequence and aprotinin (3-58; 17 Ala+42 Ser) is the synthetic sequence encoding an aprotinin derivative lacking the first two amino acid residues at the N-terminus and having amino acid residues 17 and 42 replaced by an Ala and a Ser residue, respectively.

S. cerevisiae strain MT663 (E2-7B XE11-36 a/α, ΔtpiΔtpi, pep 4-3/pep 4-3 ) was grown on YPGaL (1% Bacto yeast extract, 2% Bacto peptone, 2% galactose, 1% lactate) to an optical density at 600 nm of 0.6.

100 ml of culture was harvested by centrifugation, washed with 10 ml of water, recentrifuged and resuspended in 10 ml of (1.2M sorbitol, 25 mM Na$_2$EDTA pH=8.0, 6.7 mg/ml dithiothreitol). The suspension was incubated at 30° C. for 15 minutes, centrifuged and the cells resuspended in 10 ml of (1.2M sorbitol, 10 mM Na$_2$EDTA, 0.1M sodium citrate pH=5.8, 2 mg Novozym® 234). The suspension was incubated at 30° C. for 30 minutes, the cells collected by centrifugation, washed in 10 ml of 1.2M sorbitol and 10 ml of CAS (1.2M sorbitol, 10 mM CaCl$_2$, 10 mM Tris HCl (Tris=Tris (hydroxymethyl) aminomethane) pH=7.5) and resuspended in 2 ml of CAS. For transformation 0.1 ml of CAS resuspended cells were mixed with approximately 1 μg of plasmid pKFN504 and left at room temperature for 15 minutes. 1 ml of (20% polyethylene glycol 4,000, 10 mM CaCl$_2$, 10 mM Tris HCl, pH=7.5) was added and the mixture left for further 30 minutes at room temperature. The mixture was centrifuged and the pellet resuspended in 0.1 ml of SOS (1.2M sorbitol, 33% v/v YPD, 6.7 mM CaCl$_2$, 14 μg/ml leucine)) and incubated at 30° C. for 2 hours. The suspension was then centrifuged and the pellet resuspended in 0.5 ml of 1.2M sorbitol. 6 ml of top agar (the SC medium of Sherman et al., Methods in Yeast Genetics, Cold Spring Harbor Laboratory, 1981) containing 1.2M sorbitol plus 2.5% agar) at 52° C. was added and the suspension poured on top of plates containing the same agar solidified, sorbitol containing medium. Transformant colonies were picked after 3 days at 30° C., reisolated and used to start liquid cultures. One such transformant KFN396 was chosen for further characterization.

Yeast strain KFN396 was grown on YPD medium (1% yeast extract, 2% peptone (from Difco Laboratories) and 2% glucose). A 1 liter culture of the strain was shaken at 30° C. to an optical density of 600 nm of 13. After centrifugation the supernatant was purified by FPLC ion exchange chromatography. The yeast supernatant was filtered through a 0.22 μm Millex® GV filter unit and 1 ml was applied on a MonoS cation exchange column (0.5×5 cm) equilibrated with 20 mM Bicine, pH 8.7. After wash with equilibration buffer the column was eluted with a linear NaCl gradient (0-1M) in equilibration buffer. Trypsin inhibitor activity was quantified in the eluted fractions by spectrophotometric assay and furthermore by integration of absorption at 280 nm from:

$$E^{1\%}_{280} \text{ (aprotinin)}=8.3$$

The yield was about 4.3 mg/liter of aprotinin (3-58; 17 Ala+42 Ser).

For amino acid analysis the yeast supernatant (7 ml) was adjusted to pH 8.7 with 0.1M NaOH and filtered (0.22 μm). The effluent from a Q-Sepharose anion exchange column (1×4 cm) equilibrated with 20 mM Bicine, pH 8.7 was applied to a MonoS cation exchange column (0.5×5 cm). The cation exchange chromatography was carried out as described above. Concentration of the gradient eluted aprotinin (3-58) was made by rechromatography on MonoS and elution with steep NaCl gradient. The collected fractions were further concentrated by vacuum centrifugation to about 100 μl and applied to a RP-HPLC column (Vydac 4.6×250 mm). Elution was carried out with CH$_3$CN gradient in 0.1% TFA. The collected fractions were concentrated to about 100 μl by vacuum centrifugation and samples were taken for amino acid analysis.

The amino acid analysis appears from the following Table 2. From this table it appears that the product has the expected amino acid composition:

| Amino Acid | Theoretical | Aprotinin (3–58; 17 Ala + 42 Ser) (Found) |
|---|---|---|
| Asx | 5 | 4.90 |
| Thr | 3 | 2.95 |

| Amino Acid | Theoretical | Aprotinin (3–58; 17 Ala + 42 Ser) (Found) |
|---|---|---|
| Ser | 2 | 2.10 |
| Glx | 3 | 3.01 |
| Pro | 3 | 3.14 |
| Gly | 6 | 5.93 |
| Ala | 7 | 6.69 |
| Cys | 6 | 5.91 |
| Val | 1 | 1.02 |
| Met | 1 | 0.99 |
| Ile | 2 | 2.00 |
| Leu | 2 | 1.98 |
| Tyr | 4 | 3.73 |
| Phe | 4 | 3.75 |
| Lys | 4 | 4.29 |
| Arg | 3 | 3.21 |
| Total | 56 | 55.60 |

7.6. EXAMPLE 6: APROTININ (3-58; 17 Ala+19 Glu+42 Ser) (KFN 399)

A synthetic gene encoding aprotinin (3-58; 17 Ala+19 Glu+42 Ser) was constructed as described in Example 5 (Section 7.5., supra). The following oligonucleotides Ib and IIb were used instead of Ia and IIa:

Ib: CTGGTCCATGTAAAGCTGCTATCGAAAGATACTTCTACAACGC
43-mer (SEQ ID NO:42)

IIb: CTTGGCGTTGTAGAAGTATCTTTCGATAGCAGCTTTACATGGACCAGTGT
50-mer 9 (SEQ ID NO:43)

The pUC19 derived plasmid pKFN503 was constructed in a similar way as pKFN501.

By following the procedure of Example 5 a plasmid pKFN507 was obtained containing the following construction: TPI$_P$-MFα1-Signal-leader(1-85)-aprotinin(3-17 Ala+19 Glu+42 Ser)-TPIT, where aprotinin (3-58; 17 Ala+ 19 Glu+42 Ser) is the synthetic gene encoding an aprotinin derivative lacking the first two amino acid residues at the N-terminal and having the residues 17, 19 and 42 of native aprotinin replaced by an alanine, a glutamic acid and a serine residue, respectively.

Plasmid pKFN507 was transformed in yeast strain MT663 as described above and culturing of the transformed strain KFN399 gave about 10 mg/liter of aprotinin (3-58; 17 Ala+19 Glu+42 Ser).

The amino acid analysis appears from the following Table 3 and confirms the expected amino acid composition:

| Amino Acid | Theoretical | Aprotinin (3–58; 17 Ala + 19 Glu + 42 Ser) (Found) |
|---|---|---|
| Asx | 5 | 4.95 |
| Thr | 3 | 2.83 |
| Ser | 2 | 1.90 |
| Glx | 4 | 4.08 |
| Pro | 3 | 2.98 |
| Gly | 6 | 5.98 |
| Ala | 7 | 6.92 |
| Cys | 6 | 5.06 |
| Val | 1 | 0.99 |
| Met | 1 | 0.86 |
| Ile | 1 | 0.99 |
| Leu | 2 | 1.99 |
| Tyr | 4 | 3.77 |
| Phe | 4 | 3.89 |
| Lys | 4 | 4.07 |
| Arg | 3 | 3.06 |
| Total | 56 | 54.36 |

7.7. EXAMPLE 7: APROTININ (3-58; 15 Arg+17 Ala+42 Set) (KFN 773)

A synthetic gene encoding aprotinin (3-58; 15 Arg+17 Ala+42 Ser) was constructed as described in Example 5 (See Section 7.5., supra). The following oligonucleotides Ic and IIc were used instead of Ia and IIa:

Ic: CTGGTCCATGTAGAGCTGCTATCATCAGATACTTCTACAACGC
43-mer (SEQ ID NO:44)

IIc: CTTGGCGTTGTAGAAGTATCTGATGATAGCAGCTCTACATGGACCAGTGT
50-mer (SEQ ID NO:45)

The pUC19 derived plasmid pKFN777 was constructed in a similar way as pKFN501.

By following the procedure of Example 5 (Section 7.5, supra) a plasmid pKFN807 was obtained containing the following construction: TPI$_P$-MFα1-signal-leader (1-85)-aprotinin (3-58; 15Arg+17Ala+42Ser) -TPI$_T$, where aprotinin (3-58; 15 Arg+17 Ala+42 Ser) is the synthetic gene encoding an aprotinin derivative lacking the first two amino acid residues at the N-terminal and having the residues 15, 17 and 42 of native aprotinin replaced by an arginine, an alanine and a serine residue, respectively.

Plasmid pKFN807 was transformed in yeast strain MT663 as described above and culturing of the transformed strain KFN773 gave about 8.5 mg/liter of aprotinin (3-58; 15 Arg+17 Ala+42 Ser).

The amino acid analysis is shown in Table 4 and confirms the expected amino acid composition:

| Amino Acid | Theoretical | Aprotinin (3-58; 17 Arg + 17 Ala + 42 Ser) (Found) |
|---|---|---|
| Asx | 5 | 4.95 |
| Thr | 3 | 2.85 |
| Ser | 2 | 1.81 |
| Glx | 3 | 3.01 |
| Pro | 3 | 3.05 |
| Gly | 6 | 5.92 |
| Ala | 7 | 6.91 |
| Cys | 6 | 5.31 |
| Val | 1 | 1.02 |
| Met | 1 | 0.73 |
| Ile | 2 | 1.41 |
| Leu | 2 | 1.99 |
| Tyr | 4 | 3.80 |
| Phe | 4 | 3.94 |
| Lys | 3 | 2.97 |
| Arg | 4 | 4.24 |
| Total | 56 | 53.91 |

The slightly lowered content of Ile compared with the theoretical value can most probably be ascribed to incomplete hydrolysis of Ile (18)-Ile (19). This is well known in the art.

7.8. EXAMPLE 8: INHIBITION OF SERINE PROTEASES FROM PLASMA BY APROTININ (3-58; 17 Ala+42 Set) (KFN 396) AND APROTININ (3-58; 17 Ala+19 Glu+42 Set) (KFN 399), APROTININ (3-58; 15 Arg+42 Set) (KFN 772) AND APROTININ (3-58; 15 Arg+17 Ala +42 Ser) (KFN 773).

Aprotinin (3-58; 17 Ala+42 Ser; SEQ ID NO:5) (KFN 396), aprotinin (3-58; 17 Ala+19 Glu+42 Ser; SEQ ID NO:6) (KFN 399) and aprotinin (3-58; 15 Arg+17 A! a+42 Ser; SEQ ID NO:7) (KFN 773) were purified as described above. As native, bovine pancreatic aprotinin (1-58; SEQ ID NO:1) batch B 5029-65 (67,000 KIU/mg) from NOVO (Bagsvaerd, Denmark) was used. The concentration was calculated using $E_{280}nm=8.3$ and $M_r=6,500$. Human plasma kallikrein was obtained from Sigma (St. Louis, Mo.), bovine factor Xa was purified according to (H. Nobukazu et al. J. Biochem. 97 (1985) 1347–1355), human factor IIa (thrombin) was a gift from Dr. W. Lawson (New York State Department of Health, Albany, New York), recombinant human factor VIIa was from NOVO (Bagsvaerd, Denmark) and recombinant human protein Ca was from ZymoGenetics, Inc. (Seattle, Wash.). Substrate S 2302 (H-D-Pro-Phe-Arg-pnitroanilide) substrate S2238 (H-D-Phe-Pip-Arg-pnitroanilide) and substrate S2366 (Glu-Pro-Arg-pnitroanilide) were from Kabi (Stockholm, Sweden). Substrate FXa-1 (methoxycarbonyl DCH-Gly-Arg-p-nitroanilide) was from NycoMed (Oslo, Norway). The experiments were performed in 100 mM NaCl, 50 mM Tris-HCl 0.01% Tween80, pH 7.4 at 25° C.

Figure 9A:
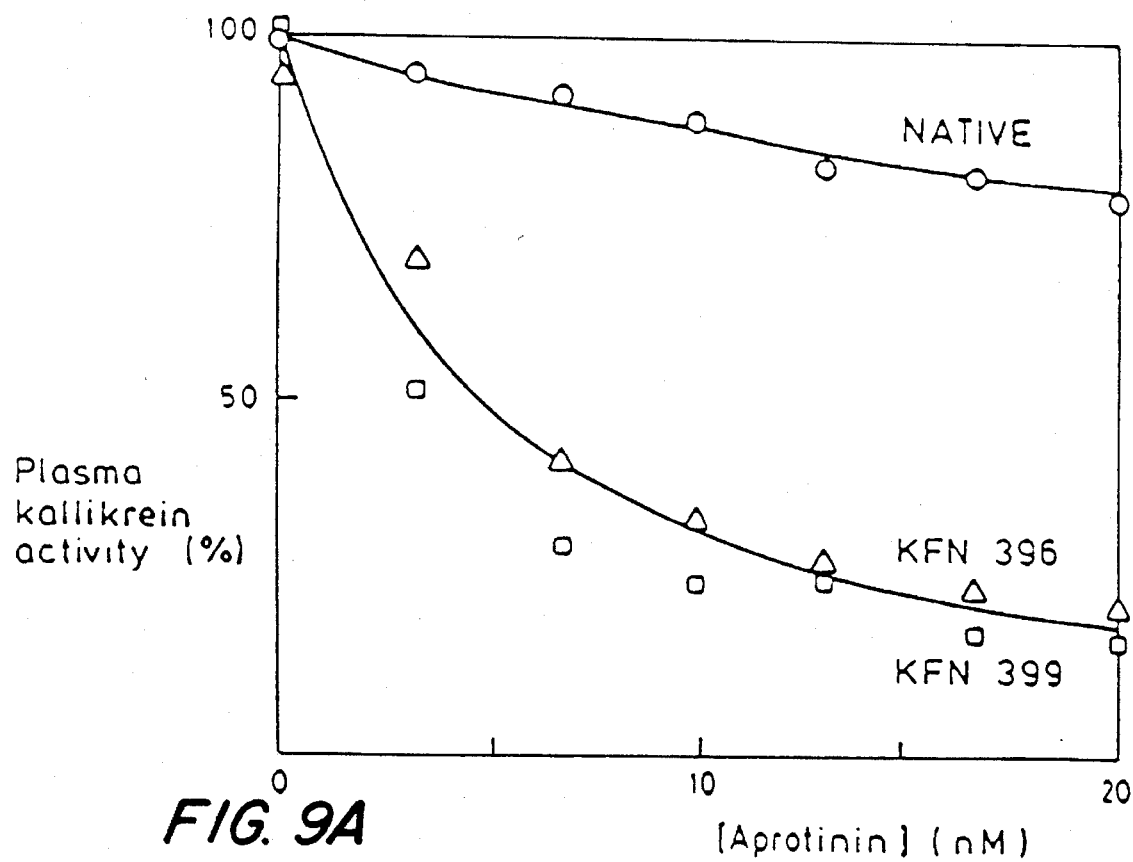
FIG. 9A illustrates the inhibition of plasma kallikrein by native aprotinin and by the aprotinin analogs KFN 396 and KFN 399.
Figure 9B:
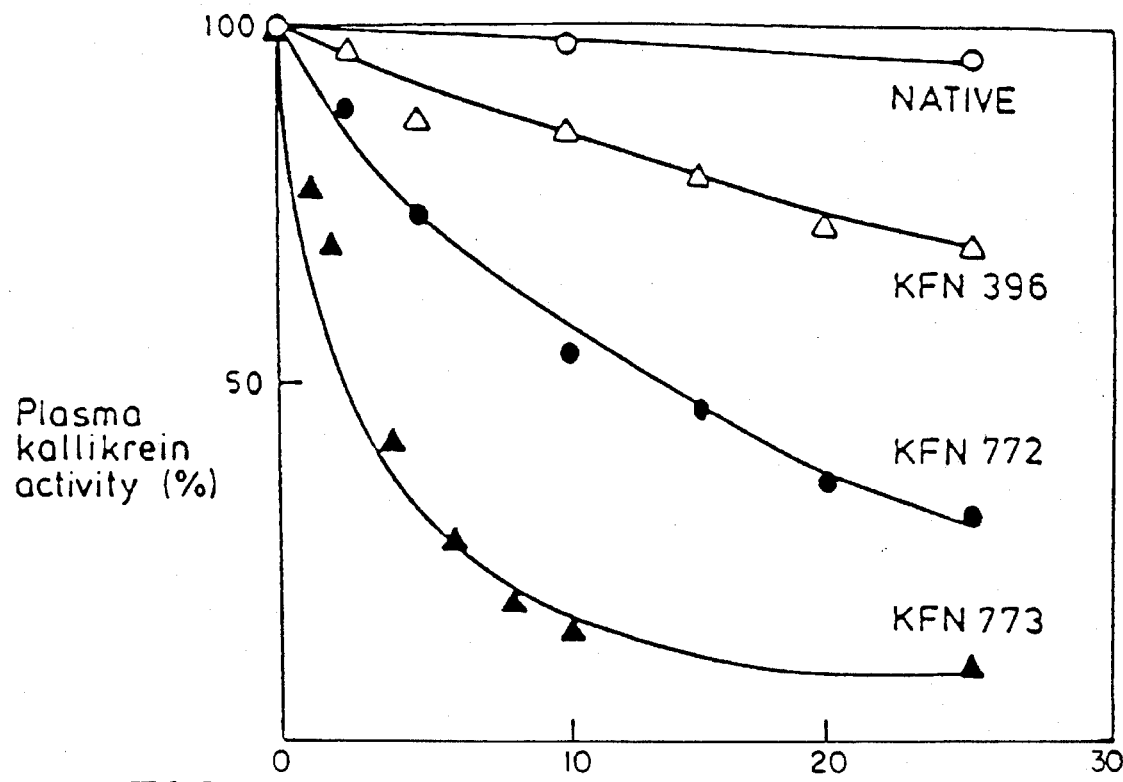
FIG. 9B illustrates the inhibition of plasma kallikrein by native aprotinin and by the aprotinin analogs KFN 396, KFN772 and KFN773.

Human plasma kallikrein (3 nM) was incubated with aprotinin (0-20 nM) for 30 minutes in a micro-titer well. Substrate S 2302 (0.6 nM) was added to a final volume of 300 µl and the rate of nitroaniline generation was measured at 405 nm by means of a Micro ELISA® Autoreader MR 580 from Dynatech Laboratories. The rate is proportional to the concentration of free enzyme. The inhibition of plasma kallikrein by native aprotinin and the 4 analogues KFN 396, KFN 399, KFN 772 and KFN 773 is shown in FIG. 9A and 9B. With native aprotinin a moderate inhibition was observed. The inhibition was strongly increased by analogs KFN 396 and KFN 399 containing Ala in position 17 (FIG. 9A).

A further increase of the inhibition was obtained with Arg in position 15 (KFN 772); and the strongest inhibition was observed with the analog (KFN 773) with substitution of both position 17 (Ala) and position 15 (Arg) (FIG. 9B).

The analogs were also tested for inhibition of the amidolytic activity of the serine proteases: bovine factor Xa, human factor IIa, human recombinant factor VIIa and human recombinant protein Ca. The experiments were performed essentially as described for plasma kallikrein only appropriate substrates were used. Finally the analogs were analyzed for an effect on the coagulation factors of human plasma by means of two clotting tests. These tests, the prothrombin time (PTT) and the activated thromboplastin time (ATPT) were performed with General Diagnostics® reagents from Organon (Durham, N.C.) according to the directions given by the manufacturer. The results of the inhibition experiments are summarized in Table 5 which describes the inhibition profile of the 4 aprotinin analogs. KFN 773 is characterized by an extraordinarily strong inhibition of human plasma kallikrein which is ten-fold stronger than that of the Arg 15 analogue (KFN 772). A reverse effect is observed with activated protein C. In this case, the relatively strong inhibition obtained by substitution of Lys 15 to Arg is weakened by further substitution of Arg 17 to Ala.

TABLE 5

| Product | $K_i^*$) (nM); Amidolytic Activity of Serine Proteases § Plasma Kallikrein | FIIa | FVIIa | FXa | Prot. Ca | Clot Assays PTT | APTT |
|---|---|---|---|---|---|---|---|
| Native Aprotinin | 180 | — | — | — | 400 | — | — |
| KFN 396 | 12 | — | — | — | — | — | — |
| KFN 399 | 12 | | | | | | |
| KFN 772 | 1 | — | — | 1,800 | 10 | — | + |
| KFN 773 | 0.1 | — | — | 150 | 100 | — | + |

— No inhibition at 1.0 µM aprotinin analog

TABLE 5-continued

| | $K_i^*$) (nM); Amidolytic Activity of Serine Proteases § | | | | | Clot Assays | |
|---|---|---|---|---|---|---|---|
| Product | Plasma Kallikrein | FIIa | FVIIa | FXa | Prot. Ca | PTT | APTT |

+ Prolonged clotting time at 1.0 μM aprotinin analog
*) Inhibition constants estimated according to the graphical Dixon method (M. Dixon, Biochem. J. 129 (1972) 197–202)
§ Substrates: Plasma kallikrein: S2302; FIIa: S2238; FVIIa: Substrate FXa-1; FXa: Substrate FXa-1; Prot. Ca: S2366.

7.9. EXAMPLE 9: PRODUCTION OF [Glu1, Glu26, Glu41, Glu46]-APROTININ FROM YEAST STRAIN KFN-1512

A synthetic gene coding for [Glu1, Glu26, Glu41, Glu46]-aprotinin was constructed from 10 oligonucleotides by ligation.

The oligonucleotides were synthesized on an automatic DNA synthesizer using phosphoramidite chemistry on a controlled pore glass support (Beaucage, S. L., and Caruthers, M. H., *Tetrahedron Letters* 22, (1981) 1859–1869).

The following 10 oligonucleotides were synthesized:

NOR-1948: CATGGCTGAGAGATTGGAGAAGAGAGAGCCTGATTTCTGTTTGGAAC
CTCCATACACTGGTCC (SEQ ID NO:46)

NOR-1947: TTACATGGACCAGTGTATGGAGGTTCCAAACAGAAATCAGGCTCTCT
CTTCTCCAATCTCTCAGC (SEQ ID NO:47)

NOR-354: ATGTAAAGCTAGAATCATCAGATACTTCTACAACG (SEQ ID NO:20)

NOR-1939: TTCGGCGTTGTAGAAGTATCTGATGATTCTAGCT (SEQ ID NO:21)

NOR-1938: CCGAAGCTGGTTTGTGTCAAACTTTCGTTTACGGTGGCT (SEQ ID NO:48)

NOR-357: CTCTGCAGCCACCGTAAACGAAAGTTTGACACAAACCAGC (SEQ ID NO:49)

NOR-1940: GCAGAGCTGAAAGAAACAACTTCGAAT (SEQ ID NO:50)

NOR-1949: AGCAGATTCGAAGTTGTTTCTTTCAG (SEQ ID NO:51)

NOR-360: CTGCTGAAGACTGCATGAGAACTTGTGGTGGTGCCTAAT (SEQ ID NO:26)

NOR-361: CTAGATTAGGCACCACCACAAGTTCTCATGCAGTCTTC (SEQ ID NO:27)

5 duplexes A-E were formed from the above 10 oligonucleotides as shown in FIG. 10. 20 pmole of each of the duplexes A-E were formed from the corresponding pairs of 5'-phosphorylated oligonucleotides by heating for 5 min. at 90° C. followed by cooling to room temperature over a period of 75 minutes. The five duplexes were mixed and treated with T₄ DNA ligase. The synthetic gene was isolated as a 203 bp band after electrophoresis of the ligation mixture on a 2% agarose gel. The obtained synthetic gene is shown in FIG. 10 and is set forth as SEQ ID NO:28. The synthetic gene was ligated to a 209 bp EcoRI-NcoI fragment from pLaC212spx3 and to the 2.8 Kb EcoRI-XbaI fragment of plasmid pTZ19R (Mead, D. A., Szczesna-Skorupa, E. and Kemper, B., *Prot. Engin.* 1 (1986) 67–74). Plasmid pLaC212spx3 is described in Example 3 of International Patent Application No. PCT/DK88/00147. The 209 bp EcoRI-NcoI fragment from pLaC212spx3 encodes a synthetic yeast leader peptide.

The ligation mixture was used to transform a competent *E. coli* strain r⁻, m⁺) selecting for ampicillin resistance. DNA sequencing (Sanger, F., Micklen, S., and Coulson, A. R., *Proc. Natl. Acad. Sci.* USA 74 (1977) 5463–5467) showed that plasmids from the resulting colonies contained the correct DNA Sequence for [Glu1, Glu26, Glu41, Glu46]-aprotinin.

Figure 11:
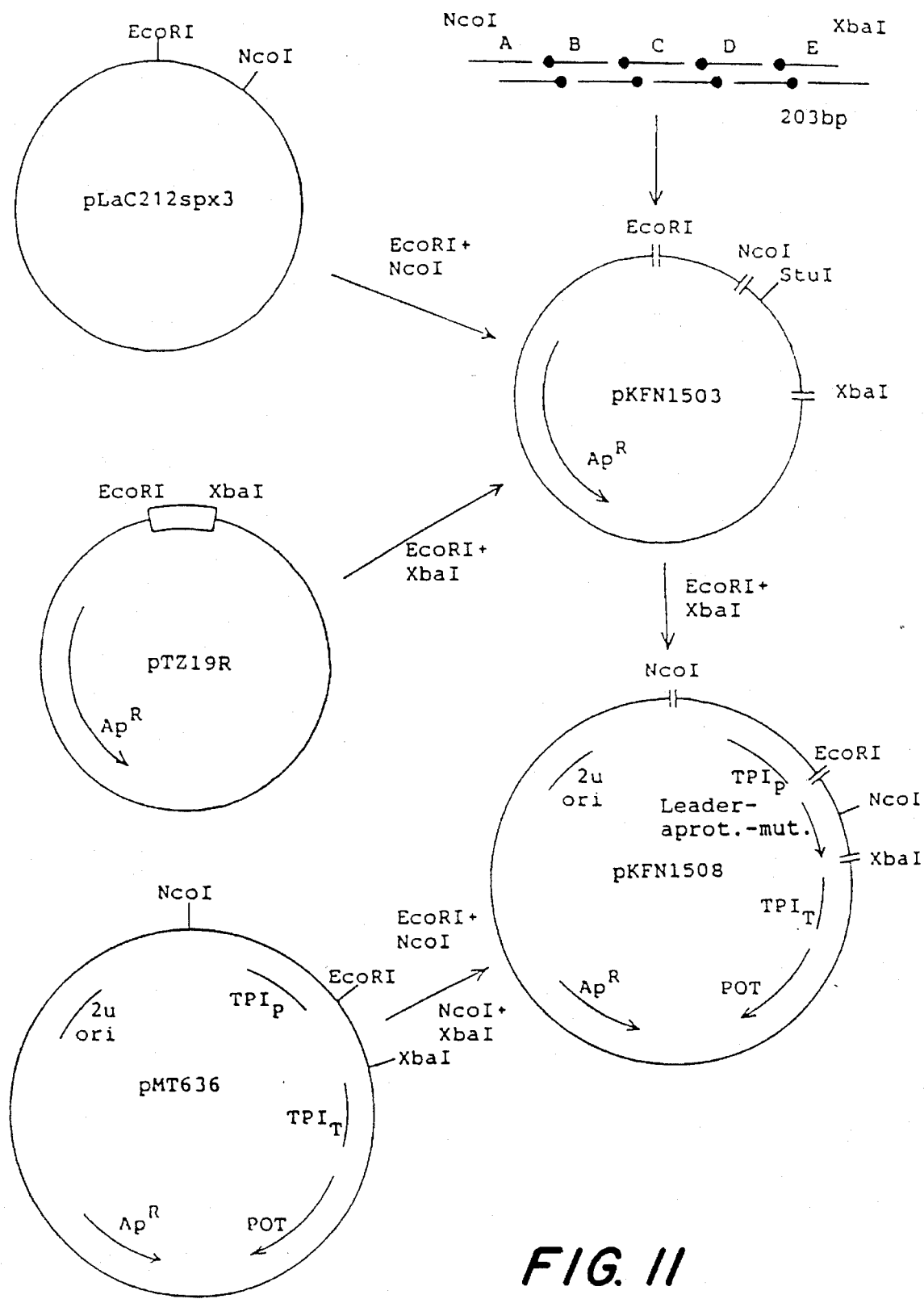
FIG. 11 shows the construction of plasmid pKFN-1503.

One plasmid pKFN-1503 was selected for further use. The construction of plasmid pKFN-1503 is illustrated in FIG. 11. pKFN-1503 was cut with EcoRI and XbaI and the 412 bp fragment was ligated to the 9.5 kb NcoI-XbaI fragment from pMT636 and the 1.4 kb NcoI-EcoRI f raiment from pMT636, resulting in plasmid pKFN-1508 (see FIG. 11). Plasmid pMT636 is described in International Patent Application No. PCT/DK88/00138.

pMT636 is an *E. coli-S. cerevisiae* shuttle vector containing the *Schizosaccharomyces pombe* TPI gene (POT) (Russell, P. R., *Gene* 40 (1985) 125–130), the *S. cerevisiae* triosephosphate isomerase promoter and terminator, TPI$_P$ and TPI$_T$ (Alber, T., and Kawasaki, G. J. *Mol. Appl. Gen.* 1 (1982), 419–434). Plasmid pKFN-1508 contains the following sequence: TPI$_P$-LaC212spx3 signal-leader (1-47)-Glu (ArgLeuGluLysArg [Glu1, Glu26, Glu41, Glu46]-aprotinin-TPI$_T$ where LaC212spx3 signal-leader is the synthetic yeast leader described in International Patent Application No. PCT/DK88/00147. The DNA sequence of the 412 bp EcoRI- XbaI fragment from pKFN-1503 and pKFN-1508 is SEQ ID NOS:52 and 53.

*S. cerevisiae* strain MT663 (E2-7B XEll-36 a/α, tpi/tpi, pep 4-3/pep 4-3) was grown on YPGaL (1% Bacto yeast extract, 2% Bacto peptone, 2% galactose, 1% lactate) to an O.D. at 600 nm of 0.6.

100 ml of culture was harvested by centrifugation, washed with 10 ml of water, recentrifuged and resuspended in 10 ml of a solution containing 1.2M sorbitol, 25 mM $Na_2EDTA$ pH=8.0 and 6.7 mg/ml dithiothreitol. The suspension was incubated at 30° C. for 15 minutes, centrifuged, and the cells resuspended in 10 ml of a solution containing 1.2M sorbitol, 10 mM $Na_2EDTA$, 0.1M sodium citrate, pH=5.8, and 2 mg Novozym® 234. The suspension was incubated at 30° C. for 30 minutes, the cells collected by centrifugation, washed in 10 ml of 1.2M sorbitol and 10 ml of CAS (1.2M sorbitol, 10 mM $CaCl_2$, 10 mM Tris HCl (Tris=Tris(hydroxymethyl)-aminomethane, pH=7.5) and resuspended in 2 ml of CAS. For transformation, 0.1 ml of CAS-resuspended cells were mixed with approx. 1 µg of plasmid pKFN-1508 and left at room temperature for 15 minutes. 1 ml of (20% polyethylene glycol 4000, 20 mM $CaCl_2$, 10 mM $CaCl_2$, 10 mM Tris HCl, pH=7.5) was added and the mixture left for a further 30 minutes at room temperature. The mixture was centrifuged and the pellet resuspended in 0.1 ml of SOS (1.2M sorbitol, 33% v/v YPD, 6.7 mM $CaCl_2$, 14 µg/ml leucine) and incubated at 30° C. for 2 hours. The suspension was then centrifuged and the pellet resuspended in 0.5 ml of 1.2M sorbitol. Then, 6 ml of top agar (the SC medium of Sherman et al., *(Methods in Yeast Genetics,* Cold Spring Harbor Laboratory (1982)) containing 1.2M sorbitol plus 2.5% agar) at 52° C. was added and the suspension poured on top of plates containing the same agar-solidified, sorbitol containing medium.

Transformant colonies were picked after 3 days at 30° C., reisolated and used to start liquid cultures. One such transformant KFN-1512 was selected for further characterization.

Yeast strain KFN-1512 was grown on YPD medium (1% yeast extract, 2% peptone (from Difco Laboratories), and 6% glucose). A 200 ml culture of the strain was shaken at 250 rpm at 30° C. for 3 days to an O.D. at 600 nm of about 20. After centrifugation, the supernatant was analyzed by FPLC ion exchange chromatography. The yeast supernatant was filtered through a 0.22 µm Millex GV filter unit, and 1 ml was applied on a MonoS cation exchange column (0.5×5 cm) equilibrated with 20 mM formic acid, pH 3.7. After washing with equilibration buffer, the column was eluted with a linear NaCl gradient (0.1M) in equilibration buffer. Trypsin inhibitor activity was quantified in the eluted fractions by spectrophotometric assay (Kassel, B., *Methods Enzymol.* 19 (1970), 844–852) and furthermore by integration of absorption at 280 nm from $$E_{280}^{1\%} \text{ (aprotinin)}=8.3$$

In order to obtain material for toxicology studies, yeast strain KFN-1512 was grown on a larger scale. The aprotinin analog was purified by a combination of ion exchange chromatography and reverse phase HPLC.

7.10. EXAMPLE 10: PRODUCTION OF [Glu1, Glu2, Glu6 ]APROTININ FROM YEAST STRAIN KFN-1514

A synthetic gene coding for [Glu1, Glu42, Glu46]-aprotinin was constructed from 10 oligonucleotides by ligation as described in Example 9.

The pTZ19R-derived plasmid pKFN-1505 containing the synthetic gene fused in frame to a synthetic yeast leader peptide was constructed as described in Example 9.

By following the procedure of Example 1, a yeast expression plasmid pKFN-1510 was obtained containing the following construction $TPI_P$-LaC212spx3 signal-leader (1-47)-GluArgLeuGluLysArg [Glu1, Glu42, Glu46]-aprotinin-$TPI_T$.

The DNA sequence of the 412 bp EcoRI-XbaI fragment from pKFN-1505 and pKFN-1510 is SEQ ID NOS: 54 and 55. Plasmid pKFN-1510 was transformed in yeast strain S0MT663 as described above resulting in yeast strain KFN-1514.

Culturing of the transformed strain KFN-1514 in YPD-medium, analysis for [Glu1, Glu42, Glu46]-aprotinin in the supernatant, and production of material for toxicological studies was performed as described above.

7.11. EXAMPLE 11: PRODUCTION OF [Glu42, Glu46]-APROTININ FROM YEAST STRAIN KFN-1544

The 144 bp AvaII-XbaI fragment encoding [Glu42, Glu46]-aprotinin (12-58) from pKFN-1505 was used to replace the corresponding DNA fragment encoding aprotinin(12-58) from plasmid pKFN-1000 resulting in plasmid pKFN-1528. Plasmid pKFN-1000 is described in Example 4 of International Patent Application, Publication NO. WO 90/10075.

By following the procedure of Example 9, a yeast expression plasmid pKFN-1541 was obtained containing the following construction $TPI_P$-LaC212spx3 signal-leader (1-47)-GluArgLeuGluLysArg-[Glu42, Glu46]-aprotinin-$TPI_T$.

The DNA sequence of the 412 bp EcoRI-XbaI fragment from pKFN-1528 and pKFN-1541 is SEQ ID NOS:56 and 57. Plasmid pKFN-1541 was transformed in yeast strain MT663 as described above resulting in yeast strain pKFN-1544.

Culturing of the transformed strain KFN-1544 in YPD-medium, analysis for [Glu42, Glu46]-aprotinin in the supernatant and production of material for toxicological studies was performed as described above.

7.12. EXAMPLE 12: PRODUCTION OF [Ser10, Asp24, Thr26, Glu31, Asn41, Glu53]-APROTININ FROM YEAST STRAIN KFN-1545

The synthetic gene coding for [Ser10, Asp24, Thr26, Glu31, Ash41, Glu53]was constructed from 10 oligonucleotides by ligation as described in Example 9 (see Section 7.9., supra).

The pTZ19R-derived plasmid pKFN-1530 containing the synthetic gene fused in frame to a synthetic yeast leader peptide sequence was constructed as described in Example 9 (see Section 7.9., supra).

By following the procedure of Example 9 (see Section 7.9., supra), a yeast expression plasmid pKFN-1532 was obtained containing the following construction $TPI_P$-LaC212spx3 signal-leader (1-47)-GluArgLeuGluLysArg-[Ser10, Asp24, Thr26, Glu3i, Ash41, Glu52]-aprotinin-$TPI_T$. The DNA sequence of the 412 bp EcoRI-XbaI fragment from 1530 and pKFN-1532 is SEQ ID NOS: 58 and 59.

Plasmid pKFN-1532 was transformed in yeast strain MT663 as described above resulting in yeast strain KFN-1545.

Culturing of the transformed strain KEN-1545 in YPD-medium, analysis for [Ser10, Asp24, Thr26, Glu31, Ash41, Glu53]-aprotinin in the supernatant and production of material for toxicological studies was performed as described above.

7.13. EXAMPLE 5: PRODUCTION OF [Ser10, Leu20, Gly40, Ash41, Gln44, Tyr46]-APROTININ FROM YEAST STRAIN KFN-1547

The synthetic gene coding for [Ser10, Leu20, Gly40, Asn41, Gly42, Gln44, Tyr46]-aprotinin was constructed from 10 oligonucleotides by ligation as described in Example 9 (see Section 7.9., supra).

The pTZ19R-derived plasmid pKFN-1534 containing the synthetic gene fused in frame to a synthetic yeast leader peptide sequence was constructed as described in Example 9 (see Section 7.9., supra).

By following the procedure of Example 9 (see Section 7.9., supra), a yeast expression plasmid pKFN-1537 was obtained containing the following construction $TPI_P$-LaC212Spx3 signal-leader (1-47)-GluArgLeuGluLysArg-[Ser10, Leu20, Gly40, Asn41, Gly42, Gln44, Tyr46]-aprotinin-$TPI_T$. The DNA sequence of the 412 bp EcoRI-XbaI fragment from pKFN-1534 and pKFN-1537 is SEQ ID NOS:60 and 61. Plasmid pKFN-1537 was transformed in yeast strain MT663 as described above resulting in yeast strain KFN-1547.

Culturing of the transformed strain KFN-1547 in YPD-medium, analysis for [Ser10, Leu20, Gly40, Asn41, Gly42, Gln44, Tyr46]-aprotinin in the supernatant and production of material for toxicological studies was performed as described above.

7.14. EXAMPLE 14: PRODUCTION OF Des-Arg1, des-Pro2-[Ser 42, Glu46]-APROTININ FROM YEAST STRAIN KFN-1660

The 1.4 kb AhaII-StyI fragment and the 1.8 kb AhaII-SalI fragment both from plasmid pKFN-306 were ligated to a duplex consisting of the following two synthetic oligonucleotides:

NOR-2188: 5' CAAGGCTGGTTTGTGTCAAACTTTCGTTTACGGTGGCTGCA-GAGCTAAGTCCAACAACTTCGAATCTGCTGAAGACTGCATG-AGAACTTGTGGTGGTGCCTAATCTAGAG 3' (SEQ ID NO:62)

NOR-2189: 5' TCGACTCTAGATTAGGCACCACCACAAGTTCTCATGCAGTC-TTCAGCAGATTCGAAGTTGTTGGACTTAGCTCTGCAGCCAC-CGTAAACGAAAGTTTGACACAAACCAGC 3' (SEQ ID NO:63)

Plasmid pKFN-306 is a pTZ19R derived plasmid with a 502 bp EcoRI-XbaI insert containing the Saccharomyces cerevisiae mating factor alpha-1-signal-leader (1-85) gene fused in-frame with a synthetic gene for des-Arg1, des-Pro2-[Ser42]-aprotinin. The construction of plasmid pKFN-306 is described in WO 89/01968.

The ligation mixture was used to transform a competent E. coli strain (r−, m+) selecting for ampicillin resistance. DNA sequencing (Sanger, F., Micklen, S., and Coulsen, A. R., Proc. Natl. Acad. Sci. USA 74 (1977) 5463– 5467) showed that plasmids from the resulting colonies contained the correct sequence for des-Arg1, Pro2-[Ser42, Glu46] aprotinin.

One plasmid pKFN-1629 was selected for further use.

By following the procedure of Example 9 (see Section 7.9., supra), a yeast expression plasmid pKFN-1656 was obtained containing the following construction: $TPI_P$-MFα1 signal-leader(1-85)-des-Arg1, des-Pro2-[Ser42,Glu46]-aprotinin-$TPI_T$.

The DNA sequence of the 502 bp EcoRI-XbaI fragment from pKFN-1629 and pKFN-1656 is SEQ ID NOS:64 and 65.

Plasmid pKFN-1656 was transformed in yeast strain MT663 as described above resulting in yeast strain KFN-1660.

Culturing of the transformed strain KFN-1660 in YPD-medium, analysis for des-Arg1, des-Pro2-[Ser42, Glu46]-aprotinin in the supernatant and production of material for toxicological studies was performed as described above.

7.15. EXAMPLE 15: PRODUCTION OF Des-Arg1, des-Pro2-[Ser2,Ala46]-APROTININ FROM YEAST STRAIN KFN-1661

The 1.4 kb AhaII-StyI fragment and the 1.8 kb AhaII-SalI fragment both from plasmid pKFN-306 were ligated to a duplex consisting of the following two synthetic oligonucleotides:

NOR-2196: 5' CAAGGCTGGTTTGTGTCAAACTTTCGTTTACGGTGGCTGCA-GAGCTAAGTCCAACAACTTCGCTTCTGCTGAAGACTGCATG-AGAACTTGTGGTGGTGCCTAATCTAGAG 3' (SEQ ID NO:66)

NOR-2197: 5' TCGACTCTAGATTAGGCACCACCACAAGTTCTCATGCAGTC-TTCAGCAGAAGCGAAGTTGTTGGACTTAGCTCTGCAGCCAC-CGTAAACGAAAGTTTGACACAAACCAGC 3' (SEQ ID NO:67)

Plasmid pKFN-306 is a pTZ19R derived plasmid with a 502 bp EcoRI-XbaI insert containing the Saccharomyces cerevisiae mating factor alpha 1 signal-leader (1-85) gene fused in-frame with a synthetic gene for des-Arg1, des-Pro2-[Ser42]-aprotinin. The construction of plasmid pKFN-306 is described in Example 3 (see Section 7.3., supra).

The ligation mixture was used to transform a competent E. coli strain (r−, m+) selecting for ampicillin resistance. DNA sequencing (Sanger, F., Micklen, S., and Coulsen, A. R., Proc. Natl. Acad. Sci. USA 74 (1977) 5463–5467) showed that plasmids from the resulting colonies contained the correct sequence for des-Arg1, des-Pro2-[Ser42,Glu46] aprotinin. One plasmid pKFN-1631 was selected for further use.

By following the procedure of Example 9 (see Section 7.9., supra), a yeast expression plasmid pKFN-1657 was obtained containing the following construction: $TPI_P$-MFαl signal-leader(1-85)-des-Argl, des-Pro2-[Ser42,Ala46]-aprotinin-$TPI_T$.

The DNA sequence of the 502 bp EcoRI-XbaI fragment form pKFN-1631 and pKFN-1657 is SEQ ID NOS:68 and 69.

Plasmid pKFN-1657 was transformed in yeast strain MT663 as described above resulting in yeast strain KFN-1661.

Culturing of the transformed strain KFN-1661 in YPD-medium, analysis for des-Argl, des-Pro2-[Ser42,Ala46]-aprotinin in the supernatant and production of material for toxicological studies was performed as described above.

7.16. EXAMPLE 16: PRODUCTION OF Des-Argl, des-Pro2-[Ser10, Asp24, Thr26, Glu31, Asn41, Glu53]-APROTININ FROM YEAST STRAIN KFN-1735

A synthetic gene coding for des-Argl,des-Pro2-[Ser10, Asp24, Thr26, Glu31, Ash41, Glu53]-aprotinin was constructed from 10 oligonucleotides by ligation as described in Example 9 (see Section 7.9., supra).

The pTZ19R-derived plasmid pKFN-1707 containing the synthetic gene fused in frame to a synthetic yeast leader peptide was constructed as described in Example 9 (see Section 7.9., supra).

By following the procedure of Example 9 (see Section 7.9., supra), a yeast expression plasmid pKFN-1709 was obtained containing the following construction $TPI_P$-LaC212spx3 signal-leader(1-47)-GluArgLeuGluLysArg-des Argl,des-Pro2-[Ser10, Asp24, Thr26, Glu31, Asn41, Glu53]-aprotinin-$TPI_T$.

The DNA sequence of the 406 bp EcoRI-XbaI fragment from pKFN-1707 and pKFN-1709 is SEQ ID NOS: 70 and 71.

Plasmid pKFN-1709 was transformed in yeast strain MT663 as described above resulting in yeast strain KFN-1735.

Culturing of the transformed strain KFN-1735 in YPD-medium, analysis for des -Argl, des-Pro2-[Ser10, Asp24, Thr26, Glu31, Asn41, Glu53]-aprotinin in the supernatant and production of material for toxicological studies was performed as described above.

7.17. EXAMPLE 17: PRODUCTION Of Des-Argl, -des-Pro2-[Asp24, Thr26, Glu31, Glu53]-APROTININ FROM YEAST STRAIN KFN-1737

The 1.8 kb AhaII-XbaI fragment and the 1.4 kb AhaII-AvaII fragment both from plasmid pKFN-306 (see example 5) were ligated to a synthetic 141 bp AvaII-XbaI fragment encoding [Asp24, Thr26, Glu31, Glu53]-aprotinin. The resulting pTZ19R-derived plasmid was pKFN-1711.

By following the procedure of Example 9 (see Section 7.9., supra), a yeast expression plasmid pKFN-1713 was obtained containing the following construction $TPI_P$-MFαl signal-leader (1-85)-des -Argl, des-Pro2-[Asp24, Thr26, Glu31, Glu53]-aprotinin-$TPI_T$.

The DNA sequence of the 502 bp EcoRI-XbaI fragment from pKFN-1711 and pKFN-1713 is SEQ ID NOS:72 and 73.

Plasmid pKFN-1713 was transformed in yeast strain MT663 as described above resulting in yeast strain KFN-1737. Culturing of the transformed strain KFN-1737 in YPD-medium, analysis for des-Argl,des-Pro2-[Asp24, Thr26, Glu31, Glu53]-aprotinin in the supernatant and production of material for toxicological studies was performed as described above.

7.18. EXAMPLE 18: PRODUCTION Of Des-Argl,des-Pro2-[Ser10, Gly40, Asn41, Gly42, Glu53]-APROTININ FROM YEAST STRAIN KFN-1739

A synthetic gene coding for des-Argl,des-Pro2-[Ser10, Sly40, Asn41, Gly42, Glu53]-aprotinin was constructed from 10 oligonucleotides by ligation as described in Example 9 (see Section 7.9., supra).

The pTZ19R-derived plasmid pKFN-1715 containing the synthetic gene fused in frame to a synthetic yeast leader peptide was constructed as described in Example 9 (see Section 7.9., supra).

By following the procedure of Example 9 (see Section 7.9., supra), a yeast expression plasmid pKFN-1718 was obtained containing the following construction $TPI_P$-LaC212 spx3 signal-leader (1-47)-GluArgLeuGluLysArg-des Argl,des-Pro2-[Ser10, Gly40, Asn41, Gly42, Glu53]-aprotinin-$TPI_T$.

The DNA sequence of the 406 bp EcoRI-XbaI fragment from pKFN-1715 and pKFN-1718 is SEQ ID NOS:74 and 75.

Plasmid pKFN-1718 was transformed in yeast strain MT663 as described above resulting in yeast strain KFN-1739. Culturing of the transformed strain KFN-1739 in YPD-medium, analysis for des-Argl,Pro2-[Ser10, Gly40, Asn41, Gly42, Glu53]-aprotinin in the supernatant and production of material for toxicological studies was performed as described above.

7.19. EXAMPLE 19: PRODUCTION OF Des-Argl,des-Pro2-[Ser42, Glu53]-APROTININ FROM YEAST STRAIN KFN-1742

The 1.8 kb AhaII-XbaI fragment and the 1.4 kb AhaII-AvaII fragment both from plasmid pKFN-306 (see example 5) were ligated to a synthetic 141 bp AvaII-XbaI fragment encoding [Ser42, Glu53]-aprotinin. The resulting pTZ19R-derived plasmid was pKEN-1721.

By following the procedure of Example 9 (see Section 7.9., supra), a yeast expression plasmid pKFN-1724 was obtained containing the following construction $TPI_P$-MFαl signal-leader (1-85)-des-Argl, des-Pro2-[Ser42, Glu53]-aprotinin- $TPI_T$.

The DNA sequence of the 502 bp EcoRI-XbaI fragment from pKFN-1721 and pKFN-1724 is SEQ ID NOS:76 and 77.

Plasmid pKFN-1724 was transformed in yeast strain MT663 as described above resulting in yeast strain KFN-1742. Culturing of the transformed strain KFN-1742 in YPD-medium, analysis for des-Argl, des-Pro2-[Ser42, Glu53]-aprotinin in the supernatant and production of material for toxicological studies was performed as described above.

7.20. EXAMPLE 20: PRODUCTION OF Des-Argl, des-Pro2-[Glu42, Glu53]-APROTININ FROM YEAST STRAIN KFN-1752

The 1.8 kb AhaII-XbaI fragment and the 1.4 kb AhaII-AvaII fragment both from plasmid pKFN-306 (see Example 14) were ligated to a synthetic 141 bp AvaII-XbaI fragment encoding [Glu42, Glu53]-aprotinin. The resulting pTZ19R-derived plasmid was pKFN-1762.

By following the procedure of Example 9 (see Section 7.9., supra), a yeast expression plasmid pKFN-1765 was obtained containing the following construction TPI$_P$-MFα1 signal-leader (1-85)-des-Argl, des-Pro2-[Glu42, Glu53]-aprotinin-TPI$_T$.

The DNA sequence of the 502 bp EcoRI-XbaI fragment from DKFN-1762 and pKFN-1765 is SEQ ID NOS: 78 and 79.

Plasmid pKFN-1765 was transformed in yeast strain MT663 as described above resulting in yeast strain KFNS-01752. Culturing of the transformed strain KFN-1752 in YPD-medium, analysis for des-Argl, des-Pro2-[Glu42, Glu53]-aprotinin in the supernatant and production of material for toxicological studies was performed as described above.

7.21. EXAMPLE 21: PRODUCTION OF Des-Argl,des-Pro2-[Glu26, Ser42, Glu53]-APROTININ FROM YEAST STRAIN KFN-1755

The 1.8 kb AhaII-XbaI fragment and the 1.4 kb AhaII-AvaII fragment both from plasmid pKFN-306 (see Example 14) were ligated to a synthetic 141 bp AvaII-XbaI fragment encoding [Glu26, Ser42, Glu53]-aprotinin. The resulting pTZ19R-derived plasmid was pKFN-1768.

By following the procedure of Example 9 (see Section 7.9., supra), a yeast expression plasmid pKFN-1770 was obtained containing the following construction TPI$_P$-MFα1 signal-leader (1-85)-des-Argl, des-Pro2-[Glu26, Ser42, Glu53]-aprotinin-TPI$_T$.

The DNA sequence of the 502 bp EcoRI-XbaI fragment from pKFN-1768 and pKFN-1770 is SEQ ID NOSS:80 and 81 and 65.

Plasmid pKFN-1770 was transformed in yeast strain MT663 as described above resulting in yeast strain KFN-1755. Culturing of the transformed strain KFN-1755 in YPD-medium, analysis for des-Argl, des-Pro2-[Glu26, Ser42, Glu53]-aprotinin in the supernatant and production of material for toxicological studies was performed as described above.

7.22. EXAMPLE 22: PRODUCTION OF Des-Argl,des-Pro2-[Gluu26, Glu42, Glu53]-APROTININ FROM YEAST STRAIN KFN-1756

The 1.8 kb AhaII-XbaI fragment and the 1.4 kb AhaII-AvaII fragment both from plasmid pKFN-306 (see Example 5) were ligated to a synthetic 141 bp AvaII-XbaI fragment encoding [Glu26, Glu42, Glu53]-aprotinin. The resulting pTZ19R-derived plasmid was pKFN-1771.

By following the procedure of Example 9 (see Section 7.9., supra), a yeast expression plasmid pKFN-1773 was obtained containing the following construction: TPI$_P$-MFα1 signal-leader (1-85)-des-Argl, des-Pro2-[Glu26, Glu42, Glu53]-aprotinin-TPI$_T$.

The DNA sequence of the 502 bp EcoRI-XbaI fragment from pKFN-1771 and pKFN-1773 is SEQ ID NOS:82 and 83.

Plasmid pKFN-1773 was transformed in yeast strain MT663 as described above resulting in yeast strain KFN-1756. Culturing of the transformed strain KFN-1756 in YPD-medium, analysis for des-Argl, des-Pro2-[Ser42, Glu42, Glu53]-aprotinin in the supernatant and production of material for toxicological studies was performed as described above.

7.23. EXAMPLE 23: TOXICOLOGICAL SCREENING OF APROTININ ANALOGS BY SINGLE-DOSE INTRAVENOUS ADMINISTRATION TO WISTAR RATS

7.23.1. MATERIALS

The following aprotinin analogs with a reduced positive net charge and thermal stability compared to recombinant aprotinin (1-58) were selected for toxicological screening: KFN-1512, KFN-1514, KFN-1544, KFN-1545, KFN-1547, KFN-1660, KFN-1661, KFN-322, KFN-324, KFN-396, KFN-399, KFN-430, and KFN-773. Their main characteristics as seen from a toxicological point of view, are shown in Table 6. Data for recombinant aprotinin are shown for comparison. The denaturation temperature is shown as an indication of biological stability.

TABLE 6

| | General Information | | |
|---|---|---|---|
| KFN-Type | Chain Length | Net Charge | Denaturation T, °C. |
| rAprotinin | 1–58 | +6 | >100 |
| 1512 | 1–58 | −2 | 87 |
| 1514 | 1–58 | 0 | 88 |
| 1544 | 1–58 | +2 | 98 |
| 1545 | 1–58 | 0 | 93 |
| 1547 | 1–58 | +2 | 86 |
| 1660 | 3–58 | +2 | 77 |
| 1661 | 3–58 | +3 | 79 |
| 1735 | 3–58 | −1 | 68 |
| 1737 | 3–58 | 0 | 70 |
| 1739 | 3–58 | +1 | 81 |
| 1742 | 3–58 | +2 | 71 |
| 1752 | 3–58 | +1 | |
| 1755 | 3–58 | 0 | 68 |
| 1756 | 3–58 | −1 | 70 |
| 322 | 3–58 | +5 | 84 |
| 324 | 3–58 | +4 | 84 |
| 396 | 3–58 | +3 | 75 |
| 399 | 3–58 | +2 | 67 |
| 430 | 3–58 | +3 | 70 |
| 773 | 3–58 | +3 | 71 |

7.23.2. DESIGN

On Day 1 of the screening of each analog, groups of 2 male and 2 female rats received 33, 100, 300, or 900 mg analog/kg body weight. Two similarly constituted control groups received physiological saline or physiological saline acidified with hydrochloric acid to an approximate pH 4.5. The latter solution served as vehicle. The dose volume was 10 ml/kg body weight in all cases. The rats were observed for 7 days and killed on Day 8. At autopsy the kidneys were weighed and prepared for histopathology. Response variables are shown in the heading of Table 7.

7.23.3. RESULTS

Results from individual screenings are summarized in Table 7. Data for recombinant aprotinin are included for comparison (dosage: 11–300 mg/kg). KFN-1512 could not be dissolved as required for administration of the top dose (900 mg/kg).

A single animal died at 900 mg/kg KFN-1545 and all animals receiving a dose of 900 mg/kg KFN-322, KFN-430, and 773 were found dead/killed in extremis by Day 1–2. Apart from this, no fatalities were seen.

No histopathological kidney change was seen after administration 900 mg/kg of KFN-399, or after 300 mg/kg body weight of KFN-1512, KFN-1544, KFN-1545, KFN-396, KFN-430, KFN-773, and KFN-1660, or after 100 mg/kg of KFN-322 and KFN-324. Furthermore, no histopathological kidney change was seen after administration of 900 mg/kg body weight of KFN-1514, KFN-1547, and KFN-1661. Thus all analogs had no-toxic-effect levels concerning histopathological kidney change of 300 mg/kg or above, as compared to 11 mg/kg for aprotinin.

With respect to the other response variables the analogs equaled or were superior to aprotinin.

TABLE 7

| | No-toxic-effect levels by response variable, mg/kg | | | | | | | |
|---|---|---|---|---|---|---|---|---|
| | Clinical Observations | | | | Macro- | Micro- | | |
| KFN-type | 0–30 min after dosage | 2 hours after dosage | Daily | Mortality | scopic observations | scopic observations | Body weight Day 8 | Kidney weight Day 8 |
| rAprotinin [1,2] | 33 | 300 | 300 | 300 | 33 | 11 | 100 | 100 |
| 1512 [1] | 33 | 300 | 300 | 300 | 300 | 300 | 300 | 300 |
| 1514 | 900 | 900 | 900 | 900 | 900 | 900 | 900 | 900 |
| 1544 | 33 | 100 | 100 | 900 | 300 | 300 | 900 | 300 |
| 1545 | 33 | 900 | 300 | 300 | 300 | 300 | 300 | 300 |
| 1547 | 33 | 300 | 900 | 900 | 900 | 900 | 900 | 900 |
| 1660 | 300 | 900 | 900 | 900 | 900 | 900 | 900 | 900 |
| 1661 | 100 | 900 | 900 | 900 | 300 | 900 | 900 | 900 |
| 322 | 100 | 900 | 300 | 300 | 300 | 100 | 100 | 300 |
| 324 | 33 | 300 | 300 | 900 | 300 | 100 | 300 | 300 |
| 396 | 300 | 900 | 900 | 900 | 900 | 300 | 300 | 900 |
| 399 | 100 | 300 | 300 | 900 | 900 | 900 | 900 | 300 |
| 430 | 100 | 100 | 300 | 300 | 300 | 300 | 300 | 300 |
| 773 | 100 | 100 | 300 | 300 | 300 | 300 | 300 | 300 |

[1,2] Top Dose = 300 mg/kg
[2] Low Dose = 11 mg/kg

7.23.4. CONCLUSION

The toxicity profile of aprotinin analogs assessed by single-dose intravenous screening in Wistar rats was improved to a varying degree as compared to the toxicity profile of aprotinin. All aprotinin analogues had no-nephrotoxic-effect levels of 100 mg/kg or more as compared to 11 mg/kg for r-Aprotinin.

7.24. EXAMPLE 16: ELIMINATION AND DISTRIBUTION OF RECOMBINANT APROTININ AND APROTININ ANALOGS

7.24.1. MATERIALS

Recombinant authentic aprotinin and the analogues produced according to Examples 1–4 and 9–15 were dissolved in 0.9% NaCl in order to obtain a dose volume of 1 μl/g rat. The concentrations of the injection solutions were controls analyzed by methods given in the method section.

7.24.2. METHODS

Female Wistar rats, weighing 200–230 g were used. Aprotinin and analogs were tested in two different models, 1) anaesthetized and 2) unanesthetized rats.

7.24.3. ANAESTHETIZED RATS

The rats were anaesthetized by intraperitoneal injection of pentobarbital sodium. The carotid artery and the jugular vein were exposed and cannulated with S0 polyethylene catheters (PE-50, Intramedic). The carotid catheter was connected to a perfusor (B. Braun) for infusion of 3.8 ml 0.9% NaCl/h, and to a blood pressure transducer. Changes in blood pressure were recorded by using a chart recorder (Kipp & Zonen, BD 9). The analogues were administered as bolus injections over 15 seconds through the jugular catheter.

Blood samples were obtained from the carotid catheter at 3, 10, 20, 40, and 60 minutes after administration. The samples (0.45 ml) were collected in 3 ml test tubes containing 50 μl 0.13M sodium citrate and centrifuged. Plasma was stored at –20° C. until analysis. Sixty minutes after administration the rats were killed with an excessive dose of pentobarbital sodium and the kidneys and liver were removed, weighed, and stored at 80° C.

7.24.4. UNANESTHRTIZED RATS

An oral dose of 2 ml distilled $H_2O$ was given prior to the administration of analogs. The analogs were given intravenously as bolus injections into a tail vein by using an intravenous catheter (venflon 22 G, Viggo-Spectramed, Helsingborg, Sweden). After administration, the catheter was flushed by 0.5 ml 0.9% NaCl and removed. A plaster was applied on the injection site in order to avoid bleeding from the tail. The rat was then placed in a metabolism cage in order to collect the urine produced.

After 3 hours the rat was killed by administration of $CO_2/O_2$ (9/1) into the cage, and the kidneys and liver were removed and stored at –80° C. until analysis. During the $CO_2$-administration, the rat emptied the urinary bladder and, after the rat was removed, the metabolism cage was rinsed with 0.9% NaCl in order to obtain a total urine-NaCl volume of 25 ml.

7.24.5. PREPARATION OF HOMOGENATES

One kidney (approx. 1 g) and approximately 2 g liver tissue were placed in separate 10 ml plastic test tubes and 2 ml 0.9% NaCl were added. The tissues were homogenized 5 min by using a High Intensity Ultrasonic Processor (Model VC50, solics & Materials Inc. Danbury Conn., USA). The kidney and liver homogenates were then diluted with saline in order to obtain a total volume of 10–25 and 4 ml, respectively.

7.24.6. METHODS OF ANALYSIS

The levels of aprotinin and analogues in plasma, liver homogenates and injection solutions were measured photometrically on a Cobas Fara II (Roche). Briefly, plasma, homogenates or injection solutions were precipitated with acid in order to remove other kallikrein inhibitors than aprotinin. The kallikrein inhibitory activity in the sample were measured by using kallikrein from porcine pancreas (Sigma K 3627) and the chromogenic substrate S2266 (Kabi).

The levels in kidney homogenates and urine were measured by the same method, except for the precipitation step which was omitted, since the intrinsic kallikrein inhibitory activity in the diluted homogenates and urine was negligible.

Separate standard curves were employed for each analog in each medium.

7.24.7. STUDY DESIGN 4 groups of anaesthetized and 14 groups of unanesthetized rats were studied. A dose of 1.56 μmoles (approximately 10 mg) aprotinin or aprotinin analogue per kg body weight were administered to each rat. Basal data on the 28 groups are given in Table 8.

TABLE 8

| Groups | n | BW | KW | LW |
|---|---|---|---|---|
| rAprotinin A | 5 | 251.8 | 0.98 | 9.9 |
| KFN 1512 A | 4 | 230.0 | 0.84 | 9.6 |
| KFN 1514 A | 4 | 220.5 | 0.85 | 8.6 |
| KFN 1544 A | 4 | 226.0 | 0.97 | 9.3 |
| KFN 1545 A | 4 | 224.8 | 0.92 | 9.2 |
| KFN 1547 A | 4 | 229.0 | 0.75 | 8.6 |
| KFN 1660 A | 4 | 220.5 | 0.93 | 9.7 |
| KFN 1661 A | 4 | 240.8 | 0.97 | 9.0 |
| KFN 322 A | 4 | 244.0 | 0.83 | 9.0 |
| KFN 324 A | 4 | 235.0 | 0.87 | 8.9 |
| KFN 396 A | 4 | 266.0 | 0.98 | 10.0 |
| KFN 399 A | 4 | 254.7 | 0.88 | 9.3 |
| KFN 430 A | 4 | 235.3 | 0.93 | 8.7 |
| KFN 773 A | 4 | 253.3 | 0.94 | 8.9 |
| rAprotinin U | 4 | 192.5 | 0.77 | 9.8 |
| KFN 1512 U | 5 | 191.0 | 0.65 | 7.2 |
| KFN 1514 U | 6 | 188.3 | 0.69 | 7.3 |
| KFN 1544 U | 5 | 190.0 | 0.64 | 6.5 |
| KFN 1545 U | 6 | 185.8 | 0.66 | 7.3 |
| KFN 1547 U | 5 | 188.0 | 0.67 | 7.3 |
| KFN 1660 U | 6 | 205.0 | 0.77 | 8.5 |
| KFN 1661 U | 6 | 204.2 | 0.80 | 8.1 |
| KFN 322 | 6 | 193.3 | 0.71 | 8.7 |
| KFN 324 | 4 | 198.8 | 0.76 | 9.5 |
| KFN 396 | 5 | 194.0 | 0.77 | 10.7 |
| KFN 399 | 5 | 183.0 | 0.74 | 9.5 |
| KFN 430 | 4 | 195.0 | 0.77 | 8.9 |
| KFN 773 | 5 | 193.0 | 0.75 | 9.8 |

BW: Body weight (g). KW: Kidney weight (g)
LW: Liver weight (g). A: anaesthetized rat model
U: Unanaesthetized rat model.

7.24.8. RESULTS

7.24.8.1. ANALOGS IN KIDNEYS AND URINE

Figure 12:
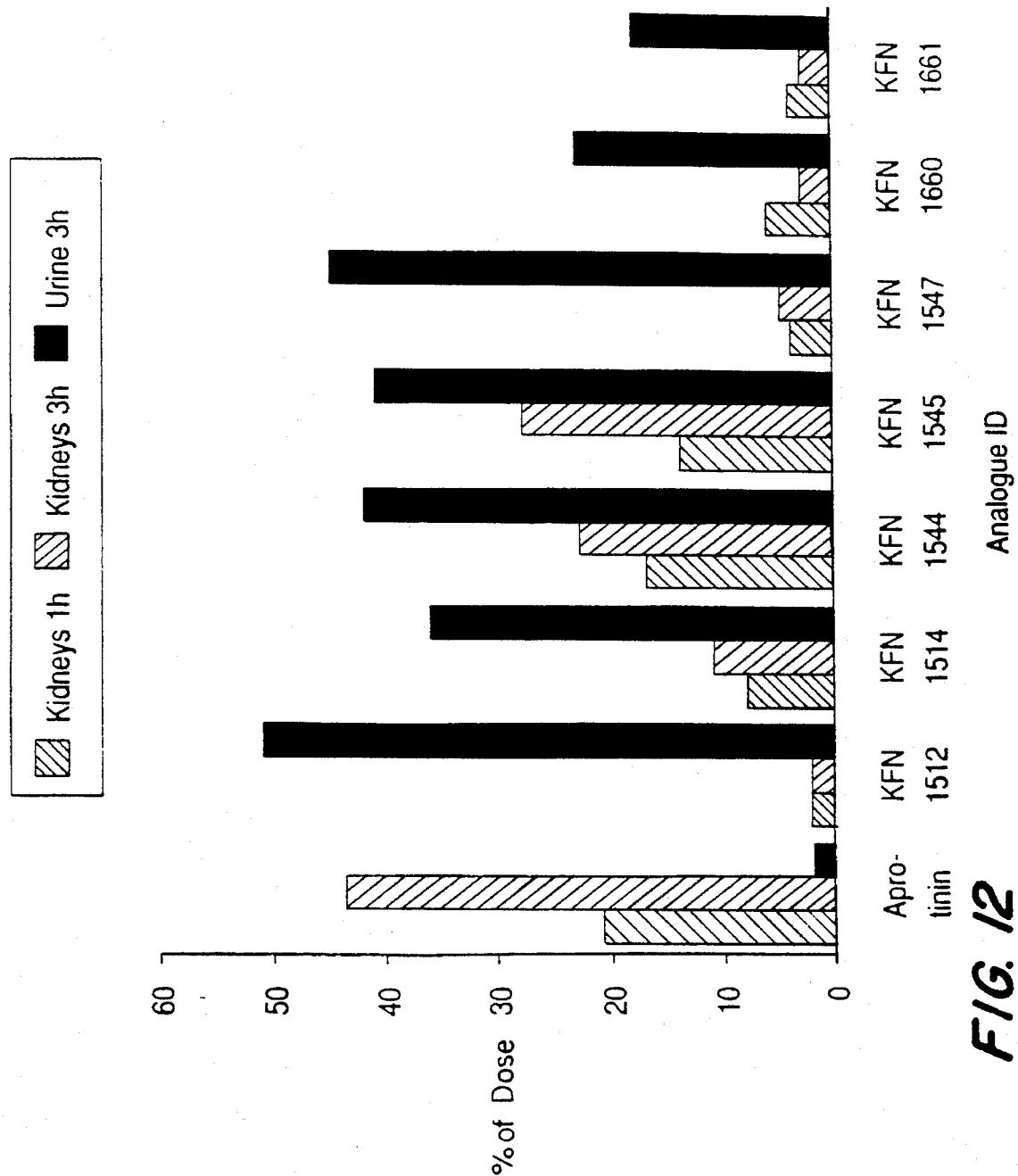
FIG. 12 is a graph showing the inhibitory activity in urine and kidneys after administration of aprotinin analogues with different net charges and thermal stability.
Figure 13:
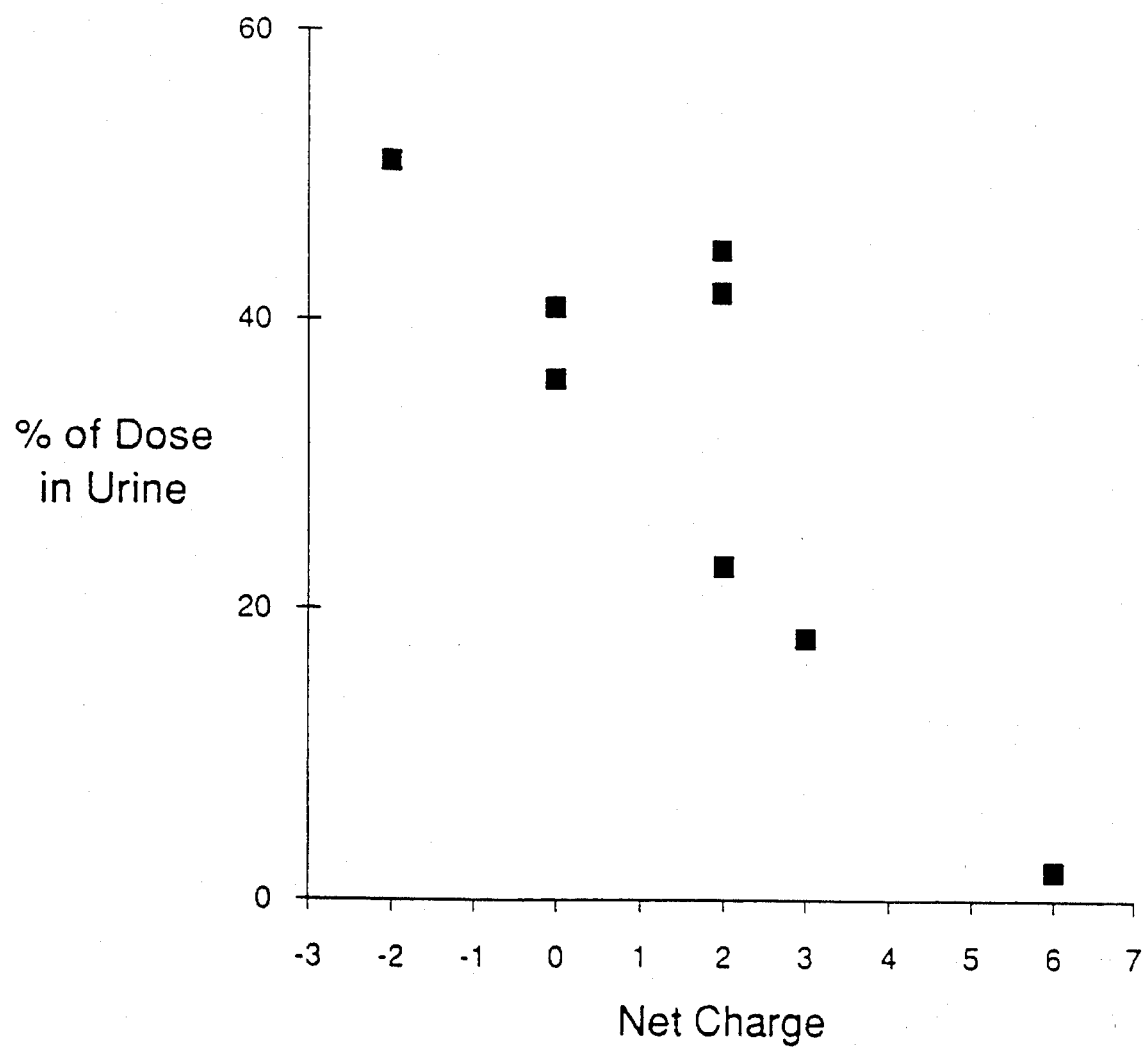
FIG. 13 shows the inhibitory activity in urine 3 hours after administration of aprotinin analogues with different net charges.

The total content in kidneys (in percent of dosage) after 1 and 3 hours and in urine after 3 h is shown in FIGS. 12 and 13 and Table 9. It appears that great differences between the analogues were found.

As regards aprotinin, the content in kidneys 1 hour after administration was approximately 20% of the dose, whereas the content increased to more than 40% after 3 hours. The excretion of aprotinin in urine was negligible.

In order to evaluate whether the excretion in urine after 3 hours was associated with the net charge of the analogs, the degree of correlation between these figures was calculated. The content in urine was found to be strongly correlated with the net charges of the analogues (see Table 9).

TABLE 9

| Analogs | Acc. index | Stab. index kidney | Denat. tp. (°C.) |
|---|---|---|---|
| rAprotinin A | 2.10 | 0.90 | 100 |
| KFN 1512 A | 0.66 | 0.67 | 87 |
| KFN 1514 A | 1.32 | 0.87 | 88 |
| KFN 1544 A | 1.32 | 1.05 | 98 |
| KFN 1545 A | 1.99 | 0.71 | 93 |
| KFN 1547 A | 1.22 | 0.65 | 86 |
| KFN 1660 A | 0.50 | 0.55 | 77 |
| KFN 1661 A | 0.77 | 0.55 | 79 |
| KFN 322 A | 0.67 | 0.83 | 84 |
| KFN 324 A | 0.45 | 0.51 | 79 |
| KFN 396 A | 0.18 | 0.37 | 75 |
| KFN 399 A | 0.41 | 0.43 | 67 |
| KFN 430 A | 0.44 | 0.42 | 70 |
| KFN 773 A | 1.04 | 0.70 | 71 |

7.24.9. STABILITY OF ANALOGS

In order to study the stability of the analogs in kidney tissue, one kidney from 14 anaesthetized rats (one from each group) was divided into two pieces of identical weight. One piece was stored at 37° C. and the other piece at 4° C. After 4 hours, the tissues were homogenized and the content of analogues was measured. A stability index was defined as the content in the piece stored at 37° C. divided by the content in the piece stored at 4° C. The stability indices are given in Table 10 showing that rAprotinin, KFN 1514, KFN 1544 and KFN 322, seem to be the most stable compounds as compared to e.g. KFN 1660 and KFN 396 which appears to be more unstable.

Figure 14:
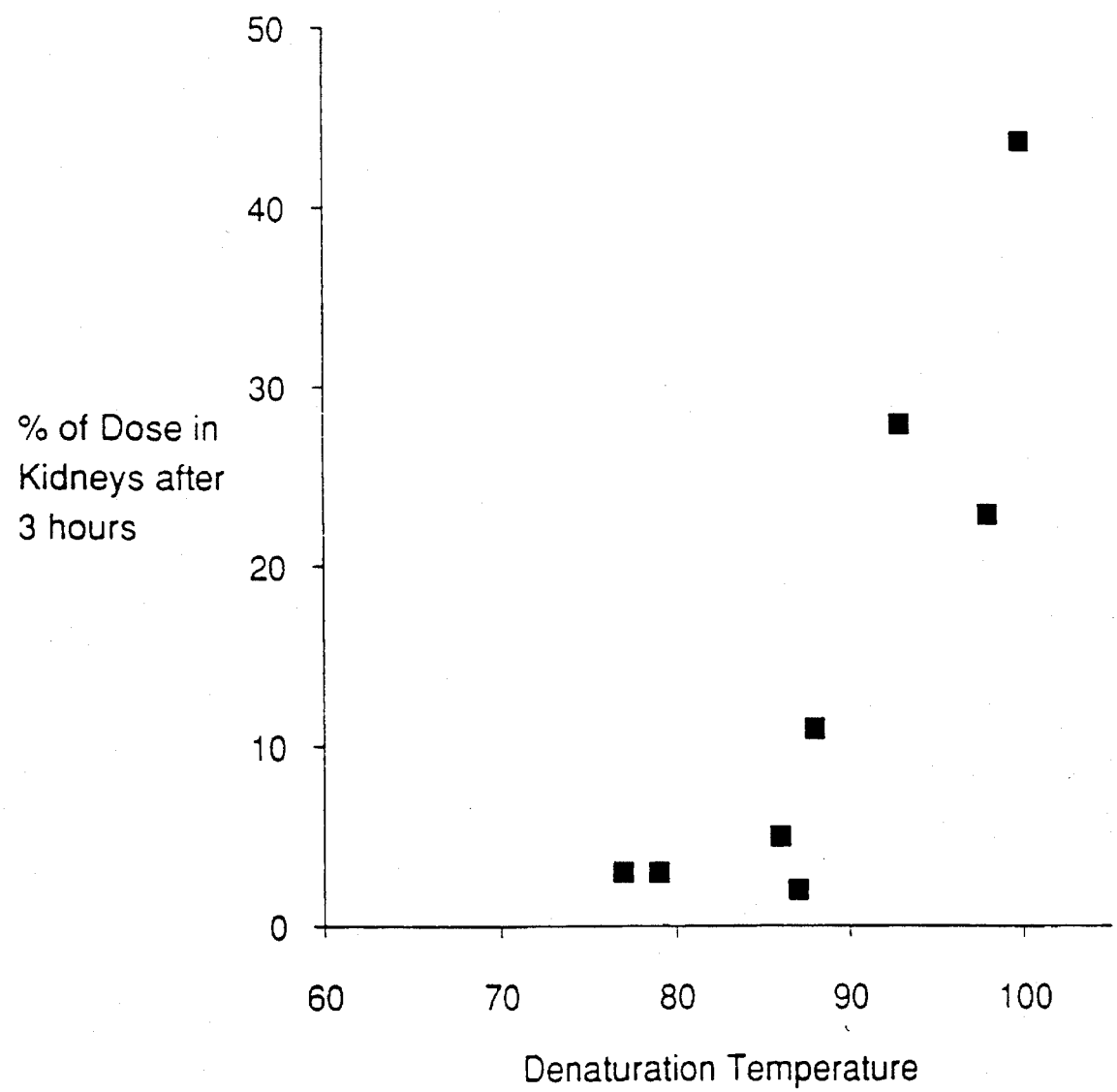
FIG. 14 shows the inhibitory activity in kidneys 3 hours after administration of aprotinin analogues with a different thermal stability.
Figure 15:
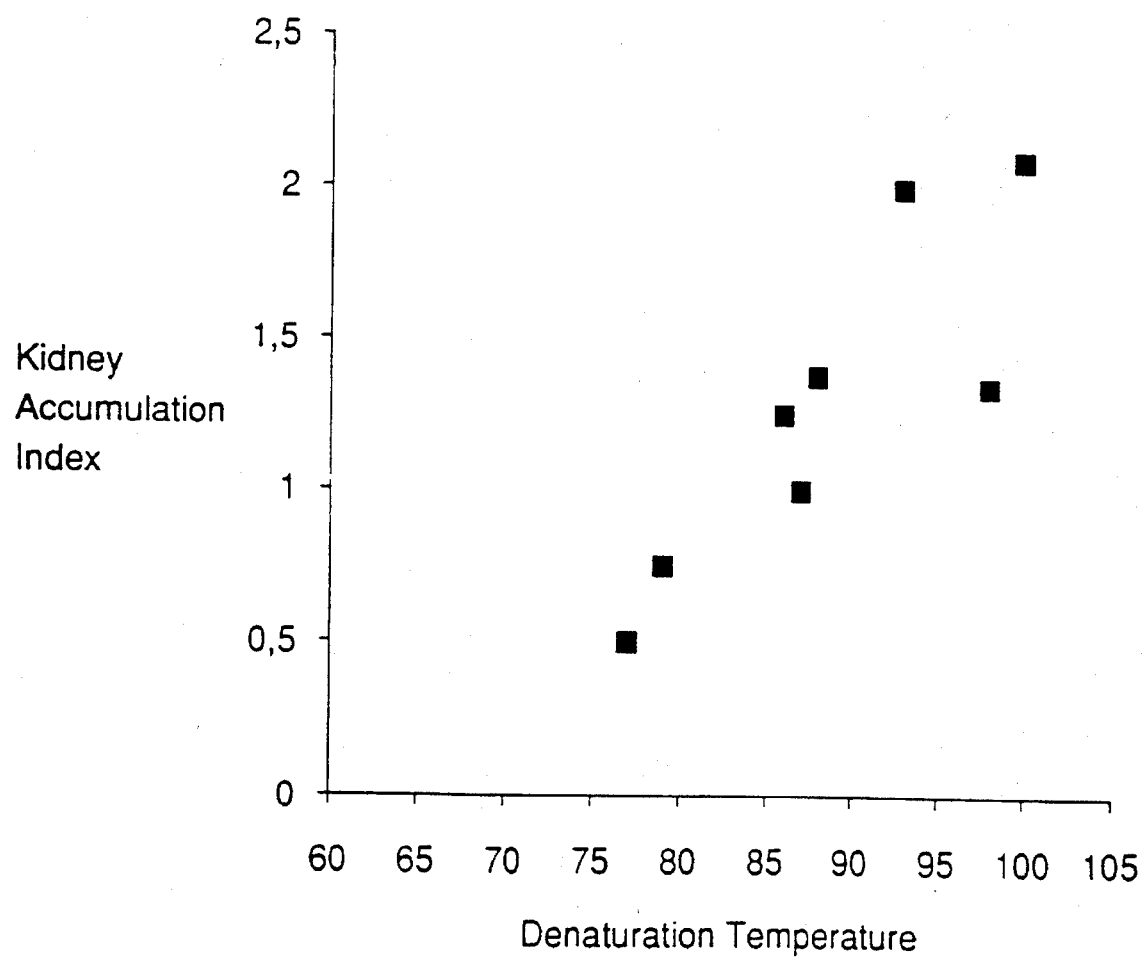
FIG. 15 shows the accumulation of inhibitory activity in kidneys after administration of aprotinin analogues with different thermal stability. The accumulation index is calculated as the inhibitory activity after 3 hours divided by the inhibitory activity after 1 hour.

The stability of analogues has also been studied by the determination of their denaturation temperature. The denaturation temperatures were found to be highly correlated with the content in kidney tissue 3 hours after administration (FIG. 14) and with the accumulation indices (FIG. 15), but not with urine excretion.

These data suggest that the net charge may be of importance for the excretion in urine, but of minor importance for the concentration and accumulation in kidneys. On the other hand, the renal accumulation seems to be related to the denaturation temperature and to the stability of analogues in kidney tissue.

It is, however, likely that the concentrations in kidney tissue, when measured 1 hour after administration, were changed due to degradation or redistribution. Thus, it is possible that the concentrations measured e.g. 10 min after administration would correlate with the net charge.

7.24.10. CONCLUSIONS

The following conclusions were made:
1) All analogs tested were taken up by the kidneys but to varying degrees. The accumulation in the kidneys seemed to be related to the thermostability and the stability in kidney tissue, but not to the net charge of the molecules.

2) The excretion in urine seemed to be associated with the net charge of the analogs, but not with the stability.

7.24.11. TOXICOLOGICAL SCRRENING OF APROTININ ANALOGS BY SINGLE-DOSE INTRAVENOUS ADMINISTRATION TO WISTAR RATS

7.24.11.1. MATERIALS

The following aprotinin analogues with a reduced positive net charge and thermal stability compared to recombinant aprotinin (1-58) were selected for toxicological screening: KFN 322, KFN 324, KFN 396, KFN 399, KFN 430 and KFN 773. Their main characteristics as seen from a toxicological point of view, are shown in Table 6. Data for recombinant aprotinin are shown for comparison. The denaturation temperature is shown as an indication of biological stability.

7.24.11.2. DESIGN

On Day 1 of the screening of each analog, groups of 4 rats (3 for KFN 322) received 33, 300, or 900 mg analogue/kg body weight. Two control groups received physiological saline or physiological saline acidified with hydrochloric acid to an approximate pH 4.5. The latter solution served as vehicle. The dose volume was 10 ml/kg body weight in all cases. The rats were observed for 7 days and killed on Day 8. At autopsy the kidneys were weighed and prepared for histopathology. Response variables are shown in the heading of Table 10.

TABLE 10

| KFN-type | Mortality | Macro-scopic changes | Micro-scopic changes | |
|---|---|---|---|---|
| | 900 mg/kg | 900 mg/kg | 900 mg/kg | 300 mg/kg |
| 322 | 3/3 | PK 3/3 | lethal | moderate |
| 324 | 0/4 | PK 3/4 | NF | moderate |

TABLE 10-continued

| KFN-type | Mortality | Macro-scopic changes | Micro-scopic changes | |
|---|---|---|---|---|
| | 900 mg/kg | 900 mg/kg | 900 mg/kg | 300 mg/kg |
| 396 | 0/4 | normal | weak | normal |
| 399 | 0/4 | normal | normal | normal |
| 430 | 4/4 | PK 2/2 | lethal | normal |
| 773 | 4/4 | normal | lethal | normal |

7.24.12. RESULTS

Results from individual screenings are summarized in Table 10. By way of comparison, rAprotinin (1-58) has a mortality dose of 300 mg/kg, macroscopic kidney changes at 33 mg/kg and microscopic kidney changes at 11 mg/kg.

No histopathological kidney change was seen after administration (300 mg/kg body weight) of the analogues except KFN 322 and KFN 324. Furthermore, no histopathological kidney change was seen after administration of 900 mg/kg body weight of KFN 399.

7.24.13. CONCLUSION

The toxicity profile of aprotinin analogues assessed by single-dose intravenous screening in Wistar rats was improved to a varying degree as compared to the toxicity profile of aprotinin.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A process for producing aprotinin or an analog thereof in yeast comprising culturing a yeast strain containing a replicable expression vector, the vector comprising a gene coding for aprotinin or an analog thereof and DNA sequences that allow for the expression of the aprotinin or analog thereof in a suitable nutrient medium and recovering the expressed aprotinin or analog thereof, in which the aprotinin or analog thereof has the following formula:

X-aprotinin(3-40)-$Y_n$-$Z_m$-aprotinin(43-58)

in which X is Arg-Pro, Pro or hydrogen, aprotinin(3-40) is the amino acid sequence from amino acid residue 3 to 40 in native aprotinin, Y is Lys, or a non-basic amino acid residue, Z is Arg or a non-basic amino acid residue, n and m are each 0 or 1, and aprotinin(43-58) is the amino acid sequence from amino acid residue 43 to 58 in native aprotinin.

2. The process according to claim 1, wherein the gene encodes amino acids 3-58 of native aprotinin as set forth in SEQ ID NO:29.

3. The process according to claim 1, wherein the gene encodes amino acids 3-58 of native aprotinin except that Arg at position 42 of native aprotinin is replaced with Ser as set forth in SEQ ID NO:34.

4. The process according to claim 1, wherein the gene encodes native aprotinin as set forth in SEQ ID NO:39.

5. The process according to claim 1, wherein the gene encodes an aprotinin analog in which Arg at position 42 of native aprotinin is replaced with Ser as set forth in SEQ ID NO:41.

6. A vector capable of replicating in yeast and comprising a gene coding for aprotinin or an analog thereof and a DNA sequence that allows for the expression of the aprotinin or an analog thereof, in which the aprotinin or analog thereof has the following formula:

X-aprotinin(3-40)-$Y_n$-$Z_m$-aprotinin(43-58)

in which X is Arg-Pro, Pro or hydrogen, aprotinin(3-40) is the amino acid sequence from amino acid residue 3 to 40 in native aprotinin, Y is Lys, or a non-basic amino acid residue, Z is Arg or a non-basic amino acid residue, n and m are each 0 or 1, and aprotinin(43-58) is the amino acid sequence from amino acid residue 43 to 58 in native aprotinin.

7. The vector according to claim 6 wherein the gone codes for amino acids 3-58 of native aprotinin as set forth as SEQ ID NO:29.

8. The vector according to claim 6 wherein the gone codes for amino acids 3-58 of native aprotinin except that Arg at position 42 of native aprotinin is replaced with Ser as set forth in SEQ ID NO:34.

9. The vector according to claim 6 wherein the gene codes for native aprotinin as set forth in SEQ ID NO:39.

10. A vector according to claim 6 wherein the gene codes for an aprotinin analog in which Arg at position 42 of native aprotinin is replaced with Ser as set forth in SEQ ID NO:41.

11. A gene encoding amino acids 3-58 of native aprotinin as set forth in SEO ID NO:29.

12. A gene encoding amino acids 3-58 of native aprotinin except that Arg at position 42 of native aprotinin is replaced with Ser as set forth in SEQ ID NO:34.

13. A yeast strain transformed with a vector capable of replicating in yeast and comprising a gene coding for aprotinin or an analog thereof and a DNA sequence that allows for the expression of the aprotinin or analog thereof, in which the aprotinin or analog thereof has the following formula:

X-aprotinin(3-40)-$Y_n$-$Z_m$-aprotinin(43-58)

in which X is Arg-Pro, Pro or hydrogen, aprotinin(3-40) is the amino acid sequence from amino acid residue 3 to 40 in native aprotinin, Y is Lys, or a non-basic amino acid residue, Z is Arg or a non-basic amino acid residue, n and m are each 0 or 1, and aprotinin(43-58) is the amino acid sequence from amino acid residue 43 to 58 in native aprotinin.

* * * * *